US005843693A

United States Patent [19]
Halenbeck et al.

[11] Patent Number: 5,843,693
[45] Date of Patent: Dec. 1, 1998

[54] ASSAY METHOD FOR SCREENING FOR INHIBITORS OF PROTNF CONVERSION

[75] Inventors: Robert F. Halenbeck, San Rafael; Michael Kriegler, Rancho Sante Fe; Carl Perez; David A. Jewell, both of San Diego; Kirston E. Koths, El Cerrito, all of Calif.

[73] Assignee: Chiron Corporation, Emeryville, Calif.

[21] Appl. No.: 394,600

[22] Filed: Feb. 27, 1995

Related U.S. Application Data

[63] Continuation-in-part of Ser. No. 230,428, Apr. 19, 1994, and Ser. No. 208,574, Mar. 7, 1994, abandoned, which is a continuation-in-part of Ser. No. 905,546, Jun. 25, 1992, abandoned, said Ser. No. 230,428, is a continuation of Ser. No. 905,546, which is a continuation-in-part of Ser. No. 395,253, Aug. 16, 1989, abandoned.

[51] Int. Cl.$^6$ .............................. C12Q 1/37; C12N 9/50
[52] U.S. Cl. .............................. 435/23; 435/219; 436/811
[58] Field of Search ............................... 435/7.1, 23, 218, 435/219; 436/501, 811; 424/85.1, 130.1, 146.1, 198.1; 514/454

[56] References Cited

U.S. PATENT DOCUMENTS

| | | | |
|---|---|---|---|
| 4,179,337 | 12/1979 | Davis et al. | 435/181 |
| 4,495,285 | 1/1985 | Shimizu et al. | 435/215 |
| 4,582,788 | 4/1986 | Ehrlich | 435/6 |
| 4,596,822 | 6/1986 | Powers et al. | 514/459 |
| 4,609,546 | 9/1986 | Hiratani | 424/83 |
| 4,677,063 | 6/1987 | Mark et al. | 435/68 |
| 4,677,064 | 6/1987 | Mark et al. | 435/68 |
| 4,683,195 | 7/1987 | Mullis et al. | 435/6 |
| 4,683,202 | 7/1987 | Mullis | 435/91 |
| 4,699,904 | 10/1987 | Doherty et al. | 514/202 |
| 4,704,692 | 11/1987 | Ladner | 364/496 |
| 4,711,886 | 12/1987 | Finke et al. | 514/195 |
| 4,717,722 | 1/1988 | Doherty et al. | 514/210 |
| 4,766,106 | 8/1988 | Katre et al. | 514/12 |
| 4,797,396 | 1/1989 | Finke et al. | 514/210 |
| 4,816,567 | 3/1989 | Cabilly et al. | 530/387 |
| 4,829,054 | 5/1989 | Emerson et al. | 514/21 |
| 4,923,807 | 5/1990 | Webb et al. | 435/69.2 |
| 4,968,614 | 11/1990 | Takiguchi et al. | 435/172.3 |
| 5,091,303 | 2/1992 | Arnaout et al. | 435/7.24 |
| 5,109,018 | 4/1992 | Powers et al. | 514/457 |
| 5,124,147 | 6/1992 | Wissner et al. | 424/85.8 |
| 5,128,258 | 7/1992 | Klostergaard et al. | 435/204.2 |
| 5,136,021 | 8/1992 | Dembinski et al. | 530/350 |
| 5,180,819 | 1/1993 | Cayre et al. | 536/23.2 |
| 5,200,333 | 4/1993 | Wilson | 435/172.3 |
| 5,247,070 | 9/1993 | Yamamada et al. | 530/351 |

FOREIGN PATENT DOCUMENTS

| | | |
|---|---|---|
| 2020700 | 2/1991 | Canada . |
| 0 146 026 A2 | 6/1985 | European Pat. Off. . |
| 0 148 311 A1 | 7/1985 | European Pat. Off. . |
| 0 155 549 A2 | 9/1985 | European Pat. Off. . |
| 0 158 286 A2 | 10/1985 | European Pat. Off. . |
| 0 168 214 A2 | 1/1986 | European Pat. Off. . |
| 0 171 496 B1 | 2/1986 | European Pat. Off. . |
| 0 174 204 A2 | 3/1986 | European Pat. Off. . |
| 0 260 610 B1 | 3/1988 | European Pat. Off. . |
| 0 268 110 A1 | 5/1988 | European Pat. Off. . |
| 0 270 799 A1 | 6/1988 | European Pat. Off. . |
| 0 288 088 B1 | 10/1988 | European Pat. Off. . |
| 0 308 378 B1 | 3/1989 | European Pat. Off. . |
| 0 395 254 A2 | 10/1990 | European Pat. Off. . |
| 0 398 327 B1 | 11/1990 | European Pat. Off. . |
| 62-100291 | 5/1987 | Japan . |
| 2 158 829 | 11/1985 | United Kingdom . |
| 2 177 096 | 1/1987 | United Kingdom . |
| 2 188 638 | 10/1987 | United Kingdom . |
| WO 91/02540 | 3/1991 | WIPO . |
| WO 91/09865 | 7/1991 | WIPO . |
| WO 92/00378 | 1/1992 | WIPO . |
| WO 93/07171 | 4/1993 | WIPO . |
| WO 93/16698 | 9/1993 | WIPO . |
| WO 94/00555 | 1/1994 | WIPO . |
| WO 95/02579 | 1/1995 | WIPO . |

OTHER PUBLICATIONS

Abstract, Dialog Accession No. 06706182, Medline Accession No. 89008182, Oshawa F. et al.: "Selective degradation of tumor necrosis factor in sensitive cells, and production of membrane–active substance"; and *J. Biochem.* (Tokyo) (Japan) (Apr. 1988) 103(4): 730–4.

Natanson et al. (1994) Annals of Internal Medicine. vol. 120(9): 771–783.

Fox et al. (1989) Clin. Chem. vol. 35(9):1838–1842.

Abrams et al., "Optimal Strategies for Developing Human–Human Monoclonal Antibodies," *Meth. Enzymol.*, 121:107–119 (1986).

Birnboim et al., "A Rapid Alkaline Extraction Procedure for Screening Recombinant Plasmid DNA," *Nucleic Acids Research*, 7:1513–1523 (1979).

Bories et al., "A Fertile Pair," *Cell*, 59:955–958 (Dec. 22, 1989).

Boss, B.D., "An Improved in Vitro Immunization Procedure for the Production of Monoclonal Antibodies," *Meth. Enzym.* 121:27–33 (1986).

Buck et al., "Monoclonal Antibodies Specific for Cell Culture Mycoplasmas," *In Vitro*, 18(4):377–381 (Apr., 1982).

Campanelli et al., "Cloning of cDNA for Proteinase 3: A Serine Protease, Antibiotic and Autoantigen from Human Neutrophils," *J. Exp. Med.*, 172:1709–1715 (Dec., 1990).

(List continued on next page.)

*Primary Examiner*—Christina Y. Chan
*Assistant Examiner*—Emma Cech
*Attorney, Agent, or Firm*—Donald J. Pochopien; Paul B. Savereide; Robert P. Blackburn

[57] ABSTRACT

Methods and materials are disclosed for the production of purified, active recombinant human neutrophil protease, PR-3, via activation of a pro-form herein referred to as proPR-3. Human PR-3 is useful for discovering inhibitors of excessive release of mature, active TNFα. Also disclosed are methods for the identification of inhibitors of the conversion of the pro-form of TNFα to its mature active form.

2 Claims, 11 Drawing Sheets

OTHER PUBLICATIONS

Cohen et al., "Nonchromosomal Antibiotic Resistance in Bacteria: Genetic Transformation of *Escherichia coli* by R–Factor DNA," *Proc. Nat'l. Acad. Sci., USA*, 69(8):2110–2114 (Aug., 1972).

Crawford et al., "Production of Human Monoclonal Antibody to X31 Influenza Virus Nucleoprotein," *J. of General Virology*, 64:697–700 (1983).

Croce et al., "Production of Human Hybridomas Secreting Antibodies to Measles Virus," *Nature*, 288:488–489 (1980).

Decker et al., "Cell–Associated Tumor Necrosis Factor (TNF) as a Killing Mechanism of Activated Cytotoxic Macrophages," *J. of Immunol.*,138(3):957–962 (Feb. 1, 1987).

Doherty et al., "Cephalosporin Antibodies Can Be Modified to Inhibit Human Leukocyte Elastase," *Nature*, 322:192–194 (Jul. 10, 1986).

Duff et al., "Tumor Necrosis Factor (TNF) and Interleukin 1 (IL 1) in Arthritis," *International Conference on Tumor Necrosis Factor and Related Cytotoxins*, 175:10 (1987).

Fendly, et al., "Murine Monoclonal Antibodies Defining Neutralizing Epitopes on Tumor Necrosis Factor," *Hybridoma*, 6(4):359–370 (1987).

Folks et al., "Tumor Necrosis Factor α Induces Expression of Human Immunodeficiency Virus in a Chronically Infected T–Cell Clone," *Proc. Nat'l Acad. Sci. USA*, 86:2365–2368 (Apr., 1989).

Graham et al., "A New Technique for the Assay of Infectivity of Human Adenovirus 5 DNA," *Virology*, 52:456–467 (1973).

Ish–Horowicz et al., "Rapid and Efficient Cosmid Cloning," *Nucleic Acids Res.*, 9(13):2989–2998 (1981).

Kam et al., "Substrate and Inhibitor Studies on Proteinase 3," *FEBS*, 297(1,2):119–123 (Feb., 1992).

Knauf et al., "Relationship of Effective Molecular Size to Systemic Clearance in Rats of Recombinant Interleukin–2 Chemically Modified with Water–soluble Polymers," *J. Biol. Chem.*, 263(29):15064–15070 (Oct. 15, 1988).

Kohler et al., "Continuous Cultures of Fused Cells Secreting Antibody of Predefined Specificity," *Nature*, 256:495–497 (Aug. 7, 1975).

Kozbor et al., "The Production of Monoclonal Antibodies From Human Lymphocytes," *J. Immun. Today*, 4(3):72–79 (1983).

Kramer et al., "Oligonucleotide–Directed Construction of Mutations via Gapped Duplex DNA," *Meth. Enzymol.*, 154:350–367 (1986).

Kriegler et al., "A Novel Form of TNF/Cachectin Is a Cell Surface Cytotoxic Transmembrane Protein: Ramifications for the Complex Physiology of TNF," *Cell*, 53:45–53 (Apr., 1988).

Kriegler et al., "Transformation Mediation by the SV40 T Antigens: Separation of the Overlapping SV40 Early Genes with a Retroviral Vector," *Cell*, 38:483–491 (Sep., 1984).

Larrick, J.W., "Plate Fusion Technique for Nonadherent Cells," *Human Hybridomas and Monoclonal Antibodies*, Engleman et al. (Eds.), Plenum Press, New York, pp. 446–448 (1985).

Luben et al., "In Vitro Immunization As An Adjunct to the Production of Hybridomas Producing Antibodies Against the Lymphokine Osteoclast Activating Factor," *Molecular Immunology*, 17:635–639 (1980).

Maki, D.G., "Nosocomial Bacteremia:An Expidemiologic Overview," *Nosocomical Infect.*, Dikson, R.E., (Ed.), Yrke Medical Books, USA, pp. 183–196 (1981).

Maniatis et al., *Molecular Cloning: A Laboratory Manual*, Cold Spring Harbor Laboratory, Cold Spring Harbor Press, pp. 254–255 (1982).

Matteucci et al., "Synthesis of Deoxyoligonucleotides on a Polymer Support," *J. Am. Chem. Soc.*, 103:3185–3191 (1981).

Maxam et al., "Sequencing End–Labeled DNA With Base–Specific Chemical Cleavages," *Meth. Enzymol.*, 65:499–560 (1980).

Merrifield, B., "Solid Phase Synthesis," *Science*, 232:341–347 (1986).

Messing et al., "A System for Shotgun DNA Sequencing," *Nucleic Acids Res.*, 9:309–321 (1981).

Navia et al., "Structure of Human Neutrophil Elastase in Complex With a Peptide Chloromethyl Ketone Inhibitor at 1.84–Å Resolution," *Proc. Nat'l Acad. Sci., USA*, 86:7–11 (1989).

Oleksyszyn et al., "Irreversible Inhibition of Serine Proteases by Peptide Derivatives of (α–Aminoalkyl)Phosphonate Diphenyl Esters," *Biochem.*, 30:485–493 (1991).

Rao et al., "Characterization of Proteinase–3 (PR–3), A Neutrophil Serine Proteinase," *J. Biol. Chem.*, 266:9540–9548 (1991).

Reading, C.L., "Theory and Methods for Immunization in Culture and Monoclonal Antibody Production,"*J. of Immun. Methods*, 53:261–291 (1982).

Reading, C.L., "In Vitro Immunization for the Production of Antigen–Specific Lymphocyte Hybridomas," *Meth. Enzym.*, 121:18–27 (1986).

Roder et al., "The EBV–Hybridoma Technique," *Meth. Enzym.*, 121:140–167 (1986).

Sanger et al., "DNA Sequencing With Chain–Terminating Inhibitors," *Proc. Nat'l Acad. Sci., USA*, 74:5463–5467 (1977).

Schlom et al., "Generation of Human Monoclonal Antibodies Reactive With Human Mammary Carcinoma Cells," *Proc. Nat'l Acad. Sci., USA*, 77:6841–6845 (1980).

Scuderi et al., "Cathepsin–G and Leukocytes Elastase Inactive Human Tumor Necrosis Factor and Lymphotoxin," *Cellular Immunol.*, 135:299–313 (1991).

Seckinger et al., "Purification and Biologic Characterization of a Specific Tumor Necrosis Factor α Inhibitor," *J. Biol. Chem.*, 264:11966–11973 (1989).

Seckinger et al., "A Human Inhibitor of Tumor Necrosis Factor α," *J. Exp. Med.*, 167:1511–1516 (1988).

Smith, M., "In Vitro Mutagenesis,"*Annual Review of Genetics*, 19:423–462 (1985).

Springer, T.A., "Cell–Surface Differentiation in the Mouse," *Monoclonal Antibodies*, Kennett et al., (Eds.), Plenum Press, New York, pp. 185–217 (1980).

Stetler et al., "Isolation and Sequence of a Human Gene Encoding a Potent Inhibitor of Leukocyte Proteases," *Nucleic Acids Research*, 14(20):7883–7896 (Oct. 24, 1986).

Tracey et al., "Anti–Cachetin/TNF Monoclonal Antibodies Prevent Septic Shock During Lethal Bacteriaemia," *Nature*, 330:662–664 (Dec. 17, 1987).

Wigler et al., "Biochemical Transfer of Single–Copy Eucaryotic Genes Using Total Cellular DNA as Donor," *Cell*, 14:725–731 (Jul., 1978).

Berger et al., "The Neutrophil Enzymes Proteinase 3 and Elastase Enhance the Production of IL–8 by Endothelial Cells in Culture," *Clin. Exp. Immunol.*, 101(Supplement 1):35 (1995) (Abstract 1).

Bini et al., "Antineutrohil Cytoplasm Autoantibodies in Wegener's Granulomatosis Recognize Conformational Epitopes on Proteinase 3," *J. of Immunol.*, 149(4):1409–1415 (Aug. 15, 1992).

Bone, R.C., "The Pathogenesis of Sepsis," *Annals of Internal Med.*, 115;457–469 (1991).

Brakch et al., "Processing Endoprotease Recognizes a Structural Feature at the Cleavage Site of Peptide Prohormones," *J. Biol. Chem.*,264(27):15912–15916 (Sep. 25, 1989).

Brown et al., "Dipeptidyl Peptidase I Is Enriched in Granules of in Vitro–and in Vivo–Activated Cytotoxic T Lymphocytes," *J. of Immunol.*, 150(11):4733–4742 (Jun. 1, 1993).

Buchan et al., "Interleukin–1 and Tumor Necrosis Factor mRNA Expression in Rheumatoid Arthritis: Prolonged of IL–1α," *Clin. Exp. Immunol.*, 73:449–455 (1988).

Buetler et al., "Cachectin and Tumor Necrosis Factor as Two Sides of the Same Biological Coin," *Nature*, 320:584–588 (Apr. 17, 1986).

Caputo et al., "Activation of Recombinant Murine Cytotoxic Cell Proteinase–1 Requires Deletion of an Amino–terminal Dipeptide," *J. of Biol. Chem.*, 268(24):17672–17675 (Aug. 25, 1993).

Carswell et al., "An Endotoxin–Induced Serum Factor That Causes Necrosis of Tumors," *Proc. Nat'l Acad. Sci., USA*, 72(9):3666–3670 (Sep., 1975).

Castro et al., "1993 Revised Classification System for HIV Infection and Expanded Surveillance Case Definition for AIDS Among Adolescents and Adults," *Morbid. Mortal. Wk. Rep.*, 41(RR–17):1–19 (Dec. 18, 1993).

Chang et al., "Epitope Mapping of Anti–Proteinase 3 and Anti–Myeloperoxidase Antibodies," *Clin. Exp. Immunol.*, 102:112–119 (1995).

Chang et al., "B Cell Epitope Mapping of Anti–Proteinase 3 and Anti–Myeloperoxidase Antibodies," *Clin. Exp. Immunol.*, 101:51 (1995) (Abstract 66).

Chu et al., "Localization of Tumor Necrosis Factor α in Synovial Tissues and at the Cartilage–Pannus Junction in Patients with Rheumatoid Arthritis," *Arthritis and Rheumatism*, 34(9):1125–1131 (Sep., 1991).

Dalboge et al., "A Novel Enymatic Method for Production of Authentic hGH from an *Escherichia Coli* Produced hGH–Precursor," *Bio/Technology*, 5:161–164 (Feb., 1987).

Dalpé et al., "The Conformational Determinants Recognized by Wegener's C–ANCAS are Situated at or Near the Catalytic Domain of Myeloblastin," *Clin. Exp. Immunol.*, 93:21 (1993) (Abstract 19).

DeStefano et al., "Acid–Labile Human Leukocyte Interferon in Homosexual Men with Kaposi's Sarcoma and Lymphadenopathy," *J. Inf. Dis.*, 146(4):451–455 (Oct., 1982).

Dezube et al., "Pentoxifylline Decreases Tumor Necrosis Factor Expression and Serum Triglycerides in People With AIDS," *J. Acq. Immune Def. Syndrome*, 6:787–794 (1993).

Di Marco et al., "Purification, Analysis and Enzymatic Activity of Recombinant Human Synovial Fluid Phospholipase $A_2$ and N–Terminal Variants," *J. Biochem.*, 112:350–354 (1992).

Duffaud et al., "Signal Peptidases Recognize a Structural Feature at the Cleavage Site of Secretory Proteins," *J. Biol. Chem.*, 263(21):10224–10228 (Jul. 25, 1988).

Duh et al., "Tumor Necrosis Factor α Activates Human Immunodeficiency Virus Type 1 Through Induction of Nuclear Factor Binding to the NF–kB Sites in the Long Terminal Repeat," *Proc. Nat'l Acad. Sci., USA*, 86:5974–5978 (Aug., 1989).

Eyster et al., "Acid–Labile Alpha Interferon: A Possible Preclinical Marker for the Acquired Immunodeficiency Syndrome in Hemophilia," *N. Eng. J. Med.*, 309(10):583–586 (1983).

Fazely et al., "Pentoxyiflline (Trental) Decreases the Replication of the Human Immunodeficiency Virus Type I in Human Peripheral Blood Mononuclear Cells and in Cultured T Cells," *Blood*, 77(8):1653–1656 (Apr. 15, 1991).

Fiers, W., "Tumor Necrosis Factor: Characterization at the Molecular, Cellular and In Vivo Level," *FEB 09976*, 285(2):199–212 (Jul., 1991).

Gabay et al., "Antibiotic Proteins of Human Polymorphonuclear Leukocytes," *Proc Nat'l Acad, Sci, USA*, 86:5610–5614 (Jul., 1989).

Goodwin et al., "Molecular and Biological Characterization of a Ligand for CD27 Defines a New Family of Cytokines with Homology to Tumor Necrosis Factor," *Cell*, 73:447–456 (May 7, 1993).

Graf et al., "Cloning of TRAP, a Ligand for CD40 on Human T Cells," *Eur. J. Immunol.*, 22:3191–3194 (1992).

Gupta et al., "Identity of Wegener's Autoantigen (P29) with Proteinase 3 and Myeloblastin," *Blood*, 76(10:2162 (Nov. 15, 1990).

Hagen, E.C., "Standardisation of ANCA Assays Using Purified Proteinase–3 (PR–3) and Myeloperoxidase (MPO)," *Clin. Exp. Immunol.*, 101:41 (1995) (Abstract 27).

Hinshaw et al., "Survival of Primates in $LD_{100}$ Septic Shock Following Therapy With Antibody to Tumor Necrosis Factor (TNFα)," *Circulatory Shock*, 30;279–292 (1989).

Henshaw et al., "Elevations of Neutrophil Proteinase 3 In Serum of Patients with Wegener's Granulomatosis and Polyarteritis Nodosa," *Arthritis and Rheumatism*, 37(1):104–112 (1994).

Howard et al., "Soluble Tumor Necrosis Factor Receptor: Inhibition of Human Immunodeficiency Virus Activation," *Proc. Nat'l Acad. Sci., USA*, 90:2335–2339 (Mar., 1993).

Huang et al., "Epitope Mapping on the Proteinase 3 Molecule Using Monoclonal Antibodies and Sera From Patients with Wegener's Granulomatosis," *Clin. Exp. Immunol.*, 101:50 (1995) (Abstract 64).

Ito et al., "Tumor Necrosis Factor Antagonizes Inhibitory Effect of Azidothymidine on Human Immunodeficiency Virus (HIV) Replication In Vitro," *Bioch. Biophys. Res. Comm.*, 166(3):1095–1101 (Feb. 14, 1990).

Jarvis et al., "Influence of Different Signal Peptides and Prosequences on Expression and Secretion of Human Tissue Plasminogen Activator in the Baculovirus System," *J. Biol. Chem.*, 268(22):16754–16762 (Aug. 5, 1993).

Jennette and Falk, "Clinical and Pathological Classification of ANCA–associated Vasculitis: What Are the Controversies?," *Clin. Exp. Immunol.*, 101:18–21 (1995).

Jennings et al., "Anti–Poteinase 3 Antibodies, Their Characterization and Disease Associations," *Clin. Exp. Immunol.*, 95:251–256 (1994).

Kallenberg et al., "Antineutrophil Cytoplasmic Antibodies: A Still–Growing Class of Autoantibodies in Inflammatory Disorders," *Am. J. of Med.*, 93;675–682 (Dec., 1992).

Kallenberg et al., "ELISA for the Detection of Antibodies Against Neutrophil Cytoplasm Antigens," *Techniques in Diagnostic Pathology*, 2:49–60 (1991).

Kamijo et al., "Induction of Differentiation of Human Monoblastic and Myoblastic leukemia all lines by TNF Muteins," *Biochem. Biophys. Res. Comm.*, 160(2):820–827 (APr. 28, 1989).

Kao et al., "Proteinase 3: A Distinct Human Polymorphonuclear Leukocyte Proteinase that Products Emphysema in Hamsters," *J. Clin. Invest.*, 82:1963–1973 (Dec., 1988).

Kitts et al., "Linearization of Baculovirus DNA Enhances the Recovery of Recombinant Virus Expression Vectors", *Nucleic Acids Res.*, 18(19):5667–5672 (1990).

Kriegler et al., "Gene Transfer and Expression," Stockton Press, pp. 99–100, 114–135 (1990).

Lähdevirta et al., "Elevated Levels of Circulating Cachetin/Tumor Necrosis Factor in Patients with acquired Immunodeficiency Syndrome," *Am. J. Med.*, 85:289–291 (Sep., 1988).

Lau et al., "Regulation of Tumor Necrosis Factor Receptor Expression by Acid–Labile Interferon–α from AIDS Sera," *AIDS Res. Hum. Retroviruses*, 7(6):545–552 (1991).

Lau and Livesay, "Endotoxin Induction of Tumor Necrosis Factor Is Enhanced by Acid–labile Interferon–α in Acquired Immunodeficiency Syndrome," *J. Clin. Invest.*, 84:738–743 (Sep., 1989).

Lawton et al., "Anti–Proteinase 3 Antibody in Hong Kong Chinese," *Clin. Exp. Immunol.*, 101:72 (1995) (Abstract 152).

Lebouille et al., "Properties of a Leu–Phe–Cleaving Endopeptidase Activity Putatively Involved in β–Endorphin Metabolism in Rat Brain," *J. Neurochem.*, 52:1714–1721 (1989).

Leid et al., "Cleavage and Inactivation of Human C1–Inhibitor by the Human Leukocyte Proteinase, Proteinase 3," *Clin. Exp. Immunol.* 93:24 (1993).

Luben and Mohler, "In Vitro Immunization as an Adjunct to the Production of Hybridomas Producing Antibodies Against the Lymphokine Osteoclast Activating Factor," *Molecular Immunology*, 121:635–639 (1980).

Lüdemann et al., "Anti–Neutrophil Cytoplasm Antibodies in Wegener's Granulomatosis Recognize an Elastinolytic Enzyme," *J. Exp. Med.*, 171:357–362 (Jan., 1990).

Lüdemann et al., "Detection and Quantitation of Anti–Neutrophil Cytoplasm Antibodies in Wegener's Granulomatosis by ELISA Using Affinity–Purified Antigen," *J. Immun. Meth.*, 114:167–174 (1988).

Maiorella et al., "Large–Scale Insect Cell–Culture for Recombinant Protein Production," *Bio/Technology*, 6:1406–1410 (Dec., 1988).

Marks et al., "Enkephalin Analogs as Substrates for the Assay of Brain Cysteine Proteinase (Cathespin L) and its Endogenous Inhibitors," *Peptides*, 10:391–394 (1989).

McGuire et al., "Generation of Active Myeloid and Lymphoid Granule Serine Proteases Requires Processing of the Granule Thiol Protease Dipeptidyl Peptidase I," *J. Biol. Chem.*, 268(4):2458–2467 (Feb. 5, 1993).

Merril et al., "Interleukin–1 and Tumor Necrosis Factor α Can be Induced from Mononuclear Phagocytes by Human Immunodeficiency Virus Type 1 Binding to the CD4 Receptor," *J. Virol.*, 63(10);4404–4408 (Oct., 1989).

Mohler et al., "Protection Against a Lethal Dose of Endotoxin by an Inhibitor of Tumour Necrosis Factor Processing," *Nature*, 370:218–220 (Jul. 21, 1994).

Mullis et al., "Specific Enzymatic Amplification of DNA In Vitro: The Polymerase Chain Reaction," *Cold Spring Harbor Symposium Quant. Biol., Cold Spring Harbor Laboratory*, vol. LI, pp. 263–273 (1986).

Müller et al., "Synthesis and maturation of recombinant human tumor necrosis factor in eukaryotic systems," *FEBS* 3424, 197(1,2):99–104 (Mar., 1986).

Muller–Bérat et al., "The Phylogeny of Proteinase 3/Myeloblastin, and Myeloperoxidase as Shown by Immunohistochemical Studies on Human Leukemic Cell Lines," *Clin. Exp. Immunol.*, 93:24 (1993) (Abstract 31).

Munemitsu et al., "Molecular Cloning and Expression of a G25K cDNA, the Human Homolog of the Yeast Cell Cycle Gene CDC42," *Mol. Cell. Biol.*, 10(11);5977–5982 (Nov., 1988).

Niles et al., "Wegener's Granulomatosis Autoantigen is a Novel Neutrophil serine Proteinase," *Blood*, 74(6):1888–1893 (Nov. 1, 1989).

Nowotny et al., "Preparation and Activity Measurements of Deuterated 50S Subunits for Neuron–Scattering Analysis," *Methods in Enzymology*, 164:131–147 (1988).

Olsen et al., "High–Efficiency Oligonucleotide–Directed Plasmid Mutagenesis," *Proc. Nat'l Acad. Sci., USA*, 87:1451–1455 (Feb., 1990).

Poli et al., "Tumor Necrosis Factor α Functions in an Autocrine Manner in the Induction of Human Immunodeficiency Virus Expression," *Proc. Nat'l Acad. Sci., USA*, 87:782–785 (Jan., 1990).

Robache–Gallea et al., "In Vitro Processing of Human Tumor Necrosis Factor–α," *J. Biol. Chem.*, 270(40);23688–23692 (Oct. 6, 1995).

Salvesen et al., "An Unusual Specificity in the Activation of Neutrophil Serine Proteinase Zymogens," *Biochem.*, 29:5304–5308 (1990).

Salvesen et al., "Zymogen Activation Specificity and Genomic Structure of Human Neutrophil Elastase and Cathepsin G Reveal a New Branch of the Chymotrypsinogen Superfamily of Serine Proteinases," *Biomed. Biochim. Acta*, 50:665–671 (1991).

Savige et al., "Anti–Neutrophil Cytoplasmic Antibodies (ANCA): Their Detection and Significance: Report from Workshops," *Pathology*, 26:186–193 (1994).

Seckinger et al., "A Human Inhibitor of Tumor Necrosis Factor α," *J. Exp. Med.* 167:1511–1516 (Apr., 1988).

Smith et al., "Production of Human Beta Interferon in Insect Cells Infected with a Baculovirus Expression Vector," *Mol. Cell. Biol.*, 3(12)2156–2165 (Dec., 1983).

Streiter et al., "Cellular and Molecular Regulation of Tumor Necrosis Factor–Alpha Production by Pentoxifylline," *Bioch. Biophys. Res. Comm.*, 155(3):1230–1236 (Sep. 30, 1988).

Sturrock et al., "Structure, Chromosomal Assignment, and Expression of the Gene for Proteinase–3," *J. Biol. Chem.*, 267(29):21193–21199 (Oct. 15, 1992).

Summers and Smith, A Manual of Methods for Baculovirus Vectors and Insect Cell Culture Procedures, *Texas Agrigultural Experiment Station, Bulletin No. 1555*, pp. 1–56 (May, 1987).

Takahashi et al., "Structure of the Human Neutrophil Elastase Gene," *J. Biol. Chem.*, 263(29):14739–14747 (Oct. 15, 1988).

Takebe et al., "SRα Promoter: an Efficient and Versatile Mammalian cDNA Expression System Composed of the Simian Virus 40 Early Promoter and the R–U5 Segment of Human T–Cell Leukemia Virus Type 1 Long Terminal Repeat," *Mol. Cell Biol.*, 8(1):466–472 (Jan., 1988).

Urata et al., "Dipeptide Processing Activates Recombinant Human Prochymase," *J. Biol. Chem.*, 268(32):24318–24322 (Nov., 15, 1993).

White and Littman, "Viral Receptors of the Immunoglobulin Superfamily," *Cell*, 56:725–728 (Mar. 10, 1989).

Williams et al., "Epitope on Proteinase–3 Recognized by Antibodies from Patients with Wegener's Granulomatosis," *J. of Immunol.*, 152:4722–4737 (1994).

Williams et al., "Septic shock: the continuing challenge for an effective therapy," *Exp. Opin. Invest. Drugs*, 3(10):1051–1056 (1994).

Witko–Sarsat et al., "Expression of Recombinant Proteinase 3—Implication for its Role as Autoantigen," *Clin. Exp. Immunol.*, 101:40 (1994) (Abtract 23).

Zimmer et al., "Three Human Elastase–Like Genes Corrdinately Expressed in the Myelomonocyte Lineage are Organized as a Small Genetic Locus on 19pter," *Proc. Nat'l Acad. Sci., USA*, 89:8215–8219 (Sep., 1992).

-76
| ATG | AGC | ACT | GAA | AGC | ATG | ATC | CGG | GAC | GTG | GAG | CTG |
| Met | Ser | Thr | Glu | Ser | Met | Ile | Arg | Asp | Val | Glu | Leu |

GCC GAG GAG GCG CTC CCC AAG AAG ACA GGG GGG CCC
Ala Glu Glu Ala Leu Pro Lys Lys Thr Gly Gly Pro

CAG GGC TCC AGG CGG TGC TTG TTC CTC AGC CTC TTC
Gln Gly Ser Arg Arg Cys Leu Phe Lue Ser Leu Phe

TCC TTC CTG ATC GTG GCA GGC GCC ACC ACG CTC TTC
Ser Phe Leu Ile Val Ala Gly Ala Thr Thr Leu Phe

TGC CTG CTG CAC TTT GGA GTG ATC GGC CCC CAG AGG
Cys Leu Leu His Phe Gly Val Ile Gly Pro Gln Arg

GAA GAG TCC CCC AGG GAC CTC TCT CTA ATC AGC CCT
Glu Glu Ser Pro Arg Asp Leu Ser Leu Ile Ser Pro

CTG GCC CAG GCA▼GTC AGA TCA TCT TCT CGA ACC CCG
Leu Ala Gln Ala Val Arg Ser Ser Ser Arg Thr Pro

AGT GAC AAG CCT GTA GCC CAT GTT GTA GCA AAC CCT
Ser Asp Lys Pro Val Ala His Val Val Ala Asn Pro

CAA GCT GAG GGG CAG CTC CAG TGG CTG AAC CGC CGG
Gln Ala Glu Gly Gln Leu Gln Trp Leu Asn Arg Arg

GCC AAT GCC CTC CTG GCC AAT GGC GTG GAG CTG AGA
Ala Asn Ala Leu Leu Ala Asn Gly Val Glu Leu Arg

GAT AAC CAG CTG GTG GTG CCA TCA GAG GGC CTG TAC
Asp Asn Gln Leu Val Val Pro Ser Glu Gly Leu Tyr

CTC ATC TAC TCC CAG GTC CTC TTC AAG GGC CAA GGC
Leu Ile Tyr Ser Gln Val Leu Phe Lys Gly Gln Gly

TGC CCC TCC ACC CAT GTG CTC CTC ACC CAC ACC ATC
Cys Pro Ser Thr His Val Leu Leu Thr His Thr Ile

AGC CGC ATC GCC GTC TCC TAC CAG ACC AAG GTC AAC
Ser Arg Ile Ala Val Ser Tyr Gln Thr Lys Val Asn

CTC CTC TCT GCC ATC AAG AGC CCC TGC CAG AGG GAG
Leu Leu Ser Ala Ile Lys Ser Pro Cys Gln Arg Glu

ACC CCA GAG GGG GCT GAG GCC AAG CCC TGG TAT GAG
Thr Pro Glu Gly Ala Glu Ala Lys Pro Trp Tyr Glu

CCC ATC TAT CTG GGA GGG GTC TTC CAG CTG GAG AAG
Pro Ile Tyr Leu Gly Gly Val Phe Gln Leu Glu Lys

GGT GAC CGA CTC AGC GCT GAG ATC AAT CGG CCC GAC
Gly Asp Arg Leu Ser Ala Glu Ile Asn Arg Pro Asp

TAT CTC GAC TTT GCC GAG TCT GGG CAG GTC TAC TTT
Tyr Leu Asp Phe Ala Glu Ser Gly Gln Val Tyr Phe
                    157
GGG ATC ATT GCC CTG
Gly Ile Ile Ala Leu

FIG. 1C

```
1       /    1                                                      31    /    11
ATG GCT CAC CGG CCC CCC AGC CCT GCC CTG GCG TCC GTG CTG CTG GCC TTG CTG CTG
MET ALA HIS ARG PRO PRO SER PRO ALA LEU ALA SER VAL LEU LEU ALA LEU LEU LEU

61    /    21                                              91    /    31
AGC GGT GCT GCC CGA GCT GCG GAG ATC GTG GGC GGG CAC GAG GCG CAG CCA CAC TCC
SER GLY ALA ALA ARG ALA ALA GLU ILE VAL GLY GLY HIS GLU ALA GLN PRO HIS SER

121   /    41                                          151   /    51
CGG CCC TAC ATG GCC TCC CTG CAG ATG CGG GGG AAC CCG GGC AGC CAC TTC TGC GGA
ARG PRO TYR MET ALA SER LEU GLN MET ARG GLY ASN PRO GLY SER HIS PHE CYS GLY

181   /    61                                          211   /    71
GGC ACC TTG ATC CAC CCC AGC TTC GTG CTG ACG GCC GCG CAC TGC CTG CGG GAC ATA
GLY THR LEU ILE HIS PRO SER PHE VAL LEU THR ALA ALA HIS CYS LEU ARG ASP ILE

241   /    81                                          271   /    91
CCC CAG CGC CTG GTG AAC GTG GTG CTC GGA GCC CAC AAC GTG CGG ACG CAG GAG CCC
PRO GLN ARG LEU VAL ASN VAL VAL LEU GLY ALA HIS ASN VAL ARG THR GLN GLU PRO
```

FIG. 2A

```
ACC CAG CAG CAC TTC   301 /  101
                      TCG GTG GCT CAG GTG TTT CTG AAC AAC TAC   331 /  111
THR GLN GLN HIS PHE   SER VAL ALA GLN VAL PHE LEU ASN ASN TYR   GAC GCG GAG AAC
                                                                ASP ALA GLU ASN

AAA CTG AAC GAC ATT   361 /  121
                      CTC CTC ATC CAG CTG AGC AGC CCA GCC AAC   391 /  131
LYS LEU ASN ASP ILE   LEU LEU ILE GLN LEU SER SER PRO ALA ASN   CTC AGT GCC TCC
                                                                LEU SER ALA SER

GTC GCC ACA GTC CAG   421 /  141
                      CAG CAG GAC CAG CCA GTG CCC CAC GGC ACC   451 /
VAL ALA THR VAL GLN   GLN GLN ASP GLN PRO VAL PRO HIS GLY THR   CAG TGC
                                                                GLN CYS

151
CTG GCC ATG GGC GGC   481 /  161
                      TGG GGC CGC GTG GCC CAC GAC CCC CCA GCC   511
LEU ALA MET GLY GLY   TRP GLY ARG VAL ALA HIS ASP PRO PRO ALA   CAG GTC CTG CAG
                                                                GLN VAL LEU GLN

/   171
GAG CTC AAT GTC ACC   541 /  181
                      GTG GTC ACC TTC TGC CCA CAT AAC ATT TGC   ACT TTC
GLU LEU ASN VAL THR   VAL VAL THR PHE CYS PRO HIS ASN ILE CYS   THR PHE
```

FIG. 2B

```
571  /  191
GTC CCT CGC AAG GCC GGC ATC TGC TTC       601  /  201
VAL PRO ARG ARG LYS ALA GLY ILE CYS PHE   GGA GAC TCA GGT GGC CCC CTG ATC TGT
                                          GLY ASP SER GLY GLY PRO LEU ILE CYS

631  /  211
GGC ATC ATC CAA GGA ATA GAC TCC TTC       661  /  221
GLY ILE ILE GLN GLY ILE ASP SER PHE       GTG ATC TGG GGA TGT GCC ACC CGC CTT
GAT                                       VAL ILE TRP GLY CYS ALA THR ARG LEU
ASP

691  /  231
TTC GAC TTC ACG CGG GTA GCC CTC TAC       721  /  241
PHE ASP PHE THR ARG VAL ALA LEU TYR       GTG GAC TGG ATC CGT TCC ACG CTG
TTC CCT                                   VAL ASP TRP ILE ARG SER THR LEU
PHE PRO

751  /  251
GAG GCC AAG GGC CGC CCC TGA
GLU ALA LYS GLY ARG PRO OPA
CGC CGT GTG
ARG ARG VAL
```

FIG. 2C

FIG. 3A    A B C D
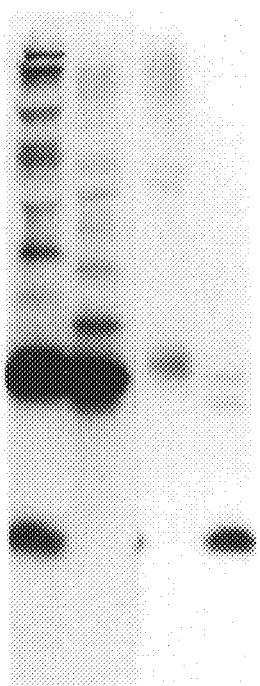
26 kD —
17 kD —
FIG. 3B    A  B C D E F
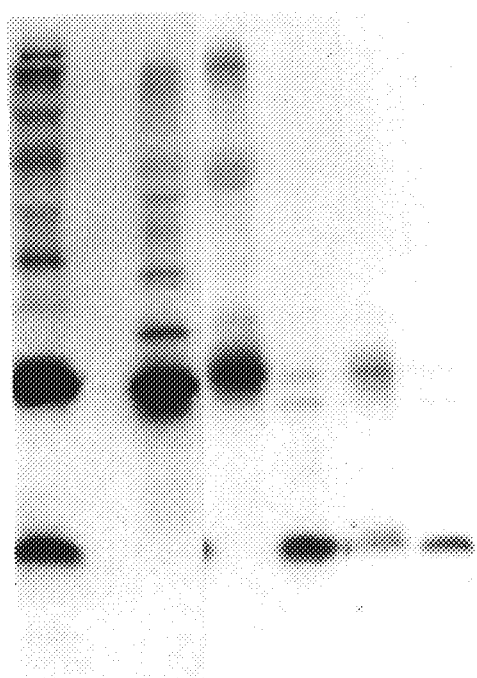
26 kD —
17 kD —

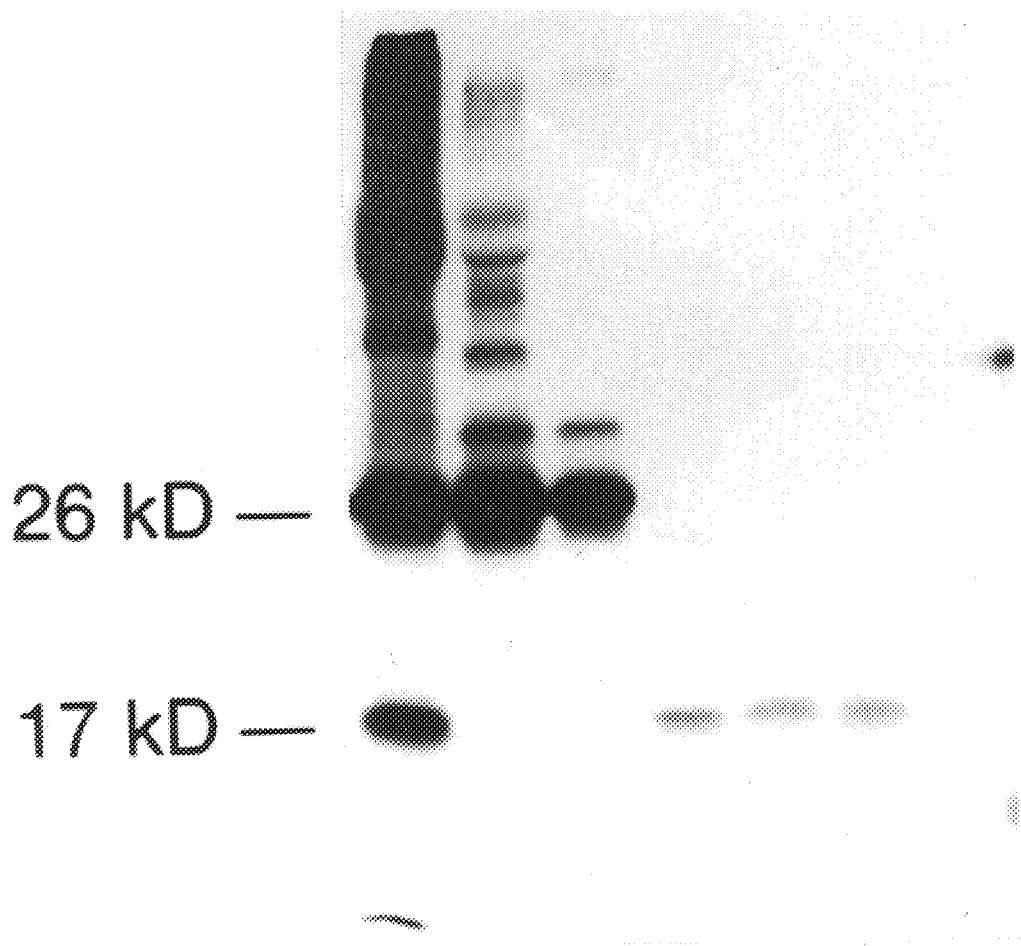

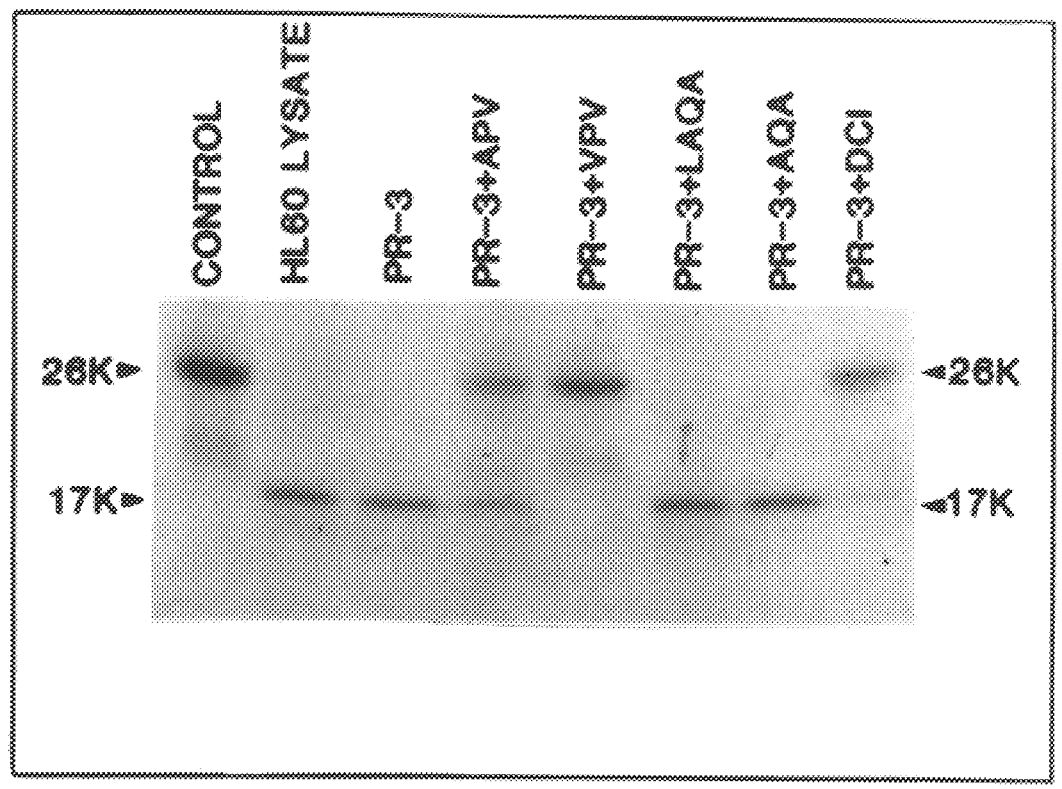
FIG. 6A
FIG. 6B
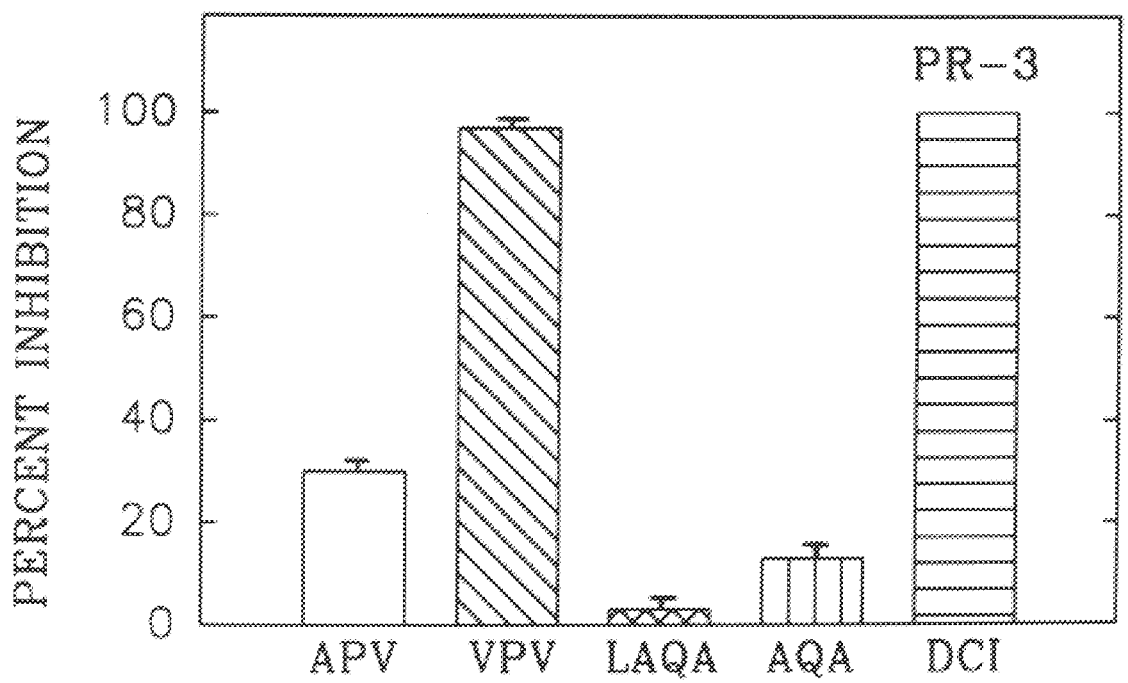

Hours After LPS Injection

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 699 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..699

( i x ) FEATURE:
        ( A ) NAME/KEY: mat_peptide
        ( B ) LOCATION: 229..699

( x i ) SEQUENCE DESCRIPTION: SEQ ID NO:1:

```
ATG  AGC  ACT  GAA  AGC  ATG  ATC  CGG  GAC  GTG  GAG  CTG  GCC  GAG  GAG  GCG        48
Met  Ser  Thr  Glu  Ser  Met  Ile  Arg  Asp  Val  Glu  Leu  Ala  Glu  Glu  Ala
-76  -75            -70                           -65

CTC  CCC  AAG  AAG  ACA  GGG  GGG  CCC  CAG  GGC  TCC  AGG  CGG  TGC  TTG  TTC        96
Leu  Pro  Lys  Lys  Thr  Gly  Gly  Pro  Gln  Gly  Ser  Arg  Arg  Cys  Leu  Phe
-60            -55                      -50                           -45

CTC  AGC  CTC  TTC  TCC  TTC  CTG  ATC  GTG  GCA  GGC  GCC  ACC  ACG  CTC  TTC       144
```

|     |     |     |     |     |     |     |     |     |     |     |     |     |     |     |     |     |
|---|---|---|---|---|---|---|---|---|---|---|---|---|---|---|---|---|
| Leu | Ser | Leu | Phe | Ser<br>-40 | Phe | Leu | Ile | Val | Ala<br>-35 | Gly | Ala | Thr | Thr | Leu<br>-30 | Phe | |
| TGC<br>Cys | CTG<br>Leu | CTG<br>Leu | CAC<br>His<br>-25 | TTT<br>Phe | GGA<br>Gly | GTG<br>Val | ATC<br>Ile | GGC<br>Gly<br>-20 | CCC<br>Pro | CAG<br>Gln | AGG<br>Arg | GAA<br>Glu | GAG<br>Glu<br>-15 | TCC<br>Ser | CCC<br>Pro | 192 |
| AGG<br>Arg | GAC<br>Asp | CTC<br>Leu<br>-10 | TCT<br>Ser | CTA<br>Leu | ATC<br>Ile | AGC<br>Ser | CCT<br>Pro<br>-5 | CTG<br>Leu | GCC<br>Ala | CAG<br>Gln | GCA<br>Ala | GTC<br>Val | AGA<br>Arg<br>1 | TCA<br>Ser | TCT<br>Ser | 240 |
| TCT<br>Ser<br>5 | CGA<br>Arg | ACC<br>Thr | CCG<br>Pro | AGT<br>Ser | GAC<br>Asp<br>10 | AAG<br>Lys | CCT<br>Pro | GTA<br>Val | GCC<br>Ala | CAT<br>His<br>15 | GTT<br>Val | GTA<br>Val | GCA<br>Ala | AAC<br>Asn | CCT<br>Pro<br>20 | 288 |
| CAA<br>Gln | GCT<br>Ala | GAG<br>Glu | GGG<br>Gly | CAG<br>Gln<br>25 | CTC<br>Leu | CAG<br>Gln | TGG<br>Trp | CTG<br>Leu | AAC<br>Asn<br>30 | CGC<br>Arg | CGG<br>Arg | GCC<br>Ala | AAT<br>Asn | GCC<br>Ala<br>35 | CTC<br>Leu | 336 |
| CTG<br>Leu | GCC<br>Ala | AAT<br>Asn | GGC<br>Gly<br>40 | GTG<br>Val | GAG<br>Glu | CTG<br>Leu | AGA<br>Arg | GAT<br>Asp<br>45 | AAC<br>Asn | CAG<br>Gln | CTG<br>Leu | GTG<br>Val | GTG<br>Val<br>50 | CCA<br>Pro | TCA<br>Ser | 384 |
| GAG<br>Glu | GGC<br>Gly | CTG<br>Leu<br>55 | TAC<br>Tyr | CTC<br>Leu | ATC<br>Ile | TAC<br>Tyr | TCC<br>Ser<br>60 | CAG<br>Gln | GTC<br>Val | CTC<br>Leu | TTC<br>Phe | AAG<br>Lys<br>65 | GGC<br>Gly | CAA<br>Gln | GGC<br>Gly | 432 |
| TGC<br>Cys | CCC<br>Pro<br>70 | TCC<br>Ser | ACC<br>Thr | CAT<br>His | GTG<br>Val | CTC<br>Leu<br>75 | CTC<br>Leu | ACC<br>Thr | CAC<br>His | ACC<br>Thr | ATC<br>Ile<br>80 | AGC<br>Ser | CGC<br>Arg | ATC<br>Ile | GCC<br>Ala | 480 |
| GTC<br>Val<br>85 | TCC<br>Ser | TAC<br>Tyr | CAG<br>Gln | ACC<br>Thr | AAG<br>Lys<br>90 | GTC<br>Val | AAC<br>Asn | CTC<br>Leu | CTC<br>Leu | TCT<br>Ser<br>95 | GCC<br>Ala | ATC<br>Ile | AAG<br>Lys | AGC<br>Ser | CCC<br>Pro<br>100 | 528 |
| TGC<br>Cys | CAG<br>Gln | AGG<br>Arg | GAG<br>Glu | ACC<br>Thr<br>105 | CCA<br>Pro | GAG<br>Glu | GGG<br>Gly | GCT<br>Ala | GAG<br>Glu<br>110 | GCC<br>Ala | AAG<br>Lys | CCC<br>Pro | TGG<br>Trp | TAT<br>Tyr<br>115 | GAG<br>Glu | 576 |
| CCC<br>Pro | ATC<br>Ile | TAT<br>Tyr | CTG<br>Leu<br>120 | GGA<br>Gly | GGG<br>Gly | GTC<br>Val | TTC<br>Phe | CAG<br>Gln<br>125 | CTG<br>Leu | GAG<br>Glu | AAG<br>Lys | GGT<br>Gly | GAC<br>Asp<br>130 | CGA<br>Arg | CTC<br>Leu | 624 |
| AGC<br>Ser | GCT<br>Ala | GAG<br>Glu<br>135 | ATC<br>Ile | AAT<br>Asn | CGG<br>Arg | CCC<br>Pro | GAC<br>Asp<br>140 | TAT<br>Tyr | CTC<br>Leu | GAC<br>Asp | TTT<br>Phe | GCC<br>Ala<br>145 | GAG<br>Glu | TCT<br>Ser | GGG<br>Gly | 672 |
| CAG<br>Gln | GTC<br>Val<br>150 | TAC<br>Tyr | TTT<br>Phe | GGG<br>Gly | ATC<br>Ile | ATT<br>Ile<br>155 | GCC<br>Ala | CTG<br>Leu | | | | | | | | 699 |

( 2 ) INFORMATION FOR SEQ ID NO:2:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|     |     |     |     |     |     |     |     |     |     |     |     |     |     |
|---|---|---|---|---|---|---|---|---|---|---|---|---|---|
| Met<br>-76 | Ser<br>-75 | Thr | Glu | Ser | Met<br>-70 | Ile | Arg | Asp | Val | Glu<br>-65 | Leu | Ala | Glu | Glu | Ala |
| Leu<br>-60 | Pro | Lys | Lys | Thr<br>-55 | Gly | Gly | Pro | Gln | Gly<br>-50 | Ser | Arg | Arg | Cys | Leu<br>-45 | Phe |
| Leu | Ser | Leu | Phe | Ser<br>-40 | Phe | Leu | Ile | Val | Ala<br>-35 | Gly | Ala | Thr | Thr | Leu<br>-30 | Phe |
| Cys | Leu | Leu | His | Phe | Gly | Val | Ile | | | | | | | | |

( 2 ) INFORMATION FOR SEQ ID NO:3:

( i ) SEQUENCE CHARACTERISTICS:
        ( A ) LENGTH: 771 base pairs
        ( B ) TYPE: nucleic acid (C) STRANDEDNESS: single
(D) TOPOLOGY: linear (ii) MOLECULE TYPE: cDNA (ix) FEATURE:
(A) NAME/KEY: CDS
(B) LOCATION: 1..771

(xi) SEQUENCE DESCRIPTION: SEQ ID NO:3:

| ATG | GCT | CAC | CGG | CCC | CCC | AGC | CCT | GCC | CTG | GCG | TCC | GTG | CTG | CTG | GCC | 48 |
| Met | Ala | His | Arg | Pro | Pro | Ser | Pro | Ala | Leu | Ala | Ser | Val | Leu | Leu | Ala | |
| 1 | | | | 5 | | | | | 10 | | | | | 15 | | |

| TTG | CTG | CTG | AGC | GGT | GCT | GCC | CGA | GCT | GCG | GAG | ATC | GTG | GGC | GGG | CAC | 96 |
| Leu | Leu | Leu | Ser | Gly | Ala | Ala | Arg | Ala | Ala | Glu | Ile | Val | Gly | Gly | His | |
| | | | 20 | | | | | 25 | | | | | 30 | | | |

| GAG | GCG | CAG | CCA | CAC | TCC | CGG | CCC | TAC | ATG | GCC | TCC | CTG | CAG | ATG | CGG | 144 |
| Glu | Ala | Gln | Pro | His | Ser | Arg | Pro | Tyr | Met | Ala | Ser | Leu | Gln | Met | Arg | |
| | | 35 | | | | | 40 | | | | | 45 | | | | |

| GGG | AAC | CCG | GGC | AGC | CAC | TTC | TGC | GGA | GGC | ACC | TTG | ATC | CAC | CCC | AGC | 192 |
| Gly | Asn | Pro | Gly | Ser | His | Phe | Cys | Gly | Gly | Thr | Leu | Ile | His | Pro | Ser | |
| | 50 | | | | | 55 | | | | | 60 | | | | | |

| TTC | GTG | CTG | ACG | GCC | GCG | CAC | TGC | CTG | CGG | GAC | ATA | CCC | AGC | CGC | CTG | 240 |
| Phe | Val | Leu | Thr | Ala | Ala | His | Cys | Leu | Arg | Asp | Ile | Pro | Gln | Arg | Leu | |
| 65 | | | | | 70 | | | | | 75 | | | | | 80 | |

| GTG | AAC | GTG | GTG | CTC | GGA | GCC | CAC | AAC | GTG | CGG | ACG | CAG | GAG | CCC | ACC | 288 |
| Val | Asn | Val | Val | Leu | Gly | Ala | His | Asn | Val | Arg | Thr | Gln | Glu | Pro | Thr | |
| | | | | 85 | | | | | 90 | | | | | 95 | | |

| CAG | CAG | CAC | TTC | TCG | GTG | GCT | CAG | GTG | TTT | CTG | AAC | AAC | TAC | GAC | GCG | 336 |
| Gln | Gln | His | Phe | Ser | Val | Ala | Gln | Val | Phe | Leu | Asn | Asn | Tyr | Asp | Ala | |
| | | | 100 | | | | | 105 | | | | | 110 | | | |

| GAG | AAC | AAA | CTG | AAC | GAC | ATT | CTC | CTC | ATC | CAG | CTG | AGC | AGC | CCA | GCC | 384 |
| Glu | Asn | Lys | Leu | Asn | Asp | Ile | Leu | Leu | Ile | Gln | Leu | Ser | Ser | Pro | Ala | |
| | | 115 | | | | | 120 | | | | | 125 | | | | |

| AAC | CTC | AGT | GCC | TCC | GTC | GCC | ACA | GTC | CAG | CTG | CCA | CAG | CAG | GAC | CAG | 432 |
| Asn | Leu | Ser | Ala | Ser | Val | Ala | Thr | Val | Gln | Leu | Pro | Gln | Gln | Asp | Gln | |
| | | 130 | | | | | 135 | | | | | 140 | | | | |

| CCA | GTG | CCC | CAC | GGC | ACC | CAG | TGC | CTG | GCC | ATG | GGC | TGG | GGC | CGC | GTG | 480 |
| Pro | Val | Pro | His | Gly | Thr | Gln | Cys | Leu | Ala | Met | Gly | Trp | Gly | Arg | Val | |
| 145 | | | | | 150 | | | | | 155 | | | | | 160 | |

| GGT | GCC | CAC | GAC | CCC | CCA | GCC | CAG | GTC | CTG | CAG | GAG | CTC | AAT | GTC | ACC | 528 |
| Gly | Ala | His | Asp | Pro | Pro | Ala | Gln | Val | Leu | Gln | Glu | Leu | Asn | Val | Thr | |
| | | | | 165 | | | | | 170 | | | | | 175 | | |

| GTG | GTC | ACC | TTC | TTC | TGC | CGG | CCA | CAT | AAC | ATT | TGC | ACT | TTC | GTC | CCT | 576 |
| Val | Val | Thr | Phe | Phe | Cys | Arg | Pro | His | Asn | Ile | Cys | Thr | Phe | Val | Pro | |
| | | | 180 | | | | | 185 | | | | | 190 | | | |

| CGC | CGC | AAG | GCC | GGC | ATC | TGC | TTC | GGA | GAC | TCA | GGT | GGC | CCC | CTG | ATC | 624 |
| Arg | Arg | Lys | Ala | Gly | Ile | Cys | Phe | Gly | Asp | Ser | Gly | Gly | Pro | Leu | Ile | |
| | | 195 | | | | | 200 | | | | | 205 | | | | |

| TGT | GAT | GGC | ATC | ATC | CAA | GGA | ATA | GAC | TCC | TTC | GTG | ATC | TGG | GGA | TGT | 672 |
| Cys | Asp | Gly | Ile | Ile | Gln | Gly | Ile | Asp | Ser | Phe | Val | Ile | Trp | Gly | Cys | |
| | 210 | | | | | 215 | | | | | 220 | | | | | |

| GCC | ACC | CGC | CTT | TTC | CCT | GAC | TTC | TTC | ACG | CGG | GTA | GCC | CTC | TAC | GTG | 720 |
| Ala | Thr | Arg | Leu | Phe | Pro | Asp | Phe | Phe | Thr | Arg | Val | Ala | Leu | Tyr | Val | |
| 225 | | | | | 230 | | | | | 235 | | | | | 240 | |

| GAC | TGG | ATC | CGT | TCC | ACG | CTG | CGC | CGT | GTG | GAG | GCC | AAG | GGC | CGC | CCC | 768 |
| Asp | Trp | Ile | Arg | Ser | Thr | Leu | Arg | Arg | Val | Glu | Ala | Lys | Gly | Arg | Pro | |
| | | | | 245 | | | | | 250 | | | | | 255 | | |

| TGA | | | | | | | | | | | | | | | | 771 |

(2) INFORMATION FOR SEQ ID NO:4:

( i ) SEQUENCE CHARACTERISTICS:
    ( A ) LENGTH: 27 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Met Ala His Arg Pro Pro Ser Pro Ala Leu Ala Ser Val Leu Leu Ala
 1               5                  10                  15
Leu Leu Leu Ser Gly Ala Ala Arg Ala Ala Glu
                20                  25
```

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Gln Ala Val Arg Ser Ser Ser Arg Thr Pro Ser Asp Lys Pro Val Ala
 1               5                  10                  15
```

( 2 ) INFORMATION FOR SEQ ID NO:6:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Pro Leu Ala Gln Ala Val Arg Ser Ser Ser Arg Thr Pro Ser Asp Lys
 1               5                  10                  15
Pro Val Ala His Val Val Ala
                20
```

( 2 ) INFORMATION FOR SEQ ID NO:7:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Arg Thr Pro Ser Asp Lys Pro Val Ala His Val Val Ala
 1               5                  10
```

( 2 ) INFORMATION FOR SEQ ID NO:8:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Pro Leu Ala Gln Ala Val Arg Ser Ser Ser Arg Thr Pro
```

(2) INFORMATION FOR SEQ ID NO:9:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

NGAATACTCA AGCTTGCATG GGAATTCGGC CAGCGCTGTG GGAGGG    46

(2) INFORMATION FOR SEQ ID NO:10:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

NCTCGTGCCC GCCCACGATC ATTTGCTGCA GGTCGACTCT AGA    43

(2) INFORMATION FOR SEQ ID NO:11:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

TTTTCTAGAT CTAAGCTTAT AAATGGCTCA CCGGCCC    37

(2) INFORMATION FOR SEQ ID NO:12:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

CTGCCCGGGT TCCCCCGCAT CTGCAGGGAG GCCATGTAGG GCCGGGAGTG TGGCTGCGCC    60

TCGTGCCCGC CCACGATCTC CGC    83

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

CCTGCAGGAG CTCAATGTCA CCGTGG    26

( 2 ) INFORMATION FOR SEQ ID NO:14:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

```
CGCGTTGAGC TCTAGAGGAT CCTCAGCGCA GCGTGG                                 36
```

( 2 ) INFORMATION FOR SEQ ID NO:15:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

```
CAGTTTTGTA ATAAAAAAC CTATAAATAT GCCGGATTAT TCATACCGTC CCACCATCGG         60

GCGCGGATCG GTACCAGATC TAAGCTTATA AATG                                    94
```

( 2 ) INFORMATION FOR SEQ ID NO:16:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

```
CCTCTAGAAT TCGGCCAGCG CTGTGGGAGG GGCGGTTCAG GGGCGGCCCT TGGCCTCCAC         60

ACGGCGCGCC GTGGAACGGG CCCAGTCAGC GTAGAG                                  96
```

( 2 ) INFORMATION FOR SEQ ID NO:17:

( i ) SEQUENCE CHARACTERISTICS:
        ( A ) LENGTH: 157 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Val  Arg  Ser  Ser  Ser  Arg  Thr  Pro  Ser  Asp  Lys  Pro  Val  Ala  His  Val
 1                   5                        10                       15

Val  Ala  Asn  Pro  Gln  Ala  Glu  Gly  Gln  Leu  Gln  Trp  Leu  Asn  Arg  Arg
               20                       25                       30

Ala  Asn  Ala  Leu  Leu  Ala  Asn  Gly  Val  Glu  Leu  Arg  Asp  Asn  Gln  Leu
               35                       40                       45

Val  Val  Pro  Ser  Glu  Gly  Leu  Tyr  Leu  Ile  Tyr  Ser  Gln  Val  Leu  Phe
     50                       55                       60

Lys  Gly  Gln  Gly  Cys  Pro  Ser  Thr  His  Val  Leu  Leu  Thr  His  Thr  Ile
65                       70                       75                       80

Ser  Arg  Ile  Ala  Val  Ser  Tyr  Gln  Thr  Lys  Val  Asn  Leu  Leu  Ser  Ala
                    85                       90                       95

Ile  Lys  Ser  Pro  Cys  Gln  Arg  Glu  Thr  Pro  Glu  Gly  Ala  Glu  Ala  Lys
                   100                      105                      110
```

| Pro | Trp | Tyr | Glu | Pro | Ile | Tyr | Leu | Gly | Gly | Val | Phe | Gln | Leu | Glu | Lys |
| | | 115 | | | | | 120 | | | | | 125 | | | |

| Gly | Asp | Arg | Leu | Ser | Ala | Glu | Ile | Asn | Arg | Pro | Asp | Tyr | Leu | Asp | Phe |
| | 130 | | | | | 135 | | | | | 140 | | | | |

| Ala | Glu | Ser | Gly | Gln | Val | Tyr | Phe | Gly | Ile | Ile | Ala | Leu |
| 145 | | | | | 150 | | | | | 155 | | |

(2) INFORMATION FOR SEQ ID NO:18:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

GTTTGCTACA ACATGGAGGT CCCTGGGGGA 30

(2) INFORMATION FOR SEQ ID NO:19:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:19:

| Gly | Pro | Gln | Arg | Glu | Glu | Ser | Pro | Arg | Asp | Leu | Ser | Leu | Ile | Ser | Pro |
| 1 | | | | 5 | | | | | 10 | | | | | 15 | |

| Leu | Ala | Gln | Ala |
| | | | 20 |

(2) INFORMATION FOR SEQ ID NO:20:

(i) SEQUENCE CHARACTERISTICS:
        (A) LENGTH: 229 amino acids
        (B) TYPE: amino acid
        (D) TOPOLOGY: linear (ii) MOLECULE TYPE: protein (xi) SEQUENCE DESCRIPTION: SEQ ID NO:20:

| Ile | Val | Gly | Gly | His | Glu | Ala | Gln | Pro | His | Ser | Arg | Pro | Tyr | Met | Ala |
| 1 | | | | 5 | | | | | 10 | | | | | 15 | |

| Ser | Leu | Gln | Met | Arg | Gly | Asn | Pro | Gly | Ser | His | Phe | Cys | Gly | Gly | Thr |
| | | | 20 | | | | | 25 | | | | | 30 | | |

| Leu | Ile | His | Pro | Ser | Phe | Val | Leu | Thr | Ala | Ala | His | Cys | Leu | Arg | Asp |
| | | | 35 | | | | | 40 | | | | | 45 | | |

| Ile | Pro | Gln | Arg | Leu | Val | Asn | Val | Val | Leu | Gly | Ala | His | Asn | Val | Arg |
| | | 50 | | | | | 55 | | | | | 60 | | | |

| Thr | Gln | Glu | Pro | Thr | Gln | Gln | His | Phe | Ser | Val | Ala | Gln | Val | Phe | Leu |
| 65 | | | | | 70 | | | | | 75 | | | | | 80 |

| Asn | Asn | Tyr | Asp | Ala | Glu | Asn | Lys | Leu | Asn | Asp | Val | Leu | Leu | Ile | Gln |
| | | | | 85 | | | | | 90 | | | | | 95 | |

| Leu | Ser | Ser | Pro | Ala | Asn | Leu | Ser | Ala | Ser | Val | Ala | Thr | Val | Gln | Leu |
| | | | 100 | | | | | 105 | | | | | 110 | | |

| Pro | Gln | Gln | Asp | Gln | Pro | Val | Pro | His | Gly | Thr | Gln | Cys | Leu | Ala | Met |
| | | 115 | | | | | 120 | | | | | 125 | | | |

| Gly | Trp | Gly | Arg | Val | Gly | Ala | His | Asp | Pro | Pro | Ala | Gln | Val | Leu | Gln |

|     |     |     |     | 130 |     |     |     |     | 135 |     |     |     |     | 140 |     |
| --- | --- | --- | --- | --- | --- | --- | --- | --- | --- | --- | --- | --- | --- | --- | --- |
| Glu | Leu | Asn | Val | Thr | Val | Val | Thr | Phe | Phe | Cys | Arg | Pro | His | Asn | Ile |
| 145 |     |     |     |     | 150 |     |     |     |     | 155 |     |     |     |     | 160 |
| Cys | Thr | Phe | Val | Pro | Arg | Arg | Lys | Ala | Gly | Ile | Cys | Phe | Gly | Asp | Ser |
|     |     |     |     | 165 |     |     |     |     | 170 |     |     |     |     | 175 |     |
| Gly | Gly | Pro | Leu | Ile | Cys | Asp | Gly | Ile | Ile | Gln | Gly | Ile | Asp | Ser | Phe |
|     |     |     |     | 180 |     |     |     |     | 185 |     |     |     |     | 190 |     |
| Val | Ile | Trp | Gly | Cys | Ala | Thr | Arg | Leu | Phe | Pro | Asp | Phe | Phe | Thr | Arg |
|     |     |     | 195 |     |     |     | 200 |     |     |     |     | 205 |     |     |     |
| Val | Ala | Leu | Tyr | Val | Asp | Trp | Ile | Arg | Ser | Thr | Leu | Arg | Arg | Val | Glu |
|     |     |     | 210 |     |     |     | 215 |     |     |     | 220 |     |     |     |     |
| Ala | Lys | Gly | Arg | Pro |     |     |     |     |     |     |     |     |     |     |     |
| 225 |     |     |     |     |     |     |     |     |     |     |     |     |     |     |     |

( 2 ) INFORMATION FOR SEQ ID NO:21:

( i ) SEQUENCE CHARACTERISTICS:
        ( A ) LENGTH: 177 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

| Gly | Pro | Gln | Arg | Glu | Glu | Ser | Pro | Arg | Asp | Leu | Ser | Leu | Ile | Ser | Pro |
| --- | --- | --- | --- | --- | --- | --- | --- | --- | --- | --- | --- | --- | --- | --- | --- |
| -20 |     |     |     |     | -15 |     |     |     |     | -10 |     |     |     |     | -5  |
| Leu | Ala | Gln | Ala | Val | Arg | Ser | Ser | Arg | Thr | Pro | Ser | Asp | Lys | Pro |     |
|     |     |     |     | 1   |     |     |     |     | 5   |     |     |     | 10  |     |     |
| Val | Ala | His | Val | Val | Ala | Asn | Pro | Gln | Ala | Glu | Gly | Gln | Leu | Gln | Trp |
|     |     | 15  |     |     |     |     | 20  |     |     |     |     | 25  |     |     |     |
| Leu | Asn | Arg | Arg | Ala | Asn | Ala | Leu | Leu | Ala | Asn | Gly | Val | Glu | Leu | Arg |
|     |     | 30  |     |     |     | 35  |     |     |     |     | 40  |     |     |     |     |
| Asp | Asn | Gln | Leu | Val | Val | Pro | Ser | Glu | Gly | Leu | Tyr | Leu | Ile | Tyr | Ser |
| 45  |     |     |     |     | 50  |     |     |     | 55  |     |     |     |     |     | 60  |
| Gln | Val | Leu | Phe | Lys | Gly | Gln | Gly | Cys | Pro | Ser | Thr | His | Val | Leu | Leu |
|     |     |     |     | 65  |     |     |     |     | 70  |     |     |     |     | 75  |     |
| Thr | His | Thr | Ile | Ser | Arg | Ile | Ala | Val | Ser | Tyr | Gln | Thr | Lys | Val | Asn |
|     |     |     | 80  |     |     |     |     | 85  |     |     |     |     | 90  |     |     |
| Leu | Leu | Ser | Ala | Ile | Lys | Ser | Pro | Cys | Gln | Arg | Glu | Thr | Pro | Glu | Gly |
|     |     | 95  |     |     |     |     | 100 |     |     |     |     | 105 |     |     |     |
| Ala | Glu | Ala | Lys | Pro | Trp | Tyr | Glu | Pro | Ile | Tyr | Leu | Gly | Gly | Val | Phe |
|     |     | 110 |     |     |     |     | 115 |     |     |     |     | 120 |     |     |     |
| Gln | Leu | Glu | Lys | Gly | Asp | Arg | Leu | Ser | Ala | Glu | Ile | Asn | Arg | Pro | Asp |
| 125 |     |     |     |     | 130 |     |     |     |     | 135 |     |     |     |     | 140 |
| Tyr | Leu | Asp | Phe | Ala | Glu | Ser | Gly | Gln | Val | Tyr | Phe | Gly | Ile | Ile | Ala |
|     |     |     |     | 145 |     |     |     |     | 150 |     |     |     |     | 155 |     |
| Leu |     |     |     |     |     |     |     |     |     |     |     |     |     |     |     |

( 2 ) INFORMATION FOR SEQ ID NO:22:

( i ) SEQUENCE CHARACTERISTICS:
        ( A ) LENGTH: 771 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS (B) LOCATION: 1..771

(xi) SEQUENCE DESCRIPTION: SEQ ID NO:22:

| | | | | | | | | | | | | | | | | |
|---|---|---|---|---|---|---|---|---|---|---|---|---|---|---|---|---|
| ATG | GCT | CAC | CGG | CCC | CCC | AGC | CCT | GCC | CTG | GCG | TCC | GTG | CTG | CTG | GCC | 48 |
| Met | Ala | His | Arg | Pro | Pro | Ser | Pro | Ala | Leu | Ala | Ser | Val | Leu | Leu | Ala | |
| 1 | | | | 5 | | | | | 10 | | | | | | 15 | |
| TTG | CTG | CTG | AGC | GGT | GCT | GCC | CGA | GCT | GCG | GAG | ATC | GTG | GGC | GGG | CAC | 96 |
| Leu | Leu | Leu | Ser | Gly | Ala | Ala | Arg | Ala | Ala | Glu | Ile | Val | Gly | Gly | His | |
| | | | 20 | | | | | 25 | | | | | 30 | | | |
| GAG | GCG | CAG | CCA | CAC | TCC | CGG | CCC | TAC | ATG | GCC | TCC | CTG | CAG | ATG | CGG | 144 |
| Glu | Ala | Gln | Pro | His | Ser | Arg | Pro | Tyr | Met | Ala | Ser | Leu | Gln | Met | Arg | |
| | | 35 | | | | | 40 | | | | | 45 | | | | |
| GGG | AAC | CCG | GGC | AGC | CAC | TTC | TGC | GGA | GGC | ACC | TTG | ATC | CAC | CCC | AGC | 192 |
| Gly | Asn | Pro | Gly | Ser | His | Phe | Cys | Gly | Gly | Thr | Leu | Ile | His | Pro | Ser | |
| | 50 | | | | | 55 | | | | | 60 | | | | | |
| TTC | GTG | CTG | ACG | GCC | GCG | CAC | TGC | CTG | CGG | GAC | ATA | CCC | CAG | CGC | CTG | 240 |
| Phe | Val | Leu | Thr | Ala | Ala | His | Cys | Leu | Arg | Asp | Ile | Pro | Gln | Arg | Leu | |
| 65 | | | | | 70 | | | | | 75 | | | | | 80 | |
| GTG | AAC | GTG | GTG | CTC | GGA | GCC | CAC | AAC | GTG | CGG | ACG | CAG | GAG | CCC | ACC | 288 |
| Val | Asn | Val | Val | Leu | Gly | Ala | His | Asn | Val | Arg | Thr | Gln | Glu | Pro | Thr | |
| | | | | 85 | | | | | 90 | | | | | 95 | | |
| CAG | CAG | CAC | TTC | TCG | GTG | GCT | CAG | GTG | TTT | CTG | AAC | AAC | TAC | GAC | GCG | 336 |
| Gln | Gln | His | Phe | Ser | Val | Ala | Gln | Val | Phe | Leu | Asn | Asn | Tyr | Asp | Ala | |
| | | | 100 | | | | | 105 | | | | | 110 | | | |
| GAG | AAC | AAA | CTG | AAC | GAC | ATT | CTC | CTC | ATC | CAG | CTG | AGC | AGC | CCA | GCC | 384 |
| Glu | Asn | Lys | Leu | Asn | Asp | Ile | Leu | Leu | Ile | Gln | Leu | Ser | Ser | Pro | Ala | |
| | | 115 | | | | | 120 | | | | | 125 | | | | |
| AAC | CTC | AGT | GCC | TCC | GTC | GCC | ACA | GTC | CAG | CTG | CCA | CAG | CAG | GAC | CAG | 432 |
| Asn | Leu | Ser | Ala | Ser | Val | Ala | Thr | Val | Gln | Leu | Pro | Gln | Gln | Asp | Gln | |
| | 130 | | | | | 135 | | | | | 140 | | | | | |
| CCA | GTG | CCC | CAC | GGC | ACC | CAG | TGC | CTG | GCC | ATG | GGC | TGG | GGC | CGC | GTG | 480 |
| Pro | Val | Pro | His | Gly | Thr | Gln | Cys | Leu | Ala | Met | Gly | Trp | Gly | Arg | Val | |
| 145 | | | | | 150 | | | | | 155 | | | | | 160 | |
| GGT | GCC | CAC | GAC | CCC | CCA | GCC | CAG | GTC | CTG | CAG | GAG | CTC | AAT | GTC | ACC | 528 |
| Gly | Ala | His | Asp | Pro | Pro | Ala | Gln | Val | Leu | Gln | Glu | Leu | Asn | Val | Thr | |
| | | | | 165 | | | | | 170 | | | | | 175 | | |
| GTG | GTC | ACC | TTC | TTC | TGC | CGG | CCA | CAT | AAC | ATT | TGC | ACT | TTC | GTC | CCT | 576 |
| Val | Val | Thr | Phe | Phe | Cys | Arg | Pro | His | Asn | Ile | Cys | Thr | Phe | Val | Pro | |
| | | | 180 | | | | | 185 | | | | | 190 | | | |
| CGC | CGC | AAG | GCC | GGC | ATC | TGC | TTC | GGA | GAC | TCA | GGT | GGC | CCC | CTG | ATC | 624 |
| Arg | Arg | Lys | Ala | Gly | Ile | Cys | Phe | Gly | Asp | Ser | Gly | Gly | Pro | Leu | Ile | |
| | | 195 | | | | | 200 | | | | | 205 | | | | |
| TGT | GAT | GGC | ATC | ATC | CAA | GGA | ATA | GAC | TCC | TTC | GTG | ATC | TGG | GGA | TGT | 672 |
| Cys | Asp | Gly | Ile | Ile | Gln | Gly | Ile | Asp | Ser | Phe | Val | Ile | Trp | Gly | Cys | |
| | 210 | | | | | 215 | | | | | 220 | | | | | |
| GCC | ACC | CGC | CTT | TTC | CCT | GAC | TTC | TTC | ACG | CGG | GTA | GCC | CTC | TAC | GTG | 720 |
| Ala | Thr | Arg | Leu | Phe | Pro | Asp | Phe | Phe | Thr | Arg | Val | Ala | Leu | Tyr | Val | |
| 225 | | | | | 230 | | | | | 235 | | | | | 240 | |
| GAC | TGG | ATC | CGT | TCC | ACG | CTG | CGC | CGT | GTG | GAG | GCC | AAG | GGC | CGC | CCC | 768 |
| Asp | Trp | Ile | Arg | Ser | Thr | Leu | Arg | Arg | Val | Glu | Ala | Lys | Gly | Arg | Pro | |
| | | | | 245 | | | | | 250 | | | | | 255 | | |
| TGA | | | | | | | | | | | | | | | | 771 |

(2) INFORMATION FOR SEQ ID NO:23:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: protein ( x i ) SEQUENCE DESCRIPTION: SEQ ID NO:23:

Val Arg Ser Ser
1

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:24:

Gln Ala Val Arg Ser Ser
1                   5

( 2 ) INFORMATION FOR SEQ ID NO:25:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: misc. feature
        ( D ) OTHER INFORMATION:
            / note= "Amino terminal Leu residue is
            covalently modified with a butoxycarbonyl moiety and
            carboxy terminal Ala residue is covalently modified with
            a diphenyl phosphonate moiety."

( x i ) SEQUENCE DESCRIPTION: SEQ ID NO:25:

Leu Ala Gln Ala
1

( 2 ) INFORMATION FOR SEQ ID NO:26:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:26:

Leu Ala Gln Ala
1

( 2 ) INFORMATION FOR SEQ ID NO:27:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:27:

Ala Gln Ala Val Arg Ser Ser Ser
1                   5

( 2 ) INFORMATION FOR SEQ ID NO:28:

```
( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: misc. feature
        ( D ) OTHER INFORMATION:
                / note= "Amino terminal Ala residue is
                covalently modified with a methoxysuccinyl moiety
                and carboxy terminal Val residue is
                covalently modified with a nitroanilide
                moiety."

( x i ) SEQUENCE DESCRIPTION: SEQ ID NO:28:

Ala  Ala  Pro  Val
 1
```

ASSAY METHOD FOR SCREENING FOR INHIBITORS OF PROTNF CONVERSION

This application is a continuation-in-part of both U.S. Ser. No. 08/230,428, filed Apr. 19, 1994, now pending, and U.S. Ser. No. 08/208,574, filed Mar. 7, 1994, now abandoned, which applications are a file wrapper continuation and a continuation-in-part, respectively, of U.S. Ser. No. 07/905,546, filed Jun. 25, 1992, now abandoned, which is a continuation-in-part of U.S. Ser. No. 07/395,253, filed Aug. 16, 1989, now abandoned.

FIELD OF THE INVENTION

This invention is in the area of immunology/biochemistry, and particularly concerns the development and production of compositions and methods for identifying inhibitors of protein hormone release, and prophylactic and therapeutic uses of the inhibitors for treating diseases associated with elevated levels of the hormones. More specifically, the invention facilitates the identification of compositions and methods for identifying inhibitors of a TNFα convertase. These inhibitors may be used to treat a variety of diseases, particularly sepsis, rheumatoid arthritis, cachexia, AIDS and autoimmune diseases, and thus affords the physician alternate treatment regimes.

BACKGROUND OF THE INVENTION

In the United States alone nosocomial bacteremia develops in about 194,000 patients per year, and of these about 75,000 die. Mai, D. G., 1981, *Nosocomial Infect.*, (Dikson, R. E., Ed.), page 183, Yrke Medical Books, U.S.A. Most of these deaths are attributable t o six major gram-negative bacilli—*Pseudomonas aeruginosa, Escherichia coli, Proteus, Klebsiella, Enterobacter* and *Serratia*. The current treatment for bacteremia is the administration of antibiotics which have limited effectiveness in treatment of septic shock frequently associated with bacterial infection.

The precise pathology of the septic shock sometimes associated with bacteremia is not completely elucidated. Nevertheless, it is known that certain bacterial endotoxins called lipopolysaccharides (LPS), are the primary causative agents. LPS consists of at least three significant antigenic regions: lipid A; core polysaccharide; and O-specific polysaccharide. The latter is also referred to as O-specific chain or simply O-antigen. The O-specific chain is a long-chain polysaccharide built up from repeating polysaccharide units. The number of polysaccharide units differs among different bacterial species and may vary from one to as many as six or seven monosaccharide units. While the 0-specific chain varies among different gram-negative bacteria, the lipid A and core polysaccharides are similar if not identical.

LPS initiates a cascade of biochemical events that can lead to the death of the patient. It is widely believed that an early result of exposure to LPS is the stimulation of macrophage cells and the production of tumor necrosis factor alpha (TNFα). Based on this belief, considerable effort has been expended to produce neutralizing antibodies and other molecules that could inhibit the effects of TNFα and which could serve as valuable clinical adjuncts to the standard antibiotic therapies used in the treatment of septic shock. Tracey et al., *Nature* 330:662 (1987).

While many cell types are capable of expressing TNFα, including for example, T and B lymphocytes, fibroblasts, and endothelial cells, the principal source is macrophages. TNFα has been reported to exist in both membrane-bound and soluble secreted forms. Decker et al., *J. of Immunol.* 138:957 (1987); Kriegler et al., *Cell* 53:45 (1988). Human TNFα has been cloned and consists of a 17 kD polypeptide, plus a 76-amino-acid pro sequence containing the residues that appear to be responsible for anchoring proTNFα as a type II membrane protein. The 17 kD molecule is a key agent involved in initiating the biochemical cascade responsible for sepsis. TNFα may exist as both a membrane-bound 26 kD form, and a soluble form corresponding to the 17 kD species. Kreigler et al., *Cell* 53:45 (1988). The 26 kD form is the precursor, or prohormone, of the mature 17 kD molecule. The two forms of TNFα may have different biological effects, primarily as a result of differences in tissue distribution. Kriegler et al. supra.

Because TNFα plays a key role in the sequelae of sepsis and is believed to be an inflammatory agent in diseases, there is a need to identify and develop anti-TNFα prophylactics/therapeutics. Anti-TNFα antibody has shown promise in in studies employing a baboon model system. (Hinshaw et al., *Circulatory Shock* 30:279 (1989)). However, these studies involve non-human anti-TNFα and non-human anti-TNFα antibody. In addition, TNFα is involved in inducing the expression of human immunodeficiency virus (HIV) in human cells that carry latent virus. Folks et al., *PNAS (USA)* 86:2365 (1989).

TNFα also plays a role in various autoimmune diseases, particularly rheumatoid arthritis. Duff et al., *International Conference on Tumor Necrosis Factor and Related Cytotoxins*, 175:10 (1987). Compounds or methods for inhibiting TNFα action will have considerable application for the treatment of a variety of diseases of immunologic origin. As described in Fiers et al., *FEBS Lett.* 285:199 (1991), a variety of other serious human conditions including cerebral malaria, graft-versus-host disease and ischemia/reprefusion injury, are also associated with TNFα biological activity.

In addition to anti-TNFα antibodies, other molecules with TNFα inhibitory activity are being sought. Non-antibody TNFα inhibitors are described by Seckinger et al., *Exp. H. Med.* 167:151 (1988), and Seckinger et al., *Biol. Chem.* 264:11966 (1989), and in European Patent Application No. 88830365.8, inventors Wallach et al. The inhibitors are present in the urine of febrile patients, and are reported to have molecular weights of about 27,000–33,000. These inhibitors are reported to be soluble forms of the TNFα receptor. Although these molecules exhibit TNFα-inhibitory activity, neither of the inhibitors is shown to be effective in the treatment of septic shock in humans.

From the foregoing discussion it is apparent that there is a need to identify and develop additional modulators of TNFα activity, both antibody-based or otherwise, that are efficacious in the treatment of TNFα-mediated diseases.

SUMMARY OF THE INVENTION

An approach to modulating the activities of TNFα according to the present invention involves the inhibition of TNFα convertases, for example PR-3, which are capable of converting locally produced, membrane-bound proTNFα to TNFα which contributes significantly to the pathologic processes of diseases such as septic shock and such as preventing or inhibiting the formation of the 17 kD, or lower molecular weight forms of TNFα might be a valuable prophylactic for the prevention of AIDS in HIV-positive patients by preventing the expression of virus that is latent in the patient and others described above.

In its most general form, the invention described herein presents methods and compositions for inhibiting the production of a mature form of TNFα, from its prohormone precursor, proTNFα in its 26 kD form or multimers thereof and its soluble 20 kD form or multimers thereof. These compositions are useful for preventing or treating diseases in patients associated with elevated levels of mature TNFα including septic shock, AIDS, cerebral malaria, graft versus host disease, ischemia/reperfusion injury, rheumatoid arthritis, and cachexia. The invention also relates to methods (e.g. colorimetric and autoradiographic) for identifying molecules that inhibit the production of a mature form of TNFα. Such inhibitors are distinguishable from anti-TNFα antibody or soluble TNFα receptor, which block TNFα activity by binding to TNFα.

This method may be used to identify medicaments such as prophylactics and/or therapeutics for the treatment of diseases associated with the production of mature TNFα such as those discussed above. Medicaments identified by this method interfere with the cleavage of the 26 kD proTNFα prohormone by enzymes termed convertases. Thus, these medicaments inhibit the production of lower molecular weight molecules (i.e., circulating mature forms of TNFα having subunits of 17 kD molecular weight) which play a role in the induction of "septic shock" associated with sepsis and other diseases. Specifically, preferred inhibitors as described herein interfere with the activity of a TNFα convertase to prevent removal of the N-terminal portion of the 26 kD molecule including at least the 76 amino-acid signal sequence to produce a mature form of TNFα such as the 17 kD TNFα. The invention also includes a class of compounds that are both inhibitors of a TNFα convertase and that are effective in the prevention and/or treatment of septic shock. Compounds in this class include, for example, anti-convertase antibody, muteins of the prohormone form, and proteins or peptides that compete with the 26 kD form of TNFα for binding to the convertase. Also part of the invention are small molecular weight compounds that specifically inhibit a class of proteases that includes TNFα convertases, or preferably, show selective specificity for inhibition of TNFα convertase. Such small molecular weight compounds are exemplified by, but are not limited to compounds such as the peptide diphenyl phosphonates Boc-X-p(OPh)$_2$, wherein X is a peptide selected from the group consisting of Val-Pro-Val, Ala-Pro-Val, and Val-Pro-His.

Additionally, the present invention is directed to a TNFα convertase purified to near homogeneity, the amino acid sequence of said convertase, and methods for expressing a recombinant form of TNFα convertase. One purified human TNFα convertase contains an N-terminal amino acid sequence essentially identical to human PR-3, a known neutrophil protease having the same molecular weight. The present invention is also directed to various inhibitors of TNFα convertase and methods for detecting inhibitors.

More specifically, the present invention is directed to small molecules that specifically inhibit TNFα convertases.

The invention is also directed to a method for treating diseases such as septic shock, cerebral malaria, rheumatoid arthritis, AIDS, cachexia, ischemia/reperfusion injury, and graft-versus-host disease by administering a convertase inhibitor such as a PR-3 inhibitor. Pharmaceutical compositions and medicaments comprising the convertase inhibitors of the present invention represent still another aspect of the present invention.

In one aspect of this invention, a method is provided for identifying a substance for prophylactic or therapeutic treatment of a disease caused by, exacerbated by, or associated with tumor necrosis factor (TNFα) produced from a proTNFα by cleavage of said proTNFα by a TNFα convertase, the method comprising the steps of: (a) contacting the proTNFα with an amount of the TNFα convertase effective for cleaving the proTNFα; (b) measuring the conversion of the proTNFα to the mature TNFα in step (a); (c) repeating steps (a) and (b) further including a molecule sought to be identified as a substance for prophylactic or therapeutic treatment of diseases caused by, exacerbated by, or associated with the soluble TNFα; (d) measuring the conversion of the proTNFα to the mature TNFα in step (c); and (e) comparing the conversion measured in step (b) with the conversion measured in step (c) to determine whether the molecule is a suitable prophylactic or therapeutic of diseases caused by mature TNFα. The measuring steps include but are not limited to calorimetric methods and autoradiographic methods. Possible source of such inhibitors are libraries of known elastase inhibitors.

In yet another aspect of the invention, a method is provided for treating a patient having a disease or susceptible to a disease caused by, exacerbated by, or associated with a mature TNFα produced from a proTNFα by cleavage of said proTNFα by a TNFα convertase, the method comprising administering to a patient in need of such treatment an effective amount of an inhibitor of a TNFα convertase. In a preferred embodiment, the disease is selected from the group consisting of sepsis, rheumatoid arthritis, cachexia, cerebral malaria, AIDS, autoimmune disease, and graft-versus-host disease.

In a further aspect of this invention, a pharmaceutical composition is provided for the treatment of a disease caused by a mature TNFα produced from a proTNFα by cleavage of said proTNFα by a TNFα convertase, the composition comprising an effective amount of an inhibitor of a TNFα convertase and a pharmaceutically acceptable carrier or excipient.

In another of its aspects, the present invention provides purified and isolated polypeptides and variants thereof which display biological/biochemical properties specific to the proenzyme and mature active forms of human neutrophil protease PR-3. Biological/biochemical properties of preproPR-3 include a structural amino acid sequence of the mature, active PR-3 enzyme in addition to a dipeptide, characteristic of the zymogen form of the enzyme, between the leader and amino acid sequences of mature, active PR-3.

Yet another aspect of the present invention is a purified polypeptide comprising the pro-form of a granzyme having an N-terminal amino acid sequence of X-E, wherein X represents a variable amino acid and wherein E represents glutamic acid and wherein said N-terminal sequence renders the granzyme catalytically inactive and wherein the granzyme when active catalyzes the cleavage of a membrane bound protein hormone or receptor ligand to generate the free, soluble form of the ligand.

According to another aspect of the invention, isolated polynucleotides (e.g. DNA and RNA transcripts thereof) encoding preproPR-3 and variants thereof which display useful properties of preproPR-3 are provided. Preferred DNAs of the invention include genomic and cDNA as well as wholly or partially chemically synthesized DNA. The most preferred polynucleotide sequence is set forth in SEQ ID NO: 22. Replicas (i.e., copies of isolated DNA sequences made in vivo or in vitro) of the invention are contemplated. Also provided are autonomously replicating recombinant constructions such as plasmid and viral DNA vectors incorporating preproPR-3 sequences and especially vectors wherein DNA encoding preproPR-3 or a preproPR-3 variant is operatively linked to an endogenous or exogenous expression control DNA sequence.

According to another aspect of the invention, host cells, preferably eukaryotic cells, are stably transformed with DNA of the present invention in a manner allowing the desired polypeptide to be expressed and therein processed and secreted. *Trichoplusia ni* (Tn5) insect cells infected with a viral vector containing PR-3 sequences of the present invention are also preferred. *Spodoptera frugiperda* insect cells (Sf9) infected with a viral construct containing a polynucleotide encoding preproPR-3 are variants thereof are most preferred. Other host cells contemplated by the present invention include mammalian cells such as CHO cells or human 293 cells.

Another aspect of the present invention is directed to a process for the large-scale production of the pro-form of granzymes such as proPR-3 (SEQ ID NO: 20) and variants thereof, wherein the host cells of the present invention are grown in a suitable culture medium and desired polypeptides are isolated from the cells or from the medium in which the cells are grown. The pro-form of the granzymes produced by these methods may be activated by the enzymatic removal of the N-terminal amino acid sequence using enzymes such as dipeptidyl peptidases and more particularly, dipeptidyl peptidase I.

ProPR-3 and novel PR-3 variants thereof have not been obtained from natural cell sources. However, the present invention for the production of active recombinant PR-3 or PR-3 variants is valuable for identification of TNFα convertase inhibitors. The present invention also provides for the production of useful amounts of recombinant PR-3 or PR-3 muteins in a non-pyogenic form suitable for clinical use in humans. Another aspect of the present invention are PR-3 muteins in which glycosylation has been blocked by substitution at N-linked glycosylation sites thereby improving the homogeneity and possibly the crystallizability of recombinant PR-3.

Also comprehended by the present invention are antibody substances (e.g., monoclonal and polyclonal antibodies, single-chain antibodies, chimeric antibodies, CDR-grafted antibodies and the like) which are specific for proPR-3, PR-3, and PR-3 variants and muteins. Antibody substances can be developed using isolated natural or recombinant proPR-3, PR-3, PR-3 variants or muteins thereof. Most preferred are antibody substances which are specific for the amino acid sequences including those residues unique to the pro-form, e.g. antibodies specific for the conformation of the inactive proPR-3.

In another of its aspects, the invention is directed to the treatment of cases of undesirable B cell/T cell interactionss comprising treating T cells with a therapeutic amount of PR-3 effective to release membrane bound cytokines which mediate B cell/T cell interactions.

BRIEF DESCRIPTION OF THE DRAWINGS

FIG. 1C shows the DNA and amino acid sequences of the molecule (SEQ ID NO:1);

FIGS. 2A, 2B and 2C, in sequence, show the predicted amino acid sequence (SEQ ID NO:3) of the unprocessed precursor of human PR-3, derived from the DNA sequence of the cDNA clone as described in Bories, et al. *Cell* 59:959–968 (1989);

FIGS. 3A (Lanes A-D) and 3B (Lanes A-F) are photographs of autoradiograms. FIG. 3A shows the effect of various agents on the conversion of 26 kD TNFα to 17 kD TNFα by TNF convertase in the transfected cell line TNFα 6.8; FIG. 3B similarly shows the effects of other chemical agents on the conversion of 26 kD TNFα 17 kD TNFα by TNF convertase in the transfeted cell line TNFα 6.8;

FIG. 4 is a photograph of an autoradiogram showing the conversion off 26 kD TNFα to 17 kD TNFα by the convertase activity present in HL60 cells versus various controls;

FIG. 6A is a photograph of an SDS-PAGE autoradiogram showing the differential inhibitory effects of various serine protease inhibitors on the conversion of 26 kD TNFα to its lower molecular weight forms by purified mature human neutrophil PR3;

FIG. 6B is a graph showing similar results obtained using a colorimetric assay testing the same compounds.

DETAILED DESCRIPTION OF THE INVENTION

Figures 1A, 1B:
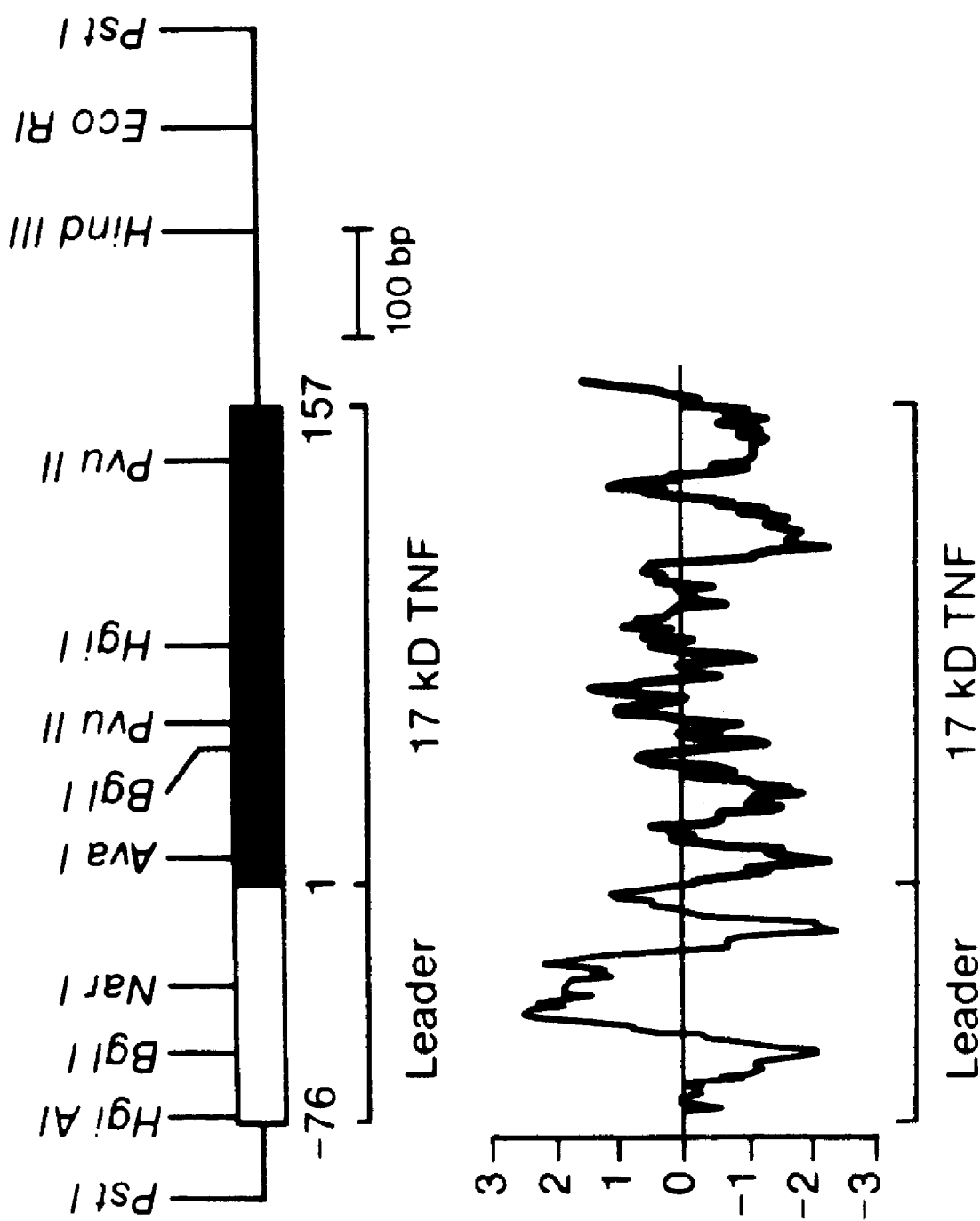
FIG. 1A, is a restriction map of the DNA sequence that encodes 26 kD TNFα.
FIG. 1B shows a hydrophobicity plot of 26 kD TNFα.

The following definitions are general in nature and encompassed within the definitions are meanings well known to those skilled in the art.

"Septic shock" is herein defined as a disease resulting from gram positive or gram negative bacterial infection, the response to the latter primarily being due to the bacterial endotoxin, lipopolysaccharide (LPS). It can be induced by at least the six major gram-negative bacilli and these are *Pseudomonas aeruginosa, Escherichia coli, Proteus, Klebsiella, Enterobacter* and *Serratia*.

A "prohormone" is a protein that contains a peptide segment which is removed during the in vivo production of a "mature" form of the hormone. A 26 kD TNFα prohormone, or "proTNFα" as discussed in detail below. ProTNFα is cleaved primarily to a 17 kD mature form, preferably having the N-terminal sequence of "mature TNFα", Val-Arg-Ser-Ser (SEQ ID NO:23). However, "mature TNFα" is intended to include other cleavage products also formed from the prohormone. These cleavage products will substantially retain the biological characteristics of the 17 kD form of mature TNFα, and are truncated (i.e., cleaved) forms of proTNFα wherein at least about 55 amino acids have been removed from the N-terminus. Mature TNFα beginning at amino acid 1 (SEQ ID NO. 17) is soluble and consists of 17 kD subunits associated in a trimeric form. Soluble recombinant proTNFα contains an additional 20 amino acids of the prosequence (−20 to −1) set out as SEQ ID NO: 19.

As used herein, "proTNFα" (SEQ ID NO 2) refers to a TNFα having a subunit molecular weight of about 26,000. The propeptide segment of a prohormone varies in length depending on the species from which it is derived, but the amino acid sequence of this segment is highly conserved. Indeed, in the mouse, approximately 86% of the 79 amino acids that make up the putative leader sequence of the prohormone are identical to the 76 known amino acids that comprise the putative leader of human TNFα. Thus, it will be appreciated by those skilled in the art that when reference is made to proTNFα it is intended that the molecule may be derived from any particular species so that it may have a slightly altered sequence compared to the human sequence as is known in the art. Similarly, "soluble proTNFα" refers to a TNFα molecule of about 20 kD lacking the proTNFα transmembrane region and containing from the glycine at position −20, relative to the putative native TNFα N-terminus to the carboxy terminus of mature TNFα (SEQ ID NO:21). This molecule has an apparent native molecular weight of about 60 kD, is soluble, and may be trimeric.

"Convertase" or "TNFα convertase" refers to one or more enzymes capable of cleaving 26 kD TNFα to a mature TNFα having TNFα biological activity in trimeric form in a TNFα cell-based bioassay using human monocyte produced 26 kD TNFα as described in Example 4. In unstimulated cells, a convertase may be recovered largely in fractions consisting substantially of membranes, although some activity is recovered from the cytosol. A TNFα convertase is normally associated with cells that produce TNFα. One TNFα convertase the serine protease "proteinase-3", also called "PR-3", "P-29b", or "myeloblastin".

The phrase "membrane-associated" as applied to TNFα convertase indicates a form of the convertase that is initially isolated in substantially insoluble form, as indicated by the presence of much of the convertase activity in a 30,000 x g pellet fraction. However, a portion of TNFα convertase may be soluble when isolated from neutrophil granules, depending on conditions such as salt concentration or pH.

PR-3 is an active mature serine protease that is capable of cleaving the proTNFα or soluble proTNFα, generating biologically active mature TNFα. PR-3 is synthesized in preproenzyme form with a 25-amino-acid leader sequence (characteristic of the preproenzyme) and a dipeptide (Ala-Glu) (characteristic of the proenzyme form) immediately downstream from the leader; both sequences must be cleaved to produce the active protease. Previous studies indicate that PR-3 can be isolated from either the culture medium of PR-3$^+$ producing cells or the insoluble membrane fraction of PR-3$^−$ producing cells. At least during some part of its processing, therefore, PR-3 is membrane-associated, but it is unclear with which membrane(s) of the cell PR-3 is associated.

Recombinant proPR-3 may be produced as a secreted soluble, inactive form of PR-3. The proPR-3 polypeptide contains the two amino acid residues, alanine and glutamic acid (Ala-Glu), positioned N-terminal to the amino acid sequences of active, mature PR-3.

"Recombinant antibody" refers to antibody wherein one portion of each of the amino acid sequences of heavy and light chain is homologous to corresponding sequences in antibody derived from a particular species or belonging to a particular class, while the remaining segment of the chains is homologous to corresponding sequences in another. Most commonly, in a recombinant antibody the variable region of both light and heavy chain copies the variable regions of antibody derived from one species of mammal, while the constant regions are homologous to the sequences in antibody derived from another. One example is "humanized" mouse antibody where the constant regions of the mouse antibody are replaced with a human constant region.

In its most general form, the instant invention concerns methods and compositions for identifying inhibitors of diseases associated with the production of mature hormones from their prohormone forms. The preferred embodiment of a prohormone is 26 kD TNFα, which is then cleaved to a lower molecular weight "mature", form, preferably 17 kD which, in its multimeric (usually trimeric) form, is substantially involved in producing life-threatening physiological changes associated with septic shock. Thus, molecules which are capable of interfering with the conversion of the 26 kD TNFα to the mature form are useful for preventing or treating septic shock or other diseases caused by, associated with, or exacerbated by production of mature TNFα.

The assays described herein detect the conversion of a prohormone to its mature hormone form, with a preferred embodiment being the enzymatic conversion of TNFα having a 26 kD subunit molecular weight to, preferably, a TNFα having a 17 kD subunit molecular weight. An enzyme responsible for the conversion is termed "TNFα convertase". Thus, the invention is most readily presented in several parts. Part one shows the materials and methods for realizing proTNFα, the 26 KD form of TNFα or soluble proTNFα. Part two identifies sources of TNFα-convertase, and methods for purifying the enzyme. Part three describes the identification of various convertase inhibitors. Part four of the invention presents a description of ways of using the inhibitors to treat patients suffering from sepsis or other diseases. Part five of the invention is directed to the expression, isolation, purification, and proteolytic activation of recombinant PR-3 and PR-3 muteins in quantities which facilitate detailed study of the biochemical and crystallographic structure of PR-3 and may be valuable for therapeutic treatment of human disease. Certain inactive muteins of recombinant PR-3 may also retain high affinity for proTNFα and thus constitute TNFα convertase inhibitors. Methods for the production of muteins are described in PCT application No. PCT/US93/05548 which is incorporated herein by reference.

All of the references, (patents/patent applications and articles) cited below are incorporated herein by reference.

I. Recombinant Constructs of proTNFα and Soluble TNFα

The TNFα, proTNFα, and soluble proTNFα of the current invention may be obtained in native, synthetic or recombinant forms by methods known in the art. While the recombinant systems described below render the 26 kD proTNFα and 20 kD soluble proTNFα obtainable in considerable amounts and facilitate the assay procedures for TNFα inhibitors, it will be appreciated that nonrecombinant systems may also be used. For instance, it has been shown that the 26 kD molecule can be identified in stimulated monocytes. Kreigler et al., *Cell* 53:45 (1988). Thus, a suitable assay procedure is to stimulate monocytes to produce the 26 kD proTNFα molecule, and then to measure the cleavage of the 26 kD molecule as a result of action by the convertase. Preferably the 17,000 molecular weight mature TNFα subunit is generated.

The 26 kD proTNFα is cleaved by convertase at one or more internal sites to generate "mature TNFα". The major site is at the junction which separates the secreted form of TNFα (the 17 kD species) from the leader sequence. The sequence at this junction is believed to be Gln-Ala-Val-Arg-Ser-Ser (SEQ ID NO:24). A major putative cleavage site lies between alanine and valine, since Val-Arg-Ser-Ser is believed to be the amino-terminal sequence of the 17 kD TNFα molecule (the primary mature form as isolated from human cell culture supernatants in vitro). Other species of TNFα may be produced by the convertase, and these are the products of secondary cleavage sites: for example, between the Val and the Arg in the sequence above, or between Pro and the Val located at +12 and +13 in the amino acid sequence. The assays described herein can monitor the inhibition of the conversion proTNFα species (including soluble proTNFα), or the appearance of a mature TNFα form irrespective of its cleavage site.

The proTNFα form and mature TNFα form have been cloned and expressed in a number of systems. For instance, the cloning of rabbit TNFα is disclosed in EP 146,026, published Jun. 26,1985 (Dainippon Pharmaceutical Co., Ltd.) and EP 148,311, published Jul. 17,1985 (Asahi Kasei Kogyo Kabushiki). The cloning of human TNFα having 151 and 155 amino acids (2 and 6 less than the putative native mature form) is disclosed in EP 155,549, published Sep. 25,1985 (Dainippon Pharmaceutical Co., Ltd.), and human TNFα having 155 amino acids (missing Val-Arg) is disclosed in EP 158,286, published Oct. 16,1985 (Asahi Kasei Kogyo Kabushiki Kaisha) and corresponding GB 1,158, 829A, published Nov. 20,1985. The cloning of mature TNFα (157 amino acids) and various modified forms (muteins) thereof is disclosed in EP 168,214, published Jan. 15, 1986 (Genentech) and PCT US 85/01921, filed Oct. 3, 1985, (Cetus Corporation).

U.S. Pat. Nos. 4,677,063 and 4,677,064 show cDNA sequences that encode the 26,000 and 17,000 forms of TNFα, as well as muteins of these molecules.

The cDNA sequence that encodes the 26 kD TNFα species is preferably obtained from the plasmid pB11 described in commonly owned application, U.S. Ser. No. 06/670,360, now abandoned, filed Nov. 9,1984; and U.S. Pat. Nos. 4,677,063 and 4,677,064. The plasmid pB11 contains the SV40 promoter in operable linkage to the TNFα coding sequence, and thus is useful for expressing the 26 kD TNFα species in eukaryotic host cells. Additionally, a second plasmid which contains the entire sequence which encodes the 26 kD TNFα species is described in the forgoing U.S. patent application and patents. It is designated pE4. The plasmid pE4 is on deposit with the American Type Culture Collection, Accession No. 39894.

The cDNA sequence that encodes the 26 kD TNFα species is present in the plasmid pB11 as a PstI fragment. Thus, it is readily removed and inserted into any one of a number of suitable expression systems. The preferred expression system is the plasmid pFVXM, which is described in U.S. Ser. No. 06/855,865, now abandoned, entitled Infective Drug Delivery System, inventor Kriegler et al. (abandoned in favor of U.S. Ser. No. 07/571,017, filed Aug. 22,1990, now abandoned). pFVXM is on deposit with the American Type Culture Collection and has Accession No. 67,103.

pFVXM is a retroviral vector derived from the plasmid pEVX described by Kriegler et al., *Cell* 38:483 (1984). pEVX has a Moloney murine leukemia virus derived splice donor site 3' to the 5' -long terminal repeat. It was previously shown that this splice donor sequence decreases the yield of correctly spliced translational templates of retroviral constructions. Thus, pEVX was engineered to remove the splice donor site, and replaced with an analogous SmaI fragment of the Harvey murine sarcoma virus genome, which lacks the Moloney murine leukemia virus splice donor sequence. The resulting vector, pFVXM, lacks the Moloney murine leukemia virus spliced donor sequence and carries a viral packaging sequence. pFVXM has a convenient PstI site in which the DNA sequences that encodes the 26 kD TNFα species can be inserted.

II. TNFα Convertase

A TNFα convertase must have proteolytic activity. A variety of biological materials are available as sources of TNFα convertase activity. These include tissues, cells, or extracts, or fluids associated therewith that are often, but not necessarily, of immunologic origin. Moreover, established cell lines may also be utilized. Suitable sources would include human peripheral blood mononuclear cells, such as leukocytes or cell lines of leukocyte origin, preferably macrophages and monocytes. Neutrophils are a particularly useful source of TNFα convertase. Because of the ease of manipulating established cell lines, one preferred cell source of TNFα convertase is the HL60 cell line. Thus, the conversion of the 26 kD proTNFα species to mature TNFα can be affected by combining the 26 kD species with extracts derived from HL60 cells. Further, because the TNFα convertase activity is partially membrane-associated under certain conditions, it is possible to obtain a membrane fraction that may be utilized.

The procedures for isolating monocytes are well known in the art, as are other methods for culturing cell lines such as HL60. Briefly, monocytes may be prepared from peripheral blood by centrifugation with Ficoll-hypaque according to standard procedures. This yields an enriched population of monocytes and lymphocytes, and the monocytes can be further enriched by plating the mixture of cells onto tissue culture dishes and incubating the cells for a time sufficient to permit the monocytes to adhere to the surface of the dishes. The lymphocytes are then washed off of the plates leaving primarily adherent monocytes. These cells may then be used as is, or can be stimulated to produce enhanced levels of TNFα convertase using known monocyte activators, preferably lipopolysaccharide and phorbol myristate acetate. The cells may be fractionated, and either an extract or a membrane fraction prepared therefrom and employed in the assays described below.

A TNFα convertase was isolated from 12 liters of HL60 culture by isolating the cell membrane fraction, solubilizing it in a 0.5% Nonidet P-40 detergent, subjecting the solution to anion exchange chromatography, cation exchange-HPLC, anion exchange-HPLC, and reverse-phase HPLC to yield 20 μg of 1,000-fold purified TNFα convertase, at an 18% yield. The convertase was found to have a molecular weight of approximately 29–30 kD by SDS-PAGE analysis (silver-stained). The convertase was sequenced, and the first amino acids were found to be identical, within experimental error, to the mature N-terminal sequence of a known neutrophil proteinase, PR-3 (Campanelli et al., *J. Exp. Med.* 178:1709–1715 (1990). The purified convertase was shown to cleave the 26 kD proTNFα to the 17 kD mature form.

PR-3 may also be isolated from neutrophils. Neutrophils are separated from human blood, then granules and membranes are isolated, and the mixture is fractionated on RP-HPLC, as described in Example 1.

As described more fully below, the amino acid sequence for PR-3 has been elucidated, as predicted from the sequence of the cDNA clone (SEQ ID NO. 22). PR-3 is known in the art as a protease having activities unrelated to TNFα processing. It is classified as a human polymorphonuclear leukocyte serine proteinase that degrades elastin, fibronectin, laminin, vitronectin, and collagen type IV; see Rao et al., *J. Biol. Chem.* 266:9540–9548 (1991). Purified PR-3 from human neutrophils has been reported to have a major band at 26.8 kD as analyzed by SDS-PAGE. Two smaller bands having slightly larger molecular masses, possibly representing different glycosylated species, (see Rao et al. supra.) are also seen. PR-3 is structurally similar to other serine proteases, such as elastase, cathepsin G, mouse granzyme B, rat mast cell protease II, human lymphocyte protease, and chymotrypsin, (see Campanelli et al., *J. Exp. Med.* 172:1709–1715 (1990)). PR-3 is inhibited by α2-macroglobulin, phenylmethyl-sulfonyl fluoride (PMSF), and α1- antitrypsin. Sequencing of the PR-3 digestion products of radiolabelled 26 kD TNFα show that PR-3 is capable of cleaving the proTNFα to produce an N-terminal Val-Arg-Ser sequence (amino acids 1–3 of the 17 kD mature form). Cleavage may occur to produce an Arg-Ser-Ser N-terminus or Val-Ala-His N-terminus. Rao et al., supra, report that PR-3 prefers small aliphatic amino acids in the SI cleavage site. Human serine proteases such as cathepsin G and plasmin do not efficiently convert the 26 kD proTNFα to the 17 kD mature form. Elastase does appear to have some TNFα convertase activity but also degrades mature TNFα.

As shown below, PR-3 is inhibited by peptide diphenyl phosphonate inhibitors, elastinal, and dichloro-isocoumarin (DCI). The peptide diphenyl phosphonate inhibitors include Boc-Val-Pro-Val-p(OPh)$_2$ and Boc-Ala-Pro-Val-p(OPh)$_2$ (BOC-butoxycarbonyl). Boc-Ala-Gln-Ala-p(OPh)$_2$ and Boc-Leu-Ala-Gln-Ala-p(OPh)$_2$(SEQ ID NO:26), have also been tested and have much less inhibitory activity. "Boc" means N-tert-butoxycarbonyl and "p(OPh)2" represents the diphenyl phosphonate moiety, wherein the formula —COOH group is replaced with P(—0)-(O-phenyl)$_2$. See Oleksyszyn et al., *Biochem* 30:485 (1991). It will be appreciated that other peptide diphenyl phosphonate molecules may inhibit PR-3. Potential inhibitors may be constructed using the procedures shown in Oleksyszyn et al., supra, using small aliphatic peptides, for an example. Once the potential inhibitors are made, they may be tested in the assays shown below.

Because of the relative paucity of native PR-3 obtainable from neutrophils, recombinant proPR-3 was produced in insect cells in culture. Recombinant proPR-3 was isolated from the cell culture medium and was activated using a dipeptidyl peptidase I (DPPI) to remove the N-terminal ALA-GLU dipeptide. This apparently represents the first recombinant preparation of an active PR-3 and the first use of DPPI to activate a recombinant granzyme zymogen in vitro.

III. Inhibitors of TNFa Convertase Activity

Inhibitors of convertase activity will be used prophylactically or therapeutically in the treatment of sepsis and certain other diseases in which circulating TNFα has been implicated. Inhibitors of TNFα convertase can be identified by procedures that enable one to measure the conversion of proTNFα or soluble proTNFα to mature TNFα. Several such assay procedures are described herein, and in Example 4 below. A suitable assay would consist of combining 26 kD proTNFα, a TNFα convertase, and a putative inhibitor. It will be understood by those skilled in the art that the inhibitory material may be added to the convertase before the convertase is added to TNFα, or it can be added to TNFα prior to, or immediately after adding the convertase. The order of addition may facilitate identification of inhibitors. If a substance has inhibitory activity, this can be revealed by electrophoretic analysis of the solution which will reveal, relative to control reaction, an increase in the amount of the 26 kD species, and concomitantly a decrease in mature TNFα species. Applicants have also identified a colorimetric assay to detect convertase inhibitors. The assay is convenient and correlates with the autoradiographic assay for cleavage of 26 kD TNFα. The colorimetic assay is described in detail in Example 4. Also see Kam et al., *FEBS* 297 (1,2):119–123 (1992). Other cell-based assays or assays based on soluble proTNFα conversion to mature TNFα are also useful.

Other compounds with anti-convertase activity include anti-convertase antibody, either polyclonal or monoclonal, or recombinant antibody. Preferably these antibodies will be humanized antibodies. Monoclonal antibody to the convertase may be produced using the general procedures described by Kohler, G. and Milstein, C. *Nature* 256:495 (1975), which have been modified over the years as is known in the art. These initial studies involved fusing murine lymphocytes and drug selectable plasmacytomas to produce hybridomas. Subsequently, the technique has been applied to produce hybrid cell lines that secrete human monoclonal antibodies. The latter procedures are generally described in Abrams, P. *Methods in Enzymology*, 121:107 (1986), but other modifications are known to those skilled in the art. Regardless of whether murine or human antibody is produced, the antibody-secreting cells are combined with the fusion partner and the cells fused with a suitable fusing agent, preferably polyethylene glycol, and more preferably polyethylene glycol 1000. The latter is added to a cell pellet containing the antibody-secreting cells and the fusion partner in small amounts over a short period of time accompanied with gentle agitation. After the addition of the fusing agent, the cell mixture is washed to remove the fusing agent and any cellular debris, and the cell mixture consisting of fused and unfused cells seeded into appropriate cell culture chambers containing selective growth media. After a period of several weeks, hybrid cells are apparent, and may be identified as to antibody production and subcloned to ensure the availability of a stable hybrid cell line.

A preferred antibody is human monoclonal antibody which can be produced from lymphocytes sensitized with convertase either in vivo or in vitro and immortalized as antibody-producing hybrid cell lines, thereby making available a renewable source of the desired antibody. In vitro immunization techniques are well known in the art, and are generally described by Luben, R. and Mohler, M., *Molecular Immunology* 121:635 (1980), Reading, C. *Methods in Enzymology, (Part One):*18, or Voss, B., *Methods in Enzymology*, 124:27 (1986). A number of in vitro immunization systems have been shown to be effective for sensitizing human B-cells. Reading, C., *J. of Immun. Methods*, :261 (1982).

It will be apparent to those skilled in the art, that in lieu of immunizing individuals directly with TNFα convertase, lymphocytes may be isolated from individuals that are experiencing, or have experienced, a bacteremic attack. For example, human patients having Wegener's granulomatosis are natural source of antiPR-3 antibodies and also contain human cells suitable for deriving human monoclonal antibodies. A fraction of these lymphocytes will be sensitized to the convertase and may be used to produce permanent antibody-secreting hybrid cell lines. For example, immunocompromised human patients are generally susceptible to bacterial infections, particularly those suffering from various malignancies, extensive burns, etc., and lymphocytes isolated therefrom may be a source of antibody-secreting cells.

Sensitized lymphocytes can be immortalized by viral transformation. The preferred viral transformation technique for human lymphocytes involves the use of Epstein-Barr virus. The virus is capable of transforming human B-cells, and has been used to generate human monoclonal antibodies. Crawford et al., *J. of General Virology* 64:697 (1983); Kozbor, V. and Roder, J., *J. Immun. Today* 4:72 (1983).

Another procedure whereby sensitized lymphocytes may be immortalized consists of a combination of the above two techniques, that is viral transformation and cell fusion. The preferred combination consists of transforming antibody-secreting cells with Epstein-Barr virus, and subsequently fusing the transformed cells to a suitable fusion partner. The fusion partner may be a mouse myeloma cell line, a heteromyeloma line, or a human myeloma line, or other immortalized cell line. PCT No. 81/00957; Schlom et al., *PNAS (USA)* 77:6841 (1980): Croce et al., *Nature* 288:488 (1980). The preferred fusion partner is a mouse-human heterohybrid, and more preferred is the cell line designated F3B6. This cell line is on deposit with the American Type Culture Collection, Accession No. HB8785. It was deposited Apr. 18, 1985. The procedures for generating F3B6 are described in EPA No. 174,204.

Techniques applicable to the use of Epstein-Barr virus transformation and the production of immortal antibody-secreting cell lines are presented by Roder, J. et al., *Methods in Enzymology* 121:140 (1986). Basically, the procedure consists of isolating Epstein-Barr virus from a suitable source, generally an infected cell line, and exposing the target antibody-secreting cells to supernatants containing the virus. The cells are washed and cultured in an appropriate cell culture medium. Subsequently, virally transformed cells present in the cell culture can be identified by the presence of the Epstein-Barr viral nuclear antigen, and transformed antibody-secreting cells can be identified using standard methods known in the art.

It will be apparent to those skilled in the art that while a preferred embodiment of the instant invention is a neutralizing anti-TNFα convertase monoclonal antibody, singly or in combination, that the antibody(s) may be altered and still maintain biological activity. Thus, encompassed within the scope of the invention is antibody modified by reduction to various size fragments, such as F(ab')$_2$, Fab, Fv, or the like. Also, the hybrid cell lines that produce the antibody may be considered to be a source of the DNA that encodes the desired antibody which may be isolated and transferred to cells, by known genetic techniques, to produce genetically engineered antibody. An example of the latter would be the production of single-chain antibody having the antibody combining site of the hybridomas described herein. Single-chain antibodies are described in U.S. Pat. No. 4,704,692. A second example of genetically engineered antibody is recombinant, or chimeric antibody. Methods for producing recombinant antibody are shown in U.S. Pat. No. 4,816,567, to Cabilly et al. Japanese Patent Application No. 84169370, filed Aug. 15,1984; U.S. Ser. No. 06/644,473, filed Aug. 27,1984, now abandoned; British Patent Application No. 8422238, filed on Sep. 3,1984; Japanese Patent Application, No. 85239543, filed Oct. 28, 1985; U.S. Ser. No. 06/793,980 on Nov. 1,1985, now abandoned; U.S. Ser. No. 07/077,528, filed Jul. 24,1987, now abandoned. Also, British Patent Application No. 867679, filed Mar. 27,1986 describes methods for producing an altered antibody in which at least parts of the complementary determining regions (CDRs) in the light or heavy chain variable domains have been replaced by analogous parts of CDRs from an antibody of different specificity. Using the procedures described therein, it is feasible to construct recombinant antibody having the CDR region of one species grafted onto antibody from a second species that has its CDR region replaced. The preferred embodiment in this instance is a murine anti-convertase antibody CDR region that replaces the CDR region of human antibody.

In addition to antibodies, compounds that compete with 26 kD proTNFα for binding to the convertase will inhibit or reduce the conversion of 26 kD proTNFα to the mature form, and may thus be useful medicaments for treating sepsis and other diseases. One such class of reagents consists of peptides, polypeptides, or proteins, or other compounds synthetic, or naturally occurring, that have TNFα convertase-binding activity similar to or better than the 26 kD proTNFα. Preferred peptides or proteins are those that contain amino-acid sequences similar to that found at the junction between the 76 amino acid leader sequence of proTNFα and the 17 kD mature form but which are not efficiently cleaved by the convertase.

An alternate embodiment of a peptide/protein convertase inhibitor is one that has an amino acid sequence that is functionally similar to (SEQ ID NO: 5). This peptide spans two TNFα convertase cleavage sites and thus would prevent the formation of the 17 kD mature TNFα, among others. The first and dominant cleavage site is between alanine and valine at positions −1 and +1 of SEQ ID NO. 2; and secondary sites are between valine and arginine at positions +1 and +2 of SEQ ID NO. 2, and proline and valine at positions +12 and +13 of SEQ ID NO. 2, all of which also correspond to the amino acid sequence shown in FIG. 1 (SEQ ID NO: 1).

A second class of competitive inhibitors consists of compounds including the sequence shown above, that is (SEQ ID NO: 1), but wherein certain amino acids have been altered or deleted to yield a non-cleavable substrate. A preferred embodiment of this peptide is a 26 kD proTNFα or soluble proTNFα mutein produced by standard site-specific mutagenesis techniques. For example, deletions or substitutions of certain amino acids in the region from position −21 to +13 and more preferably from −5 to +13 may represent inhibitors of TNFα convertase.

The peptides described above can be made by techniques well known in the art, such as, for example, the Merrifield solid-phase method described in *Science* 232:341–347 (1985). The procedure may use commercially available synthesizers such as a Biosearch 9500 automated peptide machine, with cleavage of the blocked amino acids being achieved with hydrogen fluoride, and the peptides purified by preparative HPLC using a Waters Delta Prep 3000 instrument, on a 15–20 μm Vydac C4 PrepPAK column. Other methods include expression of polypeptides such as muteins of soluble proTNFα in yeast or *E. coli* host cells.

The peptide diphenyl phosphonates described above are also used as inhibitors. Useful peptides may be attached to Boc and the diphenyl phosphonate moiety (see Oleksyszyn et al., *Biochem.* 30:485 (1991), and tested in a convertase inhibition assay. Preferred peptides are Boc-Val-Pro-Val-p (OPh), Boc-Ala-Pro-Val-p(OPh)$_2$, and Boc-Val-Pro-His-p (OPh)$_2$. However, it will be seen that other peptide diphenyl phosphonates may be used in the inhibition assays described below to identify further TNFα convertase inhibitors. Examples are disclosed below and are shown in Oleksyszyn et al., *Biochem.* 30:485 (1991).

The apparent substrate specificity of the identified TNFα convertase, PR-3, is believed to be similar to that of enzymes such as elastase, which typically cleave immediately following certain neutrally charged amino acids, such as valine or alanine residues. Thus, in addition to the peptide inhibitors mentioned above, a variety of other inhibitors known to inhibit elastase may also generally inhibit an enzyme that cleaves the 26 kD proTNFα to form soluble TNFα. Those compounds that inhibit TNFα convertase can be identified using the assays described below. A variety of elastase inhibitors are commercially available from suppliers such as Boehringer Mannheim Biochemicals, or are known in the art. Doherty et al., *Nature* 322:192, (1986); U.S. Pat. Nos. 4,711,886; 4,797,396; 4,717,722; and 4,699,904. The preferred elastase inhibitors are modified cephalosporin antibiotics, such as those shown by Doherty et al., supra. More preferred is (1 -((3-((acetyloxyl)-7-methoxy-8-oxy-8-ox-5-thio- 1 -azabicyclo [4.2.0] oct-2-en- 2-yl) carbonyl) morpholine, S, S-dioxide, (6R-cis). Also, Stetler et al., *Nucleic Acids Research* 4:7883 (1986), describe a cDNA clone that codes for an inhibitor of neutrophil elastase.

Additionally, inhibitors may be found by modeling the crystal structure for PR-3 by modifying the known structure for the closely homologous human neutrophil elastase molecule. Such models predict potential important contact points in the substrate-binding site of PR-3. The importance of these contact points may be tested by altering residues via site-directed mutagenesis and measuring the effect on substrate and inhibitor profiles of the new recombinantly expressed enzyme as described below. Potential inhibitors may be designed based on this information and then tested in the present assay systems, as well as in relevant animal models for septic shock.

Recombinant techniques may be used to obtain the inhibitors, the proTNFαs, mature TNFαs, TNFα convertases and pro-forms of TNFα convertases such as proPR-3 described herein. Most of the recombinant techniques that are described herein that may be used to transform cells, fabricate vectors, extract messenger RNA, and the like are widely practiced in biotechnology and most practitioners are familiar with the standard materials and methods employed. However, for convenience, the following paragraphs are offered as a guideline.

A. General Cloning Techniques

Construction of suitable vectors containing the desired TNFα coding sequence employs standard ligation and restriction techniques which are well understood in the art. Isolated vectors, DNA sequences, or synthesized oligonucleotides are cleaved, tailored, and ligated in the form desired.

Site-specific DNA cleavage is performed by treating DNA with suitable restriction enzyme(s) under conditions which are generally understood in the art, and the particulars of which are specified by the manufacturer of these commercially available restriction enzymes. See, e.g., New England Biolabs, Product Catalog. In general, about 1 pg of plasmid or DNA sequence is cleaved by one unit of enzyme in about 20 $\mu$l of buffer solution. In the examples herein, typically, an excess of restriction enzyme is used to ensure complete digestion of the DNA substrate. Incubation times of about 1–2 hours at about 37° C. are workable, although variations can be tolerated. After each incubation, protein is removed by extraction with phenol/chloroform, and may be followed by ether extraction, and the nucleic acid recovered from aqueous fractions by precipitation with ethanol followed by chromatography using a Sephadex G-50 spin column. If desired, size separation of the cleaved fragments may be performed by polyacrylamide gel or agarose gel electrophoresis using standard techniques. A general description of size separations is found in *Methods in Enzymology* 65:499–560 (1980).

Restriction cleaved fragments may be blunt-ended by treating with the large fragment of *E. coli* DNA polymerase I, that is, the Klenow fragment, in the presence of the four deoxynucleotide triphosphates (dNTPs) using incubation times of about 15–25 minutes at 20°–25° C. in 50 mM Tris pH 7.6, 50 mM NaCl, 6 mM MgCl$_2$, 6 mM DTT, and 10 mM dNTPs. After treatment with Klenow, the mixture is extracted with phenol/chloroform and ethanol precipitated. Treatment under appropriate conditions with S1 nuclease results in hydrolysis of single-stranded portions of the molecule.

Ligations are performed in 15–30 ul volumes under the following standard conditions and temperatures: 20 mM Tris-Cl pH 7.5, 10 mM MgCl$_2$, 10 mM DTT, 33 $\mu$g/ml BSA, 10 mM-50 mM NaCl, and 1 mM ATP, 0.3–0.6 (Weiss) units T4 DNA ligase at 4° C. for "sticky-end" ligation, or for "blunt-end" ligations. Intermolecular "sticky end" ligations are usually performed at 33–100 $\mu$g/ml total DNA concentration. In blunt-end ligations, the total DNA concentration of the ends is about 1 $\mu$M.

In vector construction employing "vector fragments," the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{+2}$ using about 1 unit of BAP per pg of vector at 60° C. for about 1 hour. Nucleic acid fragments are recovered by extracting the preparation with phenol/chloroform, followed by ethanol precipitation. Alternatively, religation can be prevented in vectors which have been double-digested by additional restriction enzyme digestion of the unwanted fragments.

In the constructions set forth below, correct ligations are confirmed by first transforming the appropriate *E. coli* strain with the ligation mixture. Successful transformants are selected by resistance to ampicillin, tetracycline or other antibiotics, or using other markers depending on the mode of plasmid construction, as is understood in the art. Miniprep DNA can be prepared from the transformants by the method of Ish-Howowicz et al., *Nucleic Acids Res.*, 2:2989 (1981), and analyzed by restriction and/or sequenced by the dideoxy method of Sanger et al., *PNAS* (*USA*) 74:5463 (1977), as further described by Messing et al., *Nucleic Acids Res.* 2:309 (1981), or by the method of Maxam et al., *Methods in Enzymology* 65:499 (1980). In the case of PR-3 sequencing, particular attention must be paid to regions of high G/C content in order to obtain the correct sequence. Differences between the PR-3 sequence of the present application and several reported in the prior art may be due, in part, to sequencing errors rather than clonal variation.

Host strains used in cloning in M13 consist of *E. coli* strains susceptible to phage infection, such as *E. coli* K12 strain DG98. The DG98 strain has been deposited with ATCC Jul. 13,1984 and has Accession No. 1965.

Depending on the host cell used, transformation is done using standard techniques appropriate to such cells. Calcium treatment employing calcium chloride, as described by Cohen, *PNAS* (*USA*) 69:2110, or the RbCl$_2$ method described by Maniatis et al., *Molecular Cloning: A Laboratory Manual*, Cold Spring Harbor Press, p. 254, (1984), may be used for procaryotes. Transfection may also achieved using a modification of the calcium phosphate precipitation technique of Graham et al., *Virology* 52:456 (1973), or Wigler et al., *Cell* 14:725 (1978).

B. Oligonucleotide Probes

Synthetic oligonucleotides are prepared by the triester method of Matteucci et al., *J. Am Chem. Soc.* 103:3185 (1981) or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM $MgCl_2$, 5 mM dithiothreitol, 1–2 mM ATP, 1.7 pmoles $^{32}p$ ATP (2.9 mCi/mmole), 0.1 mM spermidine, 0.1 mM EDTA.

C. Mutagenesis

Mutagenesis can be carried out using any number of procedures known in the art. These techniques are described by Smith, *Annual Review of Genetics* 19:423 (1985), and modifications of some of the techniques are described in *Methods in Enzymology* 154, part E, (eds.) Wu and Grossman (1987), chapters 17,18,19, and 20. The preferred procedure is a modification of the gapped-duplex site-directed mutagenesis method. The general procedure is described by Kramer supra, in chapter 17 of the *Methods in Enzymology*.

Conventional M13 mutagenesis methods involve annealing a short synthetic oligonucleotide to single stranded M13 DNA having a cloned target coding sequence that is sought to be mutagenized. The oligonucleotide is almost, but not entirely complementary to the target sequence and has at least one mispaired nucleotide. After the annealing reaction, the remaining portion of the single stranded DNA must be filled in to give heteroduplex DNA that can be transfected into a suitable host cell which allows for the expression of the mutation. In the gapped-duplex method, a partial DNA duplex is constructed that has only the target region exposed, unlike the conventional methods which have the target region and the rest of the single-stranded M13 DNA exposed. Like the conventional methods, a short oligonucleotide is annealed to the target region, and extended and ligated to produce a heteroduplex. However, because only a small portion of single-stranded DNA is available for hybridization in the gapped-duplex method, the oligonucleotide does not anneal to undesired sites within the M13 genome. Further, this method has the additional advantage of introducing fewer errors during the formation of the heteroduplex since only a very small region of DNA on either side of the target region has to be filled in.

More specifically, the gapped-duplex method involves cloning the target DNA sequence into an appropriate M13 phage that carries selectable markers, such as for example the stop codon amber mutation. The latter allows for negative selection in a host cell that cannot suppress the effects of the mutation. Preferably the phage is M13mp9 which contains two amber codons in critical phage genes. Thus, the sequence that encodes 26 kD TNFα is cloned into M13mp9 amber$^+$, and single-stranded DNA is prepared therefrom using standard techniques. Next, double-stranded replicative form DNA from M13 GAP, a genetically engineered M13 derivative that lacks the amber codons is cleaved with HincII restriction enzyme. The base sequence of M13 GAP is similar to M13mp18, which lacks both the amber codons and the sequence between base pairs 6172 and 6323. This deletion flanks the multiple cloning sites of the M13mp series and generates a unique HincII site. Gapped-duplex DNA is formed, using standard DNA/DNA hybridization techniques, consisting of single-stranded DNA having the amber codons, and a second strand of DNA from HincIII digested M13 GAP lacking both the amber codons and the TNFα coding sequences. Thus, the only portion of the gapped duplex that is exposed is the 26 kD TNFα target sequence. The desired oligonucleotide is annealed to the gapped-duplex DNA, and any remaining gaps filled in with DNA polymerase and the nicks sealed with DNA ligase to produce a heteroduplex. The latter is transfected, preferably into a mismatch repair deficient host, and mixed phage produced. From the mixed phage population, phage carrying unmutated 26 kD TNFα DNA, which also have the amber mutations, can be selected against by infecting the mixed phage population into a host cell that cannot suppress the amber mutation. Clones can then be screened for phage that carry the desired TNFα mutation.

IV. Methods of Use of TNFα Convertase Inhibitors

Compounds identified as having TNFα convertase-inhibitory activity will also have prophylactic or therapeutic applications in the treatment of septic shock or other TNFα-mediated diseases. Because the onset of sepsis is associated with an increase in circulating mature TNFα, these inhibitors may be used prophylactically in those instances where there is a risk of bacterial infection, particularly in a pre-operative setting. Similarly, when there is an early diagnosis of sepsis, the inhibitors will have beneficial therapeutic effects in substantially reducing the amount of the soluble, 17 kD form of TNFα that is produced.

Increases in circulating mature TNFα are associated with the diseases rheumatoid arthritis, cachexia, cerebral malaria and graft-versus-host disease. Thus, the inhibitors of this invention will also have useful prophylactic or therapeutic applications in the treatment of these diseases.

The inhibitors of this invention may be administered at concentrations that are therapeutically effective for prevention of septic shock, AIDS, etc. To accomplish these goals, the peptides, peptoids, or chemical compounds are administered parenterally (i.e., via intravascular [intra-arterial or intravenous], intramuscular, intra-articular, or subcutaneous routes). In certain cases, such as rheumatoid arthritis, local applications (intra-articular) may have beneficial therapeutic effects. Methods to accomplish this administration are known to those of ordinary skill in the art.

Before administration to patients, formulants or pharmaceutically acceptable excipients may be added to the peptides and chemical compounds. A liquid formulation is preferred. For example, these formulants may include oils, polymers, vitamins, carbohydrates, amino acids, buffers, albumin, surfactants, or bulking agents. Preferably carbohydrates include sugar or sugar alcohols such as mono-, di-, or polysaccharides or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. Sugar alcohol is defined as a C4 to C8 hydrocarbon having an -OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v% and 7.0 w/v%, more preferable between 2.0 and 6.0 w/v%. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Physiologically compatible buffers may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP Nos. 270,799 and 268,110.

Additionally, the present peptides, peptoids, or chemical compounds can be chemically modified by covalent conjugation to a polymer to increase their circulating half-life, for example. Preferred polymers, and methods to attach them to peptides, are shown in U.S. Pat. Nos. 4,766,106, 4,179,337, 4,495,285, and 4,609,546 which are all hereby incorporated by reference in their entireties. Preferred polymers are polyoxyethylated polyols and polyethylene glycol (PEG). PEG is soluble in water at room temperature and has the general formula: $R(O-CH_2-CH_2-ON-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor.

Water-soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. The POG has a preferred molecular weight in the same range as PEG. The structure for POG is shown in Knauf et al., *J. Biol. Chem.* 263:15064–15070 (1988), and a discussion of POG conjugates is found in U.S. Pat. No. 4,766,106, both of which are hereby incorporated by reference in their entireties.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution or sterile saline, for example) which may include additional ingredients. Upon reconstitution, the composition is preferably administered to subjects using those methods that are known to those skilled in the art.

Insoluble inhibitors can be formulated by combination with one or more solubilizers. Preferred solubilizers include: ethanol; oils, such as corn oil; PEG; propylene glycol; and non-ionic surfactants. Preferred co-solvents have a molecular weight between 50 and 1,000, more preferably between 100 and 600. Preferably their concentration is between 1 and 75% w/w, more preferably between 10 and 50%. The concentration of ethanol is preferably between 0.1% and 20%, more preferably between 1 and 5%. Preferred non-ionic surfactants have a hydrophile-lipophile balance between 14 and 40, more preferably between 15 and 20, most preferably between 17 and 19. Preferably, the non-ionic surfactants have a molecular weight in the range between 100 and 250,000, more preferably between 4,000 and 200,000, most preferably between 6,000 and 150,000. Preferably, the non-ionic surfactants are effective in the concentration range of 0.005% to 10% w/v, more preferably in the range of 0.01 to 5% w/v, most preferably in the range of 0.05% to 2.5% w/v. Preferably, the non-ionic surfactants include those commonly used in the pharmaceutical, food, and cosmetic industries. Preferred non-ionic surfactants include: polyoxyethylene sorbitan fatty acid esters (i.e., Tweens), polyethylene glycol esters, polyethylene fatty acid esters, block copolymers of ethylene oxide and propylene oxide (i.e., Pluronics), ethylated fatty alcohol ethers (i.e., laureth-12), octylphenoxy polyethyoxy ethanol compounds (i.e., Tritons), and polyoxyethylated castor oil (i.e., Cremophor). These non-ionic surfactants can be produced by means known in the art or purchased from commercial suppliers.

Other non-ionic surfactants can be determined by using the following screening method. In this method a non-ionic surfactant is added to an effective concentration of insoluble inhibitor. The resulting solution is mixed or homogenized and allowed to stand for 24 hours at room temperature. If the inhibitor remains in solution, as measured by RP-HPLC, GC, or visual or spectrophotometric clarity, then the surfactant is useful to solubilize the inhibitor.

Having generally described what the applicants believe their invention to be, presented below are examples that are illustrative of the scope of the invention. It will be appreciated by those skilled in the art that the examples are not intended to be construed as limiting the invention to the materials and methods shown as there are numerous substitutions that can be made therein without departing from the scope of the invention.

EXAMPLE 1

Isolation and Identification of a TNFα Convertase

HL60 cells were obtained from the America Type Culture Collection (Rockville, MD) and grown in T-175 flasks containing RPMI 1640 medium supplemented with 20% fetal bovine serum (GIBCO) and L-glutamine. Batches totalling 3 liters of HL60 cells were grown to confluency and harvested. The cells were resuspended in approximately 120 ml of a hypotonic buffer and lysed by nitrogen cavitation (400 psi, 30 minutes at 4° C.). The homogenate was centrifuged at 10,000 x g for 10 minutes, and both the supernatant and the cell debris pellet were stored at −20° C.

HL60 cell debris from three batches of HL60 cell culture were thawed in 250 ml of 10 mM Tris pH 8.5 containing 0.5% NP-40, 5 mM EDTA, and 2 μg/ml leupeptin (DEAE buffer) and dialyzed for 4 hours in the same buffer. The protease inhibitors used during purification were shown to have no measurable effect on the convertase activity detected in HL60 lysates. Particulates were removed by centrifugation (10,000 x g, 10 minutes) and the sample fractionated by anion exchange chromatography on a DEAE Sepharose column (2.6×21 cm, Pharmacia) eluted with a 680-ml NaCl gradient from 0–0.8 M. Fractions containing TNFα convertase activity were identified throughout the purification using the $^{35}$S-proTNFα autoradiographic convertase assay. Pooled DEAE fractions were dialyzed into 20 mM sodium phosphate buffer, pH 6.5, containing 0. 1% NP-40, 1 mM EDTA, and 1 μg/ml leupeptin, divided into three equal portions and each portion was subjected to cation exchange HPLC on a 7.5×75 mm TSK-SP-5PW column (BioRad), eluted with a sodium chloride gradient from 0–0.6 M over 45 minutes. Fractions enriched in convertase activity were pooled and dialyzed into DEAE buffer containing 0.1% NP-40. The pooled material from the SP column was divided into three portions, and each was subjected to anion exchange HPLC on a (7.5×75 mm) TSK-DEAE-5PW column (BioRad), eluted with a sodium chloride gradient from 0–0.6 M over 45 minutes. The pool of convertase activity was further purified by RP-HPLC on a Vydac C4 column using an acetonitrile/0.1% TFA mobile phase.

This treatment provided a 1,000-fold purification, resulting in 20 μg of convertase (approximately 320 Units) at an 18% yield. Fractions from the RP-HPLC were tested for convertase activity and analyzed by SDS-PAGE. The fraction that contained convertase activity contained proteins having molecular masses of approximately 28–31 kD. The pooled convertase was analyzed by N-terminal protein sequencing, and a single amino acid sequence was obtained. The first 18 amino acids at the N-terminus proved to be identical to that of the serine protease PR-3. Native PR-3 was subsequently isolated from human neutrophils, using a minor modification of published procedures (Gabay, J. et al., *Proc. Nat'l Acad. Sci. USA* 86:5610 [1989]), and it was found to have the same activity as TNFα convertase in the proTNFα autoradiographic assay.

The identification of PR-3 as a TNFα convertase was further strengthened by N-terminal sequencing of cyanogen bromide cleavage fragments of the purified TNFα convertase, as well as amino acid composition, both of which agreed (within experimental error) with the published amino acid sequence of mature, active PR-3 (Campanelli et al., *J. Exp. Med.* 172:1709–1715 (1990).

EXAMPLE 2

Cloning and Recombinant Expression of Human PR-3

RNA was purified from HL60 cells and a cDNA library was constructed in the plasmid pGEM (PROMEGA, Madison, Wis.). Construction of the cDNA used C tailing of cDNA and G tailing of the vector, followed by ligation into the plasmid (*Gene Transfer and Expression,* 1990, pgs 114–135). Clones were screened using a unique oligonucleotide probe derived from the known sequence of myeloblastin (Bories et al. *Cell* 59:959–968 (1989)).

Sequencing of one clone, MY17, was performed using plasmid double-strand sequencing and the Sequenase kit and an automated Applied Biosystems (ABI) sequencer. The sequence in MY17 encoding preproPR-3 is shown in SEQ ID NO. 22. Novel features for the sequence include 5 nucleotide differences from the original publication by Bories et al., supra, and three nucleotide differences from the Campanelli et al., *J. Exp. Med.* 172:1709–1715 (1990) publication. Additional 5' sequence and an additional 5' methionine coding sequence were found. The two carboxyl terminal amino acids in the predicted PR-3 sequence obtained as described herein, arginine and proline, are the same as those prediced by Bories et al., supra, but differ from the glycine and proline sequence from Campanelli et al., supra.

Transient mammalian expression of PR-3 in mammalian cells was performed by cloning the 1.0 Kb HincIII-EcoRI PR-3 fragment from MY17 into the PstI site of SR-α vector. COS cells were transfected using the DEAE/Dextran method as described in, Kreigler, *Gene Transfer and Expression,* pp. 99–100, Stockton Press (1990). Transient expression revealed low levels of PR-3 expression in COS cells by Western blot analysis.

PR-3 was mutagenized in an attempt to optimize its expression in mammalian, bacterial and insect expression systems based on stratagies known in the art to be effective for expression of other recombinant proteins. The PR-3 gene in the pGEM vector was mutagenized using oligonucleotide directed mutagenesis. Various constructs were made.

A) PrePR-3 was made using an oligonucleotide that deletes the codons for amino acids at position −1 and −2 (glutamic acid and alanine, respectively). This gene can be removed from pGEM by EcoRI digestion, and the gene transferred to pCDL-SRα 296 (Takebe et al., *Mol. Cell. Biol.* 8:466 [1988]) for transient mammalian expression and pcDNA I for production of stable transfectants.

B) Met-PR-3 was made using an oligonucleotide that deleted the leader and added an ATG prior to the position 1 isoleucine of the mature protein. This gene can be removed from pGEM by EcoRI digestion, and transferred to the SR-α plasmid and pcDNA I for transient and stable mammalian expression. In addition, this construct was placed in pDG160, a λ cI-based bacterial expression vector at 8–12 nucleotides from the Shine-Dalgarno ribosomal binding site.

C) Another construct, the pAcCl3:Myo construct, was made so that the insect leader for cecropin B was placed before the position 1 isoleucine of the mature PR-3 protein. This was placed in the insect vector, pAcC13 for expression in Sf9 cells. A similar construct was made using the native PR-3 leader, but lacking the zymogen residues.

D) For optimization of bacterial expression, mutagenesis of the third nucleotide from a purine to a pyrimidine in the codons for the first 2–8 amino acids of delta signal PR-3 was performed using overlapping synthetic oligonucleotides and polymerase chain reaction amplification of the synthetic fragment. This fragment was cloned into the 5'Sma I site of PR-3, to decrease the GC content of the 5' RNA and facilitate expression.

E) For expression in *S. cerevisiae*, constructs similar in PR-3 related sequence to those described in A) and B) above were made. Unexpectedly, none of these constructs expressed significant amounts of recombinant PR-3, and in those which did express some PR-3 as detected by Western blot analysis, no activity was seen in PR-3 colorimetric protease assays. In some cases, trace amounts of insoluble rPR-3 were recovered, but in inactive disulfide-bonded aggregates. This material could not be refolded in vitro using standard refolding conditions.

F) The preferred host/expression system for producing a useful form of recombinant PR-3 comprised a native leader construct containing the zymogen residues expressed in Sf9 insect cells or a similar construct designed for expression in CHO cells or human 293 cells. The secreted zymogen was fully activatable (see, Examples 16 and 18).

EXAMPLE 3

Conversion of 26kD proTNFα to Mature TNFα

The vector pFVXM, on deposit with the American Type Culture Collection, Accession No. 67,103, was used to produce a vector pFVXM-TNFα6, which contains the DNA sequence that encodes the 26 kD TNFα species. To produce the latter vector, the plasmid pB 11 which contains the cDNA sequence that encodes the 26 kD TNFα species was treated with Pst I, which excises the coding sequence. The fragment was purified using standard electrophoretic techniques. Next, the vector pFVXM was treated with Pst I, and the Pst I fragment from pB 11 containing the 26 kD coding sequence was inserted into the polylinker region of the vector using standard techniques, as described above, to produce pFVX-TNFα6. pFVX-TNFα6 was used to produce the cell line TNFα 6.8, as described by Kriegler et al. 1988, or as described in U.S. Ser. No. 07/395,254, entitled "Cleavage Site Blocking Antibody to Prohormone Proteins and Uses Thereof," filed Aug. 16, 1989, now abandoned.

pFVXM and the plasmid pB 11 were both amplified in *E. coli* strain HB101. Ligation of the fragments was carried out using standard conditions. Plasmid DNA was isolated after the ligation procedure and the correct orientation of the TNFα encoding sequences was established by restriction analysis.

Plasmid DNA was prepared according to the procedure of Bimboim and Doty, as described in *Nucleic Acid Research*, 1:1513 (1979). The plasmid DNA was banded twice in cesium chloride density gradients, and exhaustively dialyzed against TE buffer consisting of 10 mM Tris, pH 8.0, and 1 mM EDTA.

TNFα 6.8 expresses both 26 kD and 17 kD TNFα . FIG. 4 shows the conversion of 26kD TNFα by convertase activity present in HL60 cells. In FIG. 4, Lanes A, B, and C show various controls: TNFα 6.8 cell lysate (A), 26 kD transcription/translation (B)and incubation (C) controls. Lanes D, E, and F show the conversion of transcription/translation generated 26 kD TNFα to predominantly 17 kD TNFα by convertase present in either HL60 S-1 cytosol uninduced (D) and induced (E) fractions, or a P-1 pellet fraction prepared from induced cells. G is a blank lane. The production of labelled 26kD TNFα by in vitro transcription/translation, and analysis by gel electrophoresis is described below in Example 4. Note that the S-1 cytosol or pellet fractions cause the near complete conversion of 26kD TNFα to a 17 kD species. FIG. 4 also shows, for comparative purposes, 26 kD and 17 kD TNFα in a lysate of TNFα 6.8 cells.

EXAMPLE 4

TNFα Convertase Assays

A. In Vitro Transcription/Translation Assay

A preferred assay procedure consists of in vitro transcription/translation to produce the 26 kD molecule, followed by treatment with convertase in the presence or absence of compounds being tested for convertase inhibitory activity. The procedure entails in vitro transcription/translation of the TNFα cDNA present in the pGEM vector. Thus, the sequence was removed from pB11 by Pst I digestion and was inserted into the Pst I site of pGEM-3 (obtainable from Promega Biotec, Madison Wis.). The resulting plasmid, termed pGEM-TNFα14, was amplified in *E. coli* using established techniques, and plasmid DNA was prepared according to the procedure of Bimboim and Doly, described above. Plasmid DNA was transcribed in vitro by linearizing it with Hind III, and the linearized plasmid templates were used to prepare capped transcripts with T7 RNA polymerase and an in vitro transcription kit supplied by Promega Biotec (Madison, Wis.). Transcription was performed using standard techniques as suggested by the manufacturer's instructions.

The mRNA produced above was translated in vitro in the presence of $^{35}$S-cysteine to produce $^{35}$S-cysteine-labelled 26 kD TNFα. A rabbit reticulocyte lysate translation kit was used, also supplied by Promega Biotec, and the conditions recommended by the manufacturer were followed.

$^{35}$S-cysteine-labelled 26 kD TNFα was used to assay for convertase inhibitors as follows. 25 μl of in vitro translated material was combined with 250 μl of solution containing convertase activity partially purified from uninduced HL60 cells, plus compounds to be assayed for inhibitory activity. The convertase was produced by harvesting 2×10$^9$ HL60 cells, disrupting the cells, and isolating S-1 (supernatant fluid from a 100,000 x g centrifugation) and P-30 (pellet from a 30,000 x g centrifugation) fractions totalling 18 and 6 ml, respectively. 250 μl of the P-30 fraction was used, although the S-1 fraction may also be used. The assay was carried out at 30° C. for 1 hour, essentially as described above. Next, the reaction mixture was immunoprecipitated with rabbit anti-human TNFα polyclonal antisera (produced from TNFα made in *E. coli*) and protein A Sepharose, pelleted and washed. The bound protein was eluted and electrophoresed using SDS-PAGE. The gel was fixed in 40% methanol, 10% acetic acid, soaked in Enlightening (Dupont), dried, and exposed to X-ray film which was subsequently developed. The gel electrophoretic profiles of 26 kD TNFα treated with HL60 convertase and varying dilutions of the potential inhibitory compound, revealed those compounds with inhibitory activity.

Using the above assay, it was determined that 3, 4-dichloro-isocoumarin and elastinal at concentrations of 100 pg/ml and 5 mg/ml, respectively, inhibit the convertase. It was also shown that (i-((3-((acetyloxyl)-7-methoxy-8-oxy-8-oxo-5-thio-1-azabicyclo [4.2.0] oct-2-en-2-yl) carbonyl) morpholine, S, S-dioxide, (6R-cis) at a concentration of 1 mM inhibits convertase activity. These results are shown in Lanes A, B, C, and D of FIG. 3A, respectively, immunoprecipitation of a cell lysate of the pFUXM-TNFα6 transfected cell line TNFα 6.8 (Kriegler et al., *Cell* 53:45 (1988), immunoprecipitation of in vitro transcribed/translated 26 kD TNFα, the effect of (1 -((3-((acetyloxyl)-7-methoxy-8-oxy-8-oxo-5-thio-1-azabicyclo [4.2.0] oct-2-en-2-yl) carbonyl) morpholine, S, S-dioxide, (6R-cis) on the conversion of 26 kD TNFα, and the conversion of 26 kD TNFα in the absence of (1-((3-((acetyloxyl)-7-methoxy-8-oxy-8-oxo-5-thio- 1 -azabicyclo [4.2.O] oct-2-en- 2-yl) carbonyl) morpholine, S, S-dioxide, (6R-cis). Lanes A and B of FIG. 3B show, respectively, immunoprecipitation of a cell lysate of the pFVXM-TNFα6 transfected cell line TNFα 6.8 (Kriegler et al., *Cell* 53:45 (1988), and immunoprecipitation of in vitro transcribed/translated 26 kD TNFα. Lanes C and D show the conversion of 26 kD TNFα in the presence and absence of 3,4- dichoro-isocoumarin, respectively. Lanes E and F show the conversion of 26 kD TNFα in the presence and absence of elastinal, respectively.

Figure 5:
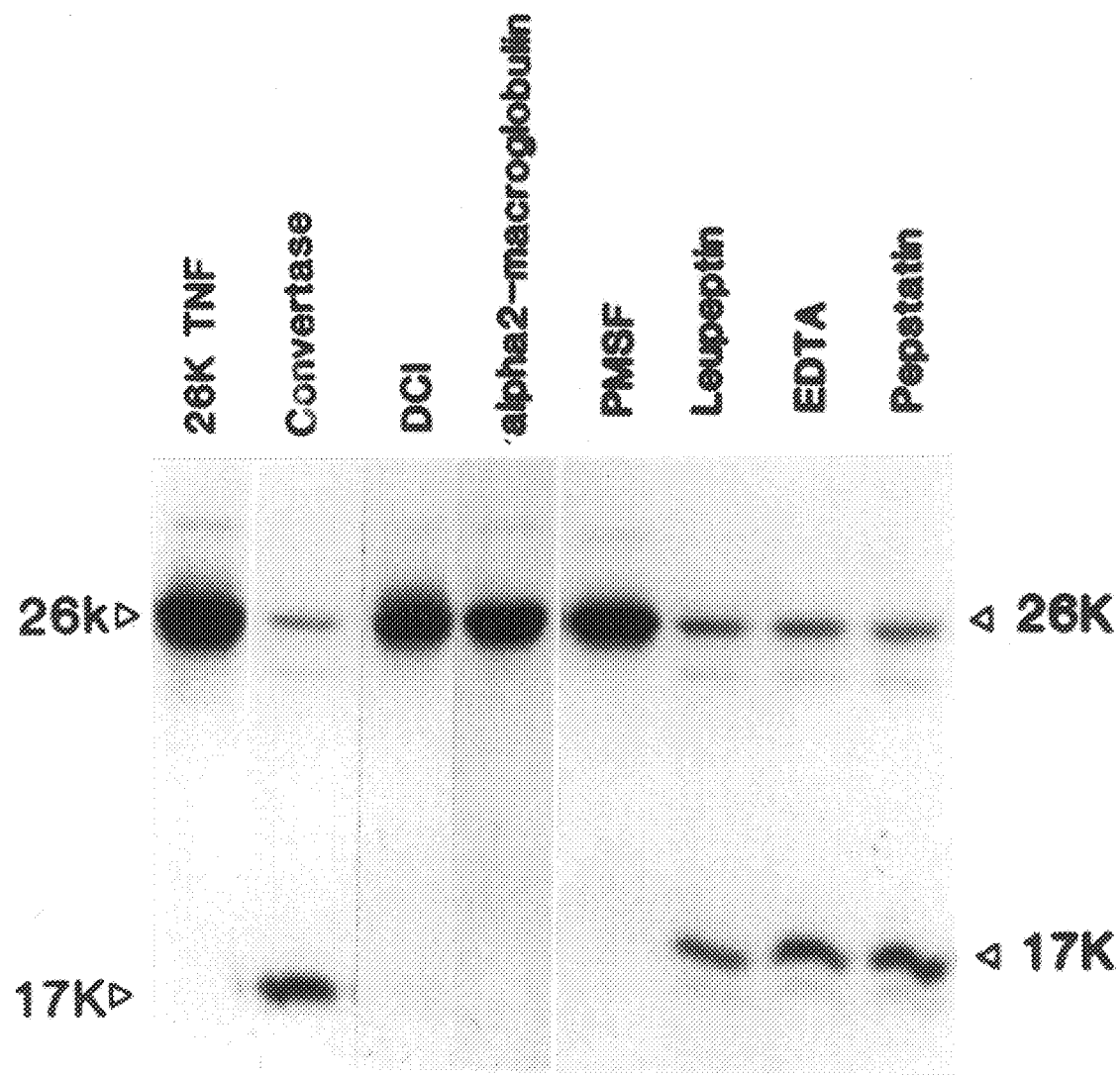
FIG. 5 is a photograph of an autoradiogram showing the inhibition of conversion of 26 kD TNFα to its lower molecular weight forms by purified human PR3 from HL-60 cells with various serine protease inhibitors.

The above assay was also used with purified native PR-3 from human neutrophils to test a variety of proteinase inhibitors for their ability to inhibit TNFa convertase activity, as shown in FIG. 5. Purified PR-3 (0.3 μg/ml) was preincubated for 30 minutes with the following inhibitors prior to addition of $^{35}$S-labelled 26 kD-TNFα, and then assayed as described above: DCI (45 μM), α-2-macroglobulin (1 mg/ml), PMSF (20 μM), leupeptin (2 μg/ml), EDTA (10 mM), or pepstatin (2 μg/ml). The first three of these inhibitors showed significant inhibitory activity.

B. Cell-Based Assays

The 26 kD form of TNFα can also be produced by stimulated monocytes, as described by Kriegler et al., *Cell* 53:45 (1988).

Briefly, human monocytes are purified from human blood by centrifugation, and subsequently enriched based on the adherence of monocytes to cell culture dishes. Centrifugation consists of purifying the monocytes through Ficoll-hypaque and percoll (49.2%), obtainable from Pharmacia. The manufacturers' recommended procedures were followed. Next, the mixture of cells resulting from the centrifugation step, consisting of monocytes and lymphocytes, are plated onto tissue culture dishes containing RPMI media supplemented with 20% fetal calf serum. The dishes are incubated for 30 minutes at 37° C. after which they are extensively rinsed with the same media. This treatment removes non-adherent lymphocytes and leaves only adherent monocytes.

Monocyte 26 kD TNFα is radiolabelled as follows. The monocytes are incubated for 3 hours at 37° C. in RPMI media supplemented with 20% fetal calf serum. The medium is then replaced with cysteine-deficient medium (RPMI containing 5 % v/v dialyzed fetal calf serum) and the cells are induced with 100 ng/ml lipopolysaccharide and 10 pg/ml phorbol myristate acetate for 30 minutes at 37° C. The latter two compounds induce the expression of TNFα. The serum is dialyzed prior to use to remove any cysteine present. After the 30-minute incubation period, 100 μCi $^{35}$S-cysteine is added, and the cells are radiolabelled for 3 hours at 37° C., after which they are lysed and used to assay for convertase activity. The steps for carrying out the assay, as well as identifying inhibitors of the convertase, are similar to those described above. Other cell lines, such as THP-1 human monocyte cells can be used for such assays. The assay signal can be based on endogenous TNFα convertase activity or supplemented with recombinant TNFα convertase.

C. Colorimetric Assay for Convertase Inhibition

TNFα convertase inhibition can also be measured by a colorimetric assay. In this type of assay, the actual activity of TNFα convertase is measured directly using a colorimetric TNFα convertase substrate. By "colorimetric TNFα convertase substrate" is meant a compound that is cleaved by a TNFα convertase to release a compound that displays an increase in absorbance of light of a specific wavelength. One such substrate is Boc-Ala-ONp (Bachem Bioscience, Inc., Philadelphia, Pa.). Other potentially useful substrates can be predicted from the structure of TNFα convertase and other serine proteases. Although the example herein uses purified native PR-3 as the TNFα convertase, it is contemplated that recombinant PR-3 or other TNFα convertases can be used in this assay as well.

Peptide diphenyl phosphonate inhibitors were synthesized and stored as lyophilized solids as described in Oleksyszyn and Powers, *Biochem* 30:485–493 (1991). Inhibitor solutions (10 mg/ml) were prepared in 100% dimethyl sulfoxide (DMSO) and diluted into aqueous buffers upon initiation of the experiments. 3,4, dichloro-isocoumarin was purchased from CalBiochem. Purified PR-3 (10 μl, 0.1 mg/ml) was mixed with varying concentrations of protease inhibitor (400 μl final volume) in 20 mM sodium phosphate buffer, pH 7.0, containing 0.1 M sodium chloride. Aliquots (40 μl) were removed at selected times and diluted 1/10 into a colorimetric assay for convertase, containing 0.5–1 mM Boc-Ala-ONp (prepared fresh from a 50 mM stock in 100% methanol) in 0.02 M sodium phosphate buffer, pH 7.0, 0.1 M sodium chloride. The increase in absorbance was monitored at 347 nm on a Hewlett Packard 8450A spectrophotometer, and using an extinction coefficient of $5.5 \times 10^3$ M$^{-1}$cm$^{-1}$ to calculate units of enzyme activity.

EXAMPLE 5

Peptide Diphenyl Phosphonate Inhibitors of TNFα Convertase

Several peptide diphenyl phosphonates were tested for inhibitory activity: Boc-Val-Pro-Val-p(OPh)$_2$ (VPV), Boc-Ala-Pro-Val-p(OPh)$_2$ (APV), Boc-Ala-Gln-Ala-p(OPh)$_2$ (AQA), and Boc-Leu-Ala-Gln-Ala-p(OPh)$_2$ (LAQA). The peptides were prepared by chemical synthesis using the Merrifield method described above and the diphenyl phosphonates were prepared according to the method similar to the one shown in Oleksyszyn et al., supra.

The peptide diphenyl phosphonates were tested in the colorimetric assay described in Example 3, for inhibition of TNFα convertase/PR-3 activity. The results are shown in FIG. 6. VPV and APV at 35 μM demonstrated inhibitory activity. AQA and LAQA (SEQ ID NO:26) at 35 μM showed marginal, if any inhibition at the concentrations tested. Dichloro- isocoumarin (DCI) at 95 μM showed 100% inhibition in the assay.

EXAMPLE 6

TNFα Mutein/Antibody/Peptide Inhibitors of Convertase Activity

The following compounds will have convertase inhibitory activity and can be prepared as follows. These compounds may be tested for inhibitory activity as described in Example 4 above.

A. Anti-Convertase Antibody

Monoclonal or polyclonal antibody is prepared that binds to the convertase and thereby sterically prevents the convertase from binding to 26 kD TNFα or otherwise neutralizes the enzymatic activity of the convertase. The procedure for the production of antibody consists of immunizing an appropriate host animal with a membranous fraction of HL60 cell producing TNFα convertase. Alternatively, purified TNFα convertase may be used from native or recombinant sources. For example, PR-3 from human neutrophils may elicit anti-TNFα convertase antibodies. A sufficient amount of material should be used to elicit an immune response, and usually this will consist of between 10 pg to 10 mg per kilogram of body weight. Immunization may be conducted with adjuvant, by way of example, Freud's incomplete adjuvant in a biologically acceptable buffer, as is known in the art. Methods for the production of antibodies are found in Harlow et al., *Antibodies, A Laboratory Manual*, Cold Spring Harbor Laboratory, Cold Spring Harbor, N.Y. (1988). The best immunization route can be determined experimentally, and the primary immunization may be followed by one or more secondary immunizations depending on the strength of the immune response to the initial immunization. The presence of neutralizing anti-convertase antibody in the sera may be detected using the convertase assay described above wherein antisera is present in the assay mixture. Inhibition of the conversion of the 26 kD TNFα species to a species having the molecular weight of mature TNFα indicates the presence of a neutralizing antibody. Controls are conducted to insure that antisera from non-immunized animals is not inhibitory. Polyclonal antibody may be purified as described below.

Monoclonal antibody to the convertase may be produced using either in vivo or in vitro immunization techniques, and sensitized lymphocytes resulting therefrom can be used to prepare hybrid cell lines that secrete the appropriate monoclonal antibody. Rodent, preferably of murine origin, or human antibody is most preferred. The in vitro immunization procedure involves sensitizing lymphocytes to the convertase by immunizing either mice or humans, and isolating therefrom the antibody-secreting cell fraction and immortalizing the cells therein by one of several procedures. An alternate embodiment is to isolate lymphocytes that have already been sensitized to the convertase from septic patients or Wegener's granulomatosis patients as described above.

(i) Murine Antibody

For in vivo immunization of mice, the procedure of Kohler and Milstein described in *Nature* 256:495 (1975) may be followed, or modified procedures such as those shown by Fendly et al., *Hybridoma* 6:359 (1987); Buck et al., *In Vitro* J1:377 (1988). In vitro techniques are generally described by Luben, R. and Mohler, M., *Molecular Immunology* 17:635 (1980); Reading, *Methods in Enzymology* 121 (Part One): 18, or Voss, *Methods in Enzymology* 121:27 (1986).

Mice are immunized with 1 mg/ml of a membranous fraction of HL60 cells previously shown to be positive for convertase activity. Alternatively, a smaller amount of purified TNFα convertase may be employed. The immunization is carried out in complete Freund's adjuvant. Two additional immunizations, or boosts, are performed at monthly intervals without adjuvant, and one month after the last boost the mice are given an I.V. boost of 10 pg of membranous material. Three days after the I.V. boost, mice are sacrificed, their spleens removed, and the splenocytes isolated and fused to an immortalized, drug-selectable myeloma partner cell line. Numerous such myeloma lines are known in the art, most of which are incapable of growth in HAT supplemented cell culture media. A typical myeloma cell line is SP-2/0 Ag 14. Thus, the hybridomas are formed by combining splenocytes and myeloma cells in a 5:1 ratio, which generally consists of $2 \times 10^6$ myeloma cells to $1 \times 10^7$ splenocytes. The cell mixture is pelleted, media removed and fusion affected by the addition of 1.0 ml of 40% (v/v) solution of polyethylene glycol 1500 by dropwise addition over 60 seconds at room temperature, followed by a 60-second incubation at 37° C. To the cell suspension with gentle agitation is added 9 ml of Dulbecco's Modified Eagles medium over 5 minutes. Cell clumps in the mixture are gently resuspended, the cells washed to remove any residual PEG and plated in microtiter plates at about $2 \times 10^5$ cells/well in DMEM supplemented with 20% fetal calf serum. After 24 hours, the cells are fed a 2 X solution of hypoxanthine and azaserine selection medium.

Medium from wells that exhibit positive cell growth may be screened for neutralizing monoclonal antibody to the convertase. Preferred assays are the convertase assays described above, wherein medium sought to be tested for anti-convertase antibody activity is present in the assay. More preferred is to combine culture supernatants from 3–8 microtiter wells, and assay the mixture. If the mixture is positive, then medium from each well may be assayed independently to identify the secreting hybridoma(s). Many assays are known in the art and can detect soluble, or non-soluble antigens, and are shown by Langone, J. and Van Vinakis, H., *Methods in Enzymology*, 92 Part E (1983).

Regardless of whether the antibody is polyclonal or monoclonal, it is desirable to purify the antibody by standard techniques as are known in the art, or described by Springer *Monoclonal Antibodies* 194 (1980), (Eds. Kennett, T. McKeam and K. Bechtol, Plenum Press, New York). Generally this consists of at least one ammonium sulfate precipitation of the antibody using a 50% ammonium sulfate solution. Antibody affinity columns may also be used.

(ii) Human Monoclonal Antibody

Peripheral blood lymphocytes are isolated from septic patients, and then infected with Epstein-Barr virus. The infected lymphocytes are then immortalized by fusion to a selectable myeloma cell line, and the hybrid cell lines so generated isolated and characterized as to antibody production.

More specifically, mononuclear cells are separated on Ficoll-hypaque (Pharmacia), and monocytes depleted from the mixture by adherence to plastic. Standard laboratory techniques were utilized to effect these procedures. Next, nonadherent cells are enriched for antibody producers by antigen-specific panning. Panning is a technique generally known in the art, and involves incubation of a population of antibody-secreting cells on a plastic surface coated with the appropriate antigen. Those cells that express antibody on their surface bind antigen, and consequently adhere to the plastic surface, whereas cells that do not express cell surface antibody, do not adhere and can be removed by washing. Thus, specific antibody-secreting cells are enriched for by this technique.

More specifically, 6-well plates (Costar) are coated with purified TNFα convertase or a membrane fraction containing convertase prepared from either induced or uninduced HL60 cells, as described above, such that 150 pg of membranous material is coated per well in phosphate buffered saline at 40° C. overnight. The wells are blocked after the overnight incubation period with phosphate buffered saline containing 1% bovine serum albumin for at least 1 hour at 40° C., and subsequently washed with phosphate buffered saline/BSA. Next, $10^7$ lymphocytes in 1 ml of PBS/BSA are added to each well of the six well plates. The lymphocytes are allowed to incubate on the plates for 70 minutes, after which any nonadherent cells are removed by aspiration. The adherent cells are incubated with cell culture medium (IMDM) (Sigma Chemical Co., St. Louis, Mo.) containing 10% fetal calf serum.

The adherent cells are subjected to Epstein-Barr virus transformation by adding an equal amount of culture media obtained from growing the Epstein-Barr virus infected marmoset cell line, B95-8, and thus containing the virus, to media bathing the adherent cells. The cells are cultured in this environment at 37° C. for 3 hours, and in this way the lymphocytes in the adherent cell population are subjected to Epstein-Barr infection. Following the infection period, the cells are washed and plated onto 96 well microtitre plates at a density of about $10^4$–$10^5$ cells/well in IMDM medium, plus 10% fetal calf serum, and 30% conditioned medium. The latter is derived from a lymphoblastoid cell line, preferably W5. The medium also contains $5 \times 10^{-5}$ M 2-mercaptoethanol, 50 µg/ml gentamycin sulfate (Sigma), and 600 ng/ml cyclosporine A (Sandimmun, Sandoz, Basel, Switzerland).

After about 14 to 21 days of incubation, cell culture supernatants are combined and screened for TNFα convertase-neutralizing activity as described above. Positive hybridomas are subcultured at low density, retested for neutralizing antibody, and grown up and fused to the cell line F3B6 using polyethylene glycol and the plate fusion technique described by Larrick, *Human Hybridomas and Monoclonal Antibodies* (1985), E. G. Engleman, S. K. H. Foung, J. W., Larrick, and A. A. Raubitschek, Editors, Plenum Press, New York, page 446. F3B6 is a heteromyeloma cell line that is sensitive to growth in media containing 100 µM hypoxanthine, 5 µg/ml azaserine, and 5 µM ouabain. Finally, the resulting hybrids are again screened to ensure that they produce neutralizing anti-convertase antibody.

B. 26 kD Muteins 26 kD TNFα muteins are described that may compete for binding to the convertase, thereby inhibiting or reducing its activity. The preferred mutein embodiments are those having valine at positions 1 and/or 13; or alanine at position −1 and/or proline at position 12, replaced or deleted. The muteins are constructed using a modification of the site-directed mutagenesis gapped-duplex method or using PCR methods described below.

The following solutions/buffers are used to perform the desired procedures: 5x gapped-duplex buffer (GDB) consisting of 0.938 M KCl, 0.063 M Tris, pH 7.5; 10 x PEL consisting of 1.0 M KCl, 0.30 M Tris, 0.15 M MgCl$_2$, 0.02 M DTT, pH 7.5; 10 X KB consisting of 0.50 M Tris, 0.10 M MgCl$_2$, 0.05 M DTT, 0.001 M EDTA, pH 8.0; a solution containing 0.25 mM dCTP, dATP, dGTP, dTTP, made fresh from 10 mM stocks; an ATP solution consisting of 0.1 M ATP made by dissolving 60 mg of ATP in 0.80 ml of H$_2$O and adjusting the pH to 7.0 with 0.1 M NaOH in a final volume of 1.0 ml with H$_2$O; 20% PEG/2.5 M NaCl; 3.0 M NaOAc; and TE-saturated phenol.

Various bacterial strains and phage are employed to yield the desired muteins and these are BMH 71-18, JM103 for growing phage strains; HB2154: MutL, Su⁻, made competent for DNA transformation; and HB2151: Su⁻, used as lawn cells during transformation; M13 GAP, the double-stranded DNA is used for the formation of the gapped-duplex; and M13mp 19amber, the 26 kD TNFα target DNA is cloned in this vector, and single-stranded ssDNA isolated for the formation of the gapped-duplex.

Phage are infected into an appropriate bacterial strain, grown, and titered as follows. In making a large-scale preparation of either phage for ssDNA or cells for dsDNA, or RF DNA, the same infection protocol is used.

Plaque-purified phage is produced using standard techniques. Briefly, this consists of streaking phage supernatants on agar plates, followed by careful overlay with 4.0 ml of soft agar and 100 μl of fresh overnight culture of BMH 71-18. Next, isolated plaques are picked and incubated with a 1:50 dilution of fresh overnight culture of BMH 71-18 in R26 or R17+10 mM MgCl$_2$ with shaking at 37° C. for 4.5–6 hours. R17 (N-Z amine broth) consists of 10 g N-Z amine type A, 5 g NaCl with H$_2$0 to 1 liter, while R26 consists of 8 g tryptone, 5 g yeast extract, 5 g NaCl, with water to 1 liter (YT broth). The phage stock is titered, and phage infected into bacteria at a multiplicity of infection (MOI) of 10. After incubating the culture with shaking at 37° C. for 5 hours the cell suspension is pelleted, and the supernatant saved for ssDNA isolation, and the cells for RF isolation. RF DNA is isolated using established plasmid DNA isolation techniques, while ssDNA is isolated as follows.

250 ml of phage supernatant is centrifuged at 10,000 X g for 30 min. after which 200 ml of the supernatant is decanted, followed by adding 50 ml of 20% PEG/2.5 M NaCl to the supernatant fluid, and incubation overnight at 4° C., or on ice for 30 minutes. This mixture is centrifuged as above, and the supernatant decanted and discarded. The bottle is spun again to pellet the phage precipitate along the sides of the bottle, and the remaining fluid is aspirated with a Pasteur pipette. The pellet is resuspended in 5.0 ml of 1 x TE, and stored at 4° C., after which 0.5 ml of is extracted twice with 0.5 ml of TE saturated phenol. To the aqueous layer is added 0.050 ml of 3.0 M NaOAc and 1.0 ml 95% ethanol. The mixture is placed in a dry ice bath for 10 min., and centrifuged for 10 min. in a microfuge at 4° C. The pellet is dried and resuspended in 200 μl of 1 x TE. This material may be stored in 0.05 ml aliquots at −20° C. until used in the mutagenesis of 26 kD TNFα.

The following deletions and substitutions in Table 1 are preferred proTNFα muteins. These muteins can be prepared using appropriate oligonucleotides by methods known in the art.

TABLE 1

| Deletions |
|---|
| ΔVAL 1 |
| ΔVAL13 |
| ΔPRO12 |
| ΔVAL1 + ΔPRO12 |
| ΔVAL1 + ΔVAL13 |
| ΔALA-1 |
| ΔALA-1 + ΔPRO12 |

| Substitutions |
|---|
| (VAL1→ALA1) + (VAL13→ALA13) |
| (VAL1→GLY1) + (VAL13→GLY13) |
| (VAL1→LEU) + (VAL13→LEU13) |
| (VAL1→MET) + (VAL13→MET13) |
| (VAL1→PHE1) + (VAL13→PHE13) |
| (VAL1→HIS1) + (VAL13→HIS13) |
| (VAL1→THR 1) + (VAL13→THR 13) |
| (ALA-1, VAL 1 → GLN-1, HIS 1) + (PRO 12, VAL 13 → GLN 12, HIS 13) |
| (ALA-1, VAL 1 → GLN-1, HIS 1) + (PRO 12, VAL 13 → SER 12, THR 13) |

The oligonucleotides are kinased using the following reaction solution and conditions: 3 μl 10 x KB buffer, 3 μl 10 mM ATP (1:10 dilution of 0.1 M ATP stock), 2 μl mutagenic oligonucleotide (100 pmole/μl), 21 μl H$_2$0, and 1 μl polynucleotide kinase (10 Units/μl). The reaction is run at 37° C. for 45 minutes, and then at 65–68° C. for 5 minutes. Next, 24 μl of the kinased oligonucleotide is diluted with 56 μl of H$_2$O to give 2 pmole/μl.

The gapped-duplex is formed as described below, followed by annealing the oligonucleotides. The following reagents are combined in a total volume of 40 μl: 8 μl 5 X GDB buffer, 0.50 pmole ssDNA, and 0.10 pmole Hind II linearized M13 GAP RF DNA. 10μl is removed for future use, and the remaining 30 μl is treated sequentially as follows: 100° C. for 3 minutes, 65° C. for 5 minutes, followed by cooling to room temperature for 30 minutes, and then placing the reaction mixture on ice. Next, 10 μl of gapped-duplex and 10 μl of control ungapped material is subject to electrophoresis on agarose gel to check gapped-duplex formation. If the gel shows the presence of a third band, the gapped-duplex has formed, and the kinased oligonucleotides can be annealed to the duplex by combining 16 μl of gapped-duplex reaction mixture and 4 μl of diluted kinased oligonucleotide, then heating the mixture to 65° C. for 3 min, followed by cooling to room temperature for 20 min.

The heteroduplex is completed by the appropriate extension and ligation reactions consisting of combining the following reagents in a total volume of 40 μl: 10 μl gapped-duplex and primer, 4 μl 10 x PEL buffer, 4 μl dNTP's (0.25 mM solution made from 10 mM stocks, 3 μl ATP (10 μl of 0.1 M ATP stock+1490 μl H$_2$O=0.662 mM), 17 μl H$_2$0, 1 μl Klenow (5 u/μl), and 1 μl T4 DNA ligase (0.6 Weiss U/μl, diluted stock with 1 x PEL). The reaction is conducted at 16° C. for 2 hours, followed by transformation of 10 μl of the extension/ligation mixture into 200μl of thawed competent HB2151 cells. The cells are kept on ice for 30 minutes, and then 42° C. for 1.5 minutes, followed by plating various volumes of the transformation mix (e.g., 50 μl, 10 μl, etc.) with 100 μl of fresh overnight culture of HB2151 cells+3.0 ml of soft agar.

The resulting plaques are screened using the plaque hybridization procedure. While a variety of such procedures are known, a description of the preferred procedure follows. Plates are replicated onto duplicate nitrocellulose filter papers (S & S type BA85) and the DNA fixed to the filter by sequential treatment for 5 min. with 0.5 N NaOH plus 1.5 M NaCl; 1.0 M NaCl plus 0.5 MTris-HCl pH 7.4; and 2 x SSC (standard saline citrate). Filters are air-dried and baked at 80° C. for 2 hours in vacuo.

The duplicate filters are prehybridized at 55° C. for 2 hours with 10 ml per filter of DNA hybridization buffer, 5 x SSC, pH 7.0, 5 x Denhardt's solution (polyvinylpyrrolidone, plus Ficoll and bovine serum albumin; 0. 1% of each), 50 mM sodium phosphate buffer at pH 7.0, 5 mM EDTA, 0.1 % SDS, and 100 pg/ml yeast RNA. The prehybridization buffer is removed and the samples hybridized with the appropriate kinased probe, specifically, kinased oligonucleotides as described above, under conditions which depend on the stringency desired. About $2 \times 10^6$ cpm/ml total is used. Typical moderately stringent conditions employ a temperature of 42° C. plus 50% formamide for 24–36 hours with 1–5 ml/filter of DNA hybridization buffer containing probe. For higher stringencies high temperatures and shorter times are employed. The preferred hybridization conditions consist of hybridizing the probes to the filters in 5 x SSC, Denhardt's solution, 50 mM $NaPO_4$, pH 7.0, 5 mM EDTA, 0.1 % SDS, and 100 mg/ml yeast RNA at 10° C. below the melting temperature (Tm) of the oligonucleotide used in the screening. Next, the filters are washed twice, 30 minutes each wash, at room temperature with 2 x SSC, 0.1% SDS, then washed once with 2 x SSC and 0.1% SDS at 5° C. below the Tm of the oligonucleotide used to screen, and air-dried. Finally, the filters are autoradiographed at −70° C. for 36 hours. Autoradiography reveals those plaques containing the virus that carries the muteins of interest.

In addition to constructing muteins wherein valine at position 1 and/or 13 have been deleted or substituted, large deletion muteins may be produced that encompass the two predominant cleavage sites of 26 kD TNFα. One such mutein lacks the amino acids spanning the region −9 to +14, as shown in FIG. 1. This mutein was constructed using the materials and methods described above and the oligonucleotide, CP375 which has the following sequence and set out as SEQ ID NO: 18:
5' GTTTGCTACAACATGGAGGTCCCTGGGGGA 3'

C. Protein/Peptide Inhibitors

Peptides having the amino acid sequences set forth in SEQ ID NOS. 5, 6, 7, and 8 are synthesized by the solid-phase method, described in detail by Merrifield *Science* 232:341–347 (1985). A Biosearch 9500 automated peptide machine is used with hydrogen fluoride cleavage, and purification by preparative HPLC using a Waters Delta Prep 3000 instrument, on a 15–20 mm Vydac C4 PrepPAK column.

TNFα convertase inhibitory activity of these peptides is shown by performing any of the various assays described above in the presence of varying amounts of each peptide. Gel electrophoresis and Western blotting of the reaction mixture shows an inhibition of conversion of the 26 kD proTNFα to the 17 kD mature form.

By way of additional example, Ala-Gln-Ala-Val-Arg-Ser-Ser-Ser (SEQ ID NO:27) was synthesized as described above and tested in the Boc-Ala-ONp colorimetric assay with PR-3. However, this peptide did not inhibit convertase activity significantly at 50 µM.

EXAMPLE 7

TNFα Convertase Inhibitory Activity of DCI in L929 Mice 3,4 dichloroisocoumarin (DCI) specifically suppresses the release of TNFα but not IL-6 from mouse macrophages as shown below.

Release of TNFα by macrophages after stimulation by LPS is a major source of TNFα in the host. In these studies peritoneal macrophages were purified by adhesion, cultured in 24 well plates, and LPS was added to induce secretion of TNFα. Analysis of the kinetics of TNFα release showed a maximal peak at 3 hours. DCI was then added in dimethyl sulfoxide vehicle to cultures. The control cultures had DMSO alone added in equivalent concentrations. Supernatants were collected and assayed for TNFα and IL-6. Results show that TNFα secretion is markedly suppressed with DCI but not control with vehicle. In contrast the IL-6 response was not significantly altered, thus ruling out a nonspecific toxic effect (see Table 2).

TABLE 2

| Sample | TNFα (ng/ml) | IL-6 (pg/ml) |
| --- | --- | --- |
| DMSO control | 6.9 | 299 |
| DCI 20 (µg/ml) | 0.05 | 189 |

Adherent peritoneal macrophages ($10^6$/ml) were cultured with LPS and either DMSO or DCI DMSO. Cells were cultured for 3 hours and supernatants were collected. TNFα was measured by ELISA and IL-6 by B9 bioassay.

Since DCI was able to specifically suppress LPS induced TNFα secretion in murine macrophages, the therapeutic effect of administration of DCI to mice injected with LPS was examined.

Stability and formulation studies showed that DCI when dissolved in corn oil was stable and retained serine protease inhibitor activity. Injection of DCI/oil into mice showed an LD 50% at a dose of 1 mg/ml. This represented a maximal tolerated dose of DCI that could be administered.

Figure 7:
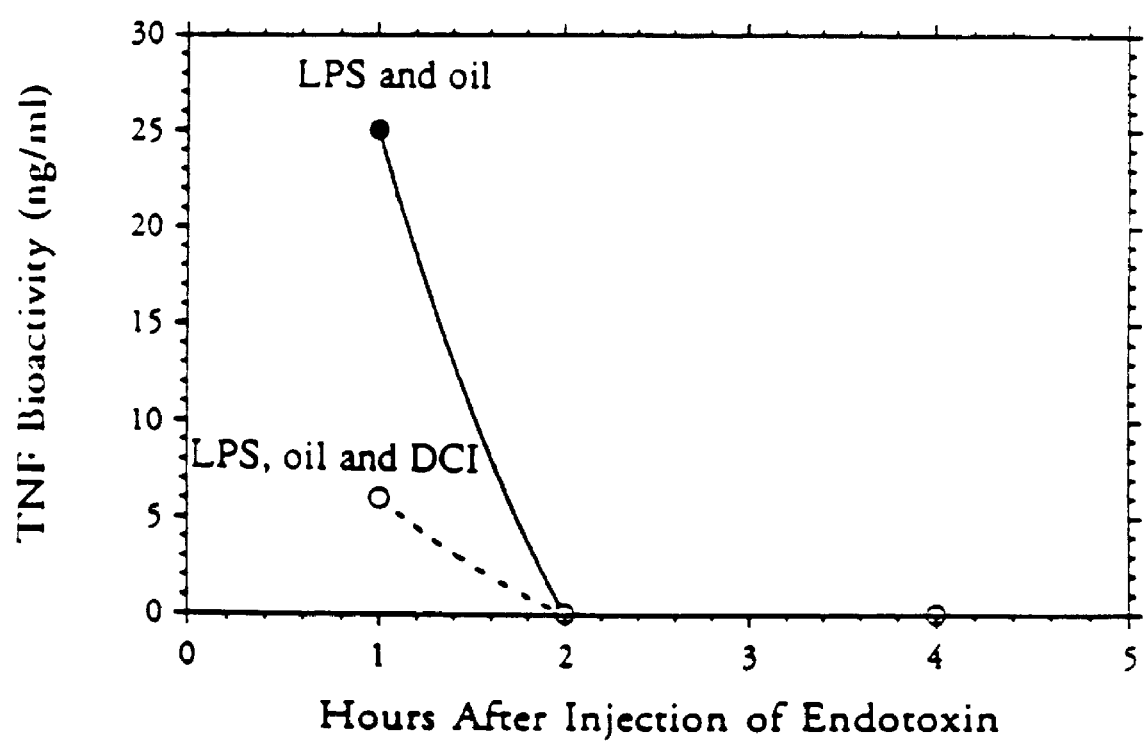
FIG. 7 is a graph showing the effect of prophylactic treatment of mice with a TNFα convertase inhibitor prior to lethal injection with LPS: circulating serum TNFα levels are decreased.

The kinetics of induction TNFα and IL-6 in mice injected with a lethal dose of LPS was studied. TNFα showed a sharp peak at 2 hours with return to baseline within a few hours. IL-6 showed a slower gradual increase. Injection of DCI 1 hour before the LPS dose resulted in a marked inhibition of serum TNFα secretion (see FIG. 7). Also, there was a delayed increase in TNFα measured up to the 6-hour time point. This was true for both immunoreactive mouse TNFα measured by ELISA and bioactive TNFα measured by lysis of L929 cells. IL-6 levels were not reduced by this therapy.

Figure 8:
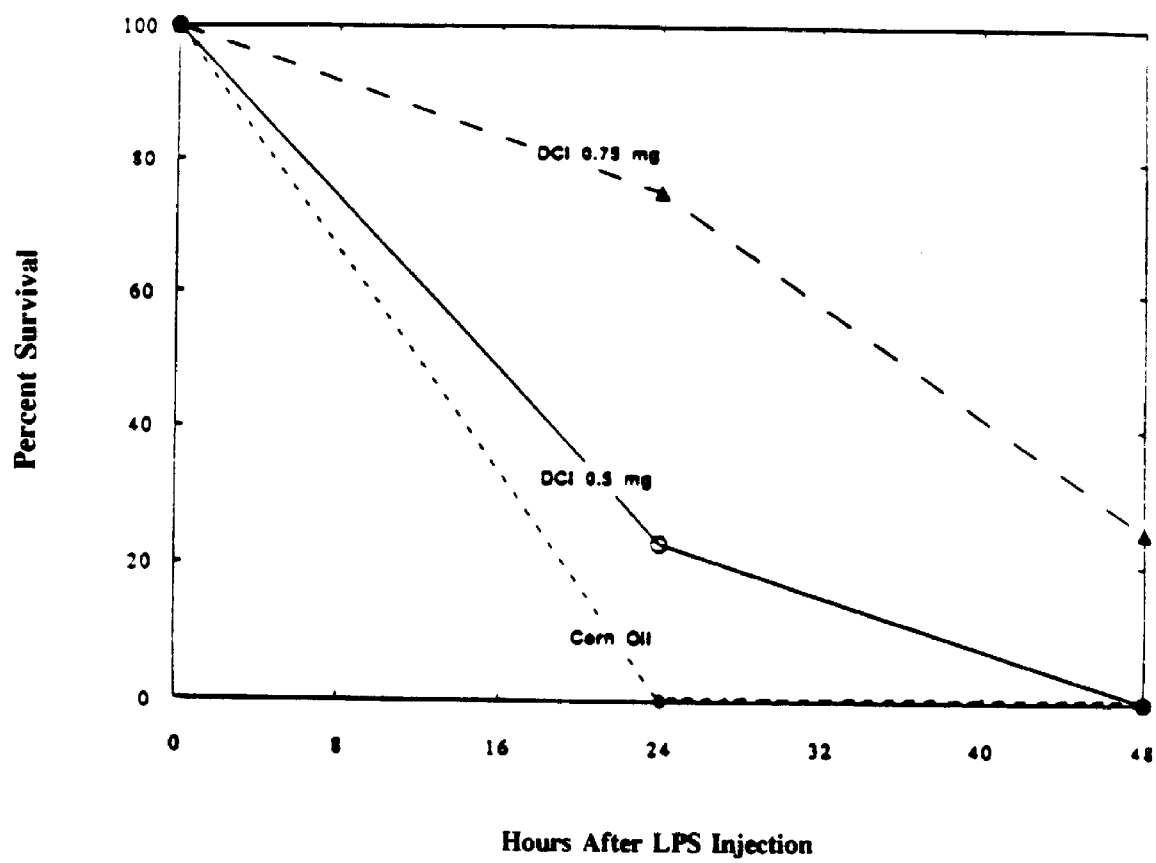
FIG. 8 is a graph showing the effect of prophylactic treatment of mice with a TNFα convertase inhibitor prior to lethal injection with LPS: survival is prolonged.

The effect of DCI on survival of mice injected with a dose of LPS that results in 100% death of animals by 24 hours was also investigated. Results show that prophylactic therapy with DCI could prolong survival of mice (see FIG. 8). There was a dose response relationship noted by 0.75 mg of DCI being more effective than 0.5 mg.

In summary, these studies suggest that DCI is able to inhibit LPS induced TNFα production by murine macrophages in vitro. This specificity of inhibition of TNFα could also be seen in animals injected with a lethal dose of LPS. Furthermore, the survival of animals was prolonged with DCI therapy in a dose related manner. These studies suggest that DCI (a serine protease inhibitor) may be beneficial in a sepsis model in prolonging survival by suppression of the systemic release of TNFα.

EXAMPLE 8

Protective Effect of TNFα Convertase Inhibitors in the Treatment of Septic Shock Compounds that are effective inhibitors of convertase activity are shown to prevent sepsis in a baboon model system as follows. Anti-TNFα convertase antibody, murine, human, or recombinant, at a concentration of 5 mg/kg is administered in a single I.V. bolus 60 minutes before the animals are challenged with a lethal dose of E. coli, and 2 mg/kg simultaneously with the E. coli challenge. The antibody is administered in a physiologically balanced salt solution, and about $4\times10^{10}$ E. coli organisms are used. The E. coli dose is infused over a 2 hour period. Animals that receive the antibody are protected for at least 7 days, whereas control animals that are administered only the balanced salt solution expire within about 16 to 32 hours.

Similar protection may be attributable to the TNFα muteins which act as convertase inhibitors shown in Example 6. The muteins are administered at a concentration of 5 mg/kg in a single I.V. bolus 60 minutes before the animals are challenged with $4\times10^{10}$ E. coli organisms. The baboons also receive 2 mg/kg of the muteins simultaneously with the E. coil challenge.

Finally, peptides, for example the peptide set out in SEQ ID NO. 5, are tested as described above and are expected to yield similar protective effects.

The baboon system is particularly useful for testing small molecular weight, orally active inhibitors identified in screens with TNFα convertase. The baboon system is the preferred animal model for confirmation of preclinical results because proTNFα is the only 26 kD proTNFα that closely resembles human proTNFα at the putative cleavage.

EXAMPLE 9

Modelling of Human PR-3 Onto Human Elastase Three Dimensional Structure and Use of Inhibitor-Enzyme Complex Models to Predict Novel PR-3 Inhibitors A model for the TNFα convertase, PR-3, was constructed by determining structural similarities shared between PR-3 and other serine proteinases. A 3-D model of the enzyme was generated by first determining that the PR-3 sequence shared a high degree of sequence homology with human neutrophil elastase (HNE). The three-dimensional structure of HNE (Navia et al., *PNAS (USA)* 86:7 (1989), was used as a scaffold to build a three dimensional representation of the PR-3 protein using the computer program Homology (Biosym, San Diego). The model was further refined by two rounds of minimization using the computer program Discover (Biosym, San Diego). The design of potential inhibitors that are specific for PR-3 is determined by the unique and similar amino acids found in or near the active sites of these enzymes. Most notably, the catalytic triad common to this class of proteinases is spatially conserved. Within the binding pocket of the P1 residue (S1 site) several significant differences in amino acid side chains are proposed by the model. The following described object compound of the present invention takes into account the unique aspartic acid and isoleucine amino acids found within the S1 pocket of the PR-3 model and can be represented by the following general formula.

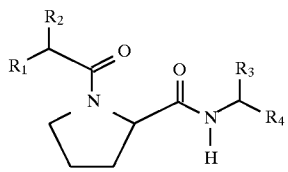

in which

R1, R2 are lower alkyl, optionally substituted ar(lower) alkyl, cyclo (lower) alkyl (lower) alkyl or optionally substituted heterocyclic (lower) alkyl, natural amino acids, —OH, —NH$_2$, lower alkylimino or lower alkylene;

R$^3$ is pyroyl, imidazoyl, butylamine, or ethyl-epoxide; and

R$^4$ is aldehyde, diphosphonylate, ethoxycourmarinyl, chloromethyl and difluoromethyl ketonyl.

An example of a PR-3 inhibitor based on this model is Boc-Val-Pro-His-p(OPh)$_2$. Inhibition of PR-3 activity by such a compound is unexpected in light of the generally accepted belief that elastase and PR-3 selectively bind and cut after residues quite different from histidine, namely those with short aliphatic side chains such as alanine.

EXAMPLE 10

Construction pAcCl3preproPR-3

The plasmid pAcCl3preproPR-3 was constructed for secretion of proPR-3 from Sf9 insect cells. This plasmid carries the native PR-3 leader, pro sequence, and the full-length mature human PR-3 gene coding sequence terminating after the Pro229 codon (See SEQ ID NO: 22), under control of the baculovirus polyhedron promoter. The 5' end of the PR-3 gene including the native leader (pre) and pro sequence was derived from the plasmid pGEMpreproPR-3-19, via PCR mutagenesis. The 3' end of the PR-3 gene was derived from the plasmid pGEMpreproPR-3-17 (as described in Example 2 as MY17), via the intermediate plasmids pGEM-metPR-3, pCDNA1-metPR-3, and pBS-met PR-3.

The plasmids pGEMpreproPR-3-17 and pGEM preproPR-3-19 were isolated from a cDNA library as described in Example 2. RNA was purified from HL60 cells by methods well known in the art and a cDNA library was constructed in the plasmid pGEM (PROMEGA, Madison, Wis.). Construction of the cDNA library used C tailing of cDNA and G tailing of the vector, followed by ligation. (*Gene Transfer and Expression*, 1990, pgs. 114–135). Clones were screened using a unique oligonucleotide probe described in Bories et al., *Cell* 59:959–968 (1989) in their published sequence of myeloblastin. Clones carrying pGEMpreproPR-3-17 and pGEMpreproPR-3-19 hybridized to the probe. Plasmid pGEMpreproPR-3-17(MY17) carries 8 bp of untranslated sequence 5' of the PR-3 leader start codon; plasmid pGEMpreproPR-3-19(MY19) carries 56 bp of 5' untranslated sequence, 5' of the PR-3 leader start codon.

As outlined in Example 2, the plasmid pGEM-metPR-3 was derived from pGEMPreProPR-3-17 using an oligonucleotide-directed site specific mutagenesis method described by Olsen and Eckstein (PNAS 87:1451–1455). Oligonucleotides DA403, which deleted the leader and added an ATG prior to the isoleucine at position 1 of the mature protein, and DA385, which added an EcoRI site 3' of the PR-3 gene for cloning purposes, were used in the mutagenesis. The sequences of these primers are:

DA385: 5'-XGAATACTCAAGCTT-GCATGCGAATTCGGCCAGCGCTGTGGGAGGGG-3' (SEQ ID NO. 9)

DA403: 5'-XCTCGTGCCCGCCCACGATCATTT-GCTGCAGGTCGACTCTAGA-3' (SEQ ID NO. 10)

where x=5' phosphate group

This modified gene was removed from pGEMmetPR-3 by EcoRI digestion and cloned into the EcoRI site of pCDNA1 to create pCDNA1-metPR-3. The plasmid pBSmetPR-3 was derived from pcDNA1metPR-3. The approximately 830 bp XbaI-EcoRI fragment containing the met PR-3 gene was excised from pcDNA1-met PR-3 with XbaI and EcoRI from New England Biolabs (Beverly, Mass.) and inserted into XbaI and EcoRI site of pBSIIKS +(Stratagene, La Jolla, Calif.). The resulting plasmid was designated pBSmetPR-3 and was used as the source of the 3' end of the PR-3 sequence in pAcCl3 preproPR-3.

pAcCl3 preproPR-3 was constructed by PCR mutagenesis using pGEMpreproPR-3-19 as a template. The 5' portion of the PR-3 gene was amplified from pGEMpreproPR-3-19 and then substituted for the 5' end in pBSmetPR-3. The expected PCR product was designed to include coding sequence for the native PR-3 leader sequence, (amino acids −27 through −3), the native pro sequence, (amino acids −1 and −2) as well as the coding sequence for PR-3 through the internal SmaI site. In addition, an XbaI site was introduced 5' of the native PR-3 leader (pre) sequence for cloning purposes. Oligonucleotide TS06 was used as the upstream primer:
5'-TTTTCTAGATCTAAGCTTATAAATGGCTCACCGG-CCC-3'
(SEQ ID NO.11); and oligonucleotide DA491 as the downstream primer
5'-CTGCCCGGGTTCCCCGCATCTGCAGGGAGGCC-ATGTAGGGCCGGGAGTGTGG CTGCGCCTCGTGCCCGCCCACGATCTCCGC-3'
(SEQ ID NO.12).
PCR amplification was performed for 35 cycles ramping to a denaturation temperature of 95° C. in one min., denaturing at 95° C. for 30 sec.; ramping to an annealing temperature of 55° C. in 2 min., 30 sec. annealing at 55° C. for 30 sec; ramping to an extension temperature of 72° C. in one min., extending at 72° C. for 1 min., 30 sec. Final extension was carried out at 72° C. for 10 min. Details of PCR are provided by Mullis, K. et al., U.S. Pat. No. 4,683,202; Ehrlich, H., U.S. Pat. No. 4,582,788 and Saiki et al., U.S. Pat. No. 4,683,195. Mullis, K. B. *Cold Spring Harbor Symp. Quant. Biol.* 51:263–273 (1986). The PCR product was digested with XbaI and SmaI and the resulting 153bp fragment ligated into the XbaI and SmaI sites of the vector pBS-metPR-3. Vector pBS-metPR-3 was digested with XbaI and SmaI then treated with calf intestinal alkaline phosphatase (NEB, Beverly, Mass.) at 50° C. for one hour then the phosphatase deactivated with 5mM Na EDTA, pH 8.0 at 75° C. for 10 min. Both the insert and vector were purified with GENECLEAN™ kit from BIO 101 (La Jolla, Calif.). The ligation mix was transformed into *E. coli* strain DH5α (GIBCO, BRL, Gaithersberg, Md. Plasmid pBSpreproPR-3 (pTS12-22), was isolated from an ampicillin resistant transformant using a Qiagen Midiprep column (Qiagen, Chatsworth Calif.). The presence of a single 153bp insert in this plasmid was shown by restriction analysis and confirmed by sequencing. After confirmation of the sequence, the approximately 850 bp BglII-EcoRI fragment, carrying the full length PR-3 coding sequence including the pre and pro sequence, was digested from pBSpreproPR-3 and ligated into the BglII and EcoRI sites of pAcC13 (derived from pVL941 Max Summers, Tex. A&M, Munemitsu et al., *Mol. Cell Biol.* 10:5977–5982 [1988]) to generate pAcC13preproPR-3 (pTS1-8-10).

EXAMPLE 11

Construction of TAF-166-7 and pAcC13preproPR-3 CΔ221

DNA encoding PR-3 protein terminating at amino acid 221 of the mature PR-3 sequence was constructed in the plasmid TAF166-7 (pAcCl3cecropin leader PR-3 CΔ221) to permit secretion of this form of truncated recombinant PR-3 from insect cells. Using PCR primer site-directed mutagenesis, the cDNA coding sequence for the eight C-terminal amino acids of PR-3 was deleted from the plasmid pAcC13:Myo (see Example 2), and a TGA stop codon added after the arg 221 codon.

The coding sequence for PR-3 was excised from the plasmid pBSmetPR-3 described above by digestion with SalI and EcoRV. The 750 bp fragment encoding PR-3 was separated by gel electrophoresis and recovered by freezing the gel slice at −20° C. for 20 min. then removing the agarose using a Spin-X™ column (Costar, Cambridge Mass.). This fragment was used as template for PCR.

The 3' portion of the PR-3 gene was amplified from the 750 bp fragment in a PCR reaction using primers LF69 and LF71. The sequences of the primers are:
LF69: 5'-CCTGCAGGAGCTCAATGTCACCGTGG-3'
(SEQ ID NO. 13)
LF71: 5'-CGCGTTGAGCTCTAGAGGATCCTCAGCG-CAGCGTGG-3'
(SEQ ID NO. 14)
The expected PCR product was designed to include PR-3 coding sequence from the internal SstI site to the codon for arg221, adding a TGA stop codon directly following arg221 in the coding sequence, then restriction sites, including SstI, for cloning. This product was amplified in two separate PCR reactions containing approximately 25 ng of template DNA, 50 pmoles LF69, 50 pmoles LF71, 37.5 μM dNTPs, 5% glycerol, 1X Perkin-Elmer Cetus PCR Buffer, and 2.5 units of Perkin-Elmer Cetus AmpliTaq® DNA polymerase in a 100 microliter volume. Before adding the AmpliTaq®, the reactions were brought to 95° C. The amplification was carried out for 25 cycles, ramping to a denaturation temperature of 95° C. in 1 sec., denaturing at 95° C. for 1 min; ramping to an annealing temperature of 68° C. in 1 sec., annealing at 68° C. for 1 min.; ramping to an extension temperature of 72° C. in 30 sec.; extending at 72° C. for 1 min. and 30 sec. Final extension was carried out at 72° C. for 10 min. The two reactions were pooled, extracted with phenol and chloroform, precipitated with ethanol, and the DNA was digested with SstI (Bethesda Research Laboratories, Gaithersburg Md.). The digested PCR product of approximately 244 bp was gel-purified using Qiaex beads (Qiagen, Chatsworth Calif.) and ligated to the 5' end of the PR-3 gene carried in the vector pAcC13:Myo (cecropin leader PR-3).

Vector DNA was prepared by digesting pAC13:Myo (see Example 2) with SstI, and treating with calf intestinal alkaline Phosphatase at 56° C. for 1 hr. The 9.5 kb fragment carrying the pAcC13 sequence, the cecropin leader sequence, and the 5' end of the PR-3 sequence was gel purified, electroeluted, extracted with phenol and chloroform, precipitated with ethanol, and resuspended in distilled water. SstI-digested PCR product was ligated to this vector. The ligations were transformed into DH5α competent cells (Bethesda Research Laboratories, Gaithersburg Md.). Plasmid TAF166-7 was isolated from an ampicillin-resistant transformant from this ligation and shown by restriction analysis and DNA sequencing to carry the sequence expected for a single insertion of the expected PCR product into the prepared vector [i.e. pAcC 13 with the cecropin leader followed by native PR-3 sequence (ile-val-gly . . . through amino acid arg221 followed by TGA stop codon)].

The plasmid pAcC13preproPR-3CΔ221 was constructed by excising the 5' portion of the pAcC13 cecropin leader construct, TAF166-7 (pAcC13 cecropin leaderPR-3CΔ221), described above with KpnI and NcoI and replacing it with the corresponding KpnI-NcoI fragment from the 5' portion of pAcC13preproPR-3 (pTS1-8-18). This results in a plasmid encoding the full-length PR-3 pre and pro sequence followed by the mature N-terminal sequence of PR-3 terminating at amino acid arg 221.

EXAMPLE 12

Construction of pAcC13FLA

The plasmid pAcC13FLA was constructed for secretion of the PR-3 mutein PR-3 V213A I216A L220A from Sf9 insect cells. The plasmid carries the native PR-3 leader and pro sequence and the full-length PR-3 gene, terminating after the Pro229 codon, with codons for three hydrophobic residues, which may comprise the hydrophobic face of an amphiphilic helix, mutated to ala codons. The plasmid pAcC13FLA was constructed using PCR mutagenesis and replacement of the entire PR-3 gene in the plasmid pAcC13preproPR-3, see Example 10.

Vector DNA was prepared by digesting the plasmid pAcC13preproPR-3 with BglII and EcoRI and treating with Calf Intestinal Alkaline Phosphatase (Boehringer Mannheim, Indianapolis, Ind.) at 37° C. for 2 hr. The 9.2 kb fragment carrying the pAcC13 vector sequence [RAF104] was gel purified using Qiaex beads (Qiagen, Chatsworth, Calif.).

The PR-3 gene was amplified from pAcC13preproPR-3 using the oligonucleotide primers LF96 and LF97. The sequences of these primers are:
LF96:
5'-CAGTTTTGTAATAAAAAAACCTATAAATATGCC-GGATTATTCATACCGTCCCAC CATCGGGCGCGGATCGGTACCAGATCTAAGCTTAT-AAATG-3' (SEQ ID NO: 15)
LF97:
5'-CCTCTAGAATTCGGCCAGCGCTGTGGGAGGGG-CGGTTCAGGGGCGGCCCTTGGC CTCCACACGGCGCGCCGTGGAACGGGCCCAGTC-AGCGTAGAG-3' (SEQ ID NO: 16)

The expected PCR product was designed to include the entire PR-3 coding sequence terminating after Pro229, including the native PR-3 leader and pro sequence, with codons Val213, Ile216, and Leu220 mutated to ala codons. The expected PCR product also includes a BglII site 5' of the leader sequence and an EcoRI site 3' of the TGA stop codon for cloning. This product was amplified in four separate PCR reactions, (PCR TNFα 68–71), containing approximately 200 ng of template DNA, 50 pmoles LF96, 50 pmoles LF97, 27.5 μM dNTPs, 5% glycerol, 1X Perkin-Elmer Cetus PCR Buffer, and 2.5 units of Perkin-Elmer Cetus AmpliTaq® DNA polymerase in a total of 100 microliters. Before adding the AmpliTaq®, the reactions were brought to 95° C. The amplifications was carried out for 25 cycles as described in Example 11. The four reactions were pooled, extracted with phenol and chloroform, precipitated with ethanol, and the DNA was digested with EcoRI and BglII. The digested PCR product of approximately 850 bp was gel-purified using Qiaex beads (Qiagen, Chatsworth, Calif.) [RAF105] and ligated to the EcoRI-BglII pAcC13 vector at an insert to vector ratio of approximately 3:1. The ligation was transformed into DH5α competent cells (Bethesda Research Laboratories, Gaithersburg, Md.). Plasmid pAcA13FLA was isolated from an ampicillin-resistant transformant from this ligation and shown by restriction analysis and DNA sequencing to carry the sequence expected for a single insertion of the expected PCR product in the prepared vector (i.e. pAcC13 with the native PR-3 gene including the PR-3 leader and pro sequence and terminating after codon Pro229, but containing mutations V213A, I216A, L220A).

EXAMPLE 13

Construction of preproPR-3 N102Q N147Q

In order to provide an amphiphilic helix PR-3 mutein and carbohydrate PR-3 mutein (free of N-linked glycosylation) to reduce product heterogeneity, the following plasmid is constructed. Plasmid pAcC13preproPR-3 CΔ221 (described above) is modified by site directed mutagenesis using variations of the methods described above. Specifically, the codons for asparagine 102 and 104 are altered to encode glutamine at these locations in the mature PR-3 sequence. The construct is then expressed in Sf9 cells as described above or in other cell cuture systems which permit expression. The secreted protein is then purified, activated, and formulated as described to crystallographic-grade PR-3 as described in Examples below.

EXAMPLE 14

Expression of proPR-3 in Sf9 Cells

The various pAcC13-based PR-3 expression plasmids (Munemitsu et al., *Mol. Cell Biol.* 10:5977–5982 [1988]) were recombined into the *Autographa californicia* baculovirus (AcNPV) by co-transfecting 2 μg of transfer vector with 0.5 μg of linearized, wild type viral DNA into Sf9 cells as described (Kitts et al., *Nucleic Acids Res.* 18:5667–5672). Recombinant baculovirus was isolated by plaque purification (Smith et al., *Mol. Cell Biol.* 3:2156–2165). Suspension cultures of 1.5×10⁶ Sf9 cells per ml were harvested for protein purifications and analysis following 48–72 hr infections with the relevant baculovirus at multiplicity of infection of 2–10, in serum-free medium (Maiorella et al., *Bio-Technology* 6:1406–1510).

EXAMPLE 15

Preparation of Recombinant proPR-3

Recombinant proPR-3 was produced in 1.4 liters of insect Sf9 cell culture (4×350 ml cultures with serum free medium as described in Maiorella et al., *Bio/Technology* 6:1406 [1988]) infected with baculovirus prepared as described in Example 14 utilizing the pAcC13preproPR-3 construct containing the human preproPR-3 clone described in Example 10. After 72 hr at 30° C. the culture was harvested and supernatant was retained following centrifugation at 3000 x g for 10 min. The supernatant fluid was filtered through a 0.8 micron filter and flow-through material was concentrated to 350 ml using an Amicon YM-10 spiral cartridge and dialyzed against loading buffer A (10 mM sodium phosphate, pH 7.0, containing 0.5 mM EDTA and 10% glycerol). The proPR-3 was loaded onto a Mono-S-Sepharose column (2.6×15 cm), washed with loading buffer and eluted with a 400 ml, 0–0.8 M sodium chloride gradient in loading buffer.

Fractions containing proPR-3 protein were identified by using dipeptidase-I (DPPI) to activate the proPR-3, followed by the determination of the PR-3 activity calorimetrically after addition of the PR-3 substrate, Boc-Ala-ONp as described in Example 4. Twenty-five μl of each S-Sepharose fraction were added to 75 μl of 50 mM sodium phosphate, pH 6.5, followed by the addition of 0.56 μl (0.011 units) of bovine DPPI (Boehringer Mannheim, Indianapolis, Ind.).

After 30 minutes at 37° C., 300 μl of 100 mM sodium phosphate buffer, pH 6.5, containing 10% acetonitrile and 0.5 mM Boc-Ala-ONp was added. The samples were allowed to sit at room temperature for 10–30 minutes and product formation measured spectrophotometrically by absorbance at 402 nm. Fractions enriched in proPR-3, as determined using this DPPI activation assay were pooled and concentrated by ultrafiltration on a YM-10 membrane to a final absorbance of 1.9 units at 280 nm.

EXAMPLE 16

Preparation of Active Recombinant PR-3

To obtain active PR-3 on a preparative scale from the pooled proPR-3, a small-scale activation experiment was performed on an aliquot of pooled proPR-3 to determine the optimal amount of DPPI required to quantitatively activate proPR-3. To each of five reactions containing 10 μl of concentrated Mono-S-Sepharose purified proPR-3, 1.5 μl of 746 uM sodium citrate, pH 4.0, was added. Dilutions of DPPI were prepared in 100 mM sodium citrate buffer, pH 4.0, and added to the proPR-3 reactions to final concentrations of 20%, 10%, 5%, 2.5% and 0.6% of pooled proPR-3/DPPI (wt/wt). After 3 hrs. the bioreactivity of the activated PR-3 was measured by transferring 5 μl of each reaction to a 400 μl solution of 100 mM sodium phosphate buffer, pH 6.5, containing 10% acetonitrile and 0.5 mM Boc-Ala-ONp. After approximately 10 min, the absorbance at 402 nm of each sample was measured. Based on these data, an effective amount of DPPI to be added to the preparative-scale activation was determined. Because DPPI appears not to overdigest the N-terminus of proPR-3, the effective amount of DPPI was chosen to be the lowest concentration resulting in 100% activation within the allotted incubation time. A ratio of about 2% (w/w) DPPI to total protein in the proPR-3 preparation is generally near the effective amount, depending on the proPR-3 preparation used.

A preparative scale activation reaction was then prepared using the entire Mono-S-Sepharose pool of proPR-3. Sodium citrate, pH 4.0, was added to the pooled proPR-3 fraction to a final concentration of 100 mM, followed by the addition of the effective amount of DPPI. After 3 hr at 37° C., the activated PR-3 was loaded onto a Vydac C4 column (25 × 0.46 cm), previously equilibrated in 0.1% trifluoroacetic acid (TFA). The PR-3 was eluted with a linear gradient of 0–60% acetonitrile in TFA in 45 minutes. The PR-3 eluted late in the chromatogram as a single peak of protein. Reverse phase high-performance liquid chromatography (RP-HPLC) fractions were assayed by diluting 20 μl of each fraction into 380 μl 100 mM sodium phosphate buffer, pH 6.5, containing 10% acetonitrile and 0.5 mM Boc-Ala-ONp. After approximately 10 minutes the absorbance at 402 nm of the assay samples was measured. The peak of activity measured in the colorimetric assay corresponded with the late-eluting peak of PR-3 protein. N-terminal sequence analysis of the purified PR-3 indicated that over 85% of the PR-3 had the N-terminal sequence expected for mature PR-3.

EXAMPLE 17

Alternative Preparation of Active Recombinant PR-3

An alternative method that did not use the acidic conditions of RP-HPLC was developed for purification of active PR-3. The proPR-3 was purified as described above through the Mono-S-Sepharose step and the DPPI activation. At the end of the activation reaction, the PR-3 was diluted 3-fold using deionized water and loaded onto a Pharmacia Mono-S column, previously equilibrated in loading buffer B (10 mM sodium phosphate buffer, pH 7.0, containing 0.1% (v/v) Triton X-100). After washing the column with three bed volumes of loading buffer B, the column was eluted with a 20-minute, 0–0. 8 M sodium chloride gradient at 1 ml/min flow rate. PR-3 eluted as the only major peak of protein in the gradient. PR-3 activity was measured across the column by diluting 10 μl of each fraction into 100 mM sodium phosphate buffer containing 10% acetonitrile and 0.5 mM Boc-Ala-ONp. The absorbance at 402 nm of each assay sample was measured after approximately 10 min. Fractions containing activated PR-3 were pooled and stored at 4° C. SDS-PAGE analysis of the purified PR-3 indicated that it was over 80% pure. The active PR-3 was stable over 1 month at 4° C. under these conditions.

EXAMPLE 18

Large-Scale Purification and Activation of rPR-3

In order to produce larger amounts of active recombinant PR-3 for use in screening inhibitors of native PR-3 and for mutein design, the following method was developed. Six liters of 48-hour serum-free conditioned medium from Sf9 insect cells infected with virus containing recombinant preproPR-3 described in Example 10 were used to produce PR-3. These cells secreted approximately 1–2 mg of proPR-3 per liter of medium. The conditioned medium was centrifuged as described in Example 15, then concentrated 20-fold using an SIY10 Spiral Ultrafiltration Cartridge (Amicon, Mass.), made 0.1% in Triton X-100 and dialyzed at 4° C. into 10 mM NaPO$_4$, pH 6.5 containing 1 mM EDTA and 0.1 % Triton X-100. The dialyzed retentate was loaded onto a S-Sepharose column (2.6×20 cm, Pharmacia Biotechnology, Inc., N.J.) equilibrated in dialysis buffer, washed and eluted with a 600-ml gradient of 0–1 M NaCl in the same buffer. Fractions enriched in proPR-3 were detected by enzymatic activity, following activation, as described in Examples 4, 15 and 16 with the following modifications: in a 96-well plate format, 5μl of DPPI diluted to 0.66 mg/ml with PBS containing 0.1% Triton X-100 was added to 100 μl of each fraction, incubation at 37° C. for 0.5 hours, brought up to 200 μl final volume with 0.8 mM Boc-Ala-ONp in 100 mM NaPO$_4$, pH 7.0 containing 5% DMSO and the absorbance at 405 nm was monitored by a plate reader. Fractions enriched with proPR-3 were pooled, concentrated 10-fold by Amicon YM10 ultrafiltration, and stored at 4° C. The protein concentration of the concentrate was determined to be 3 mg/ml using the BCA Protein Assay Reagent (Pierce Chemical Co., Rockford, Ill.) as compared to a purified bovine serum albumin standard. The recovery of proPR-3 at this step was approximately 50–60%, with a 10-fold purification.

To determine the minimum amount of DPPI required to activate the proPR-3 completely, on an expanded scale, a pilot activation step was performed. An aliquot of the partially purified proPR-3 was made 0.1 M in sodium citrate, pH 4.0, by addition of 1/10 volume of 1 M sodium citrate, pH 4.0. 12 μg of DPPI in two microliters was added to 20 μl of this aliquot to reach a final concentration of 20% (wt/wt) DPPI to total protein. Ten microliters of this mixture was 2-fold serially diluted into 10 μl of the pH adjusted aliquot to a final mix containing 0.313% (wt/wt) DPPI. Samples were incubated at 37° C. for 3 hours. After incubation, samples were diluted 1:50 with PBS containing 0.1% Triton X-100 and 8.5 μl of the diluted sample was assayed for PR-3 activity using 0.4 mM Boc-Ala-ONp as described in Example 4. Based on the comparison of rate of ONp released versus the wt/wt percentage of DPPI added, 1.25 % (wt/wt) was determined the minimum amount of DPPI required to obtain complete activation of PR-3 in 3 hr. at 37° C. for this preparation of proPR-3.

For preparative activation of the partially purified proPR-3, the pH of the remaining concentrated SP-Sepharose pool was adjusted as above, made 2% (wt/wt) in DPPI to total protein and incubated at 37° C. During incubation, aliquots were removed and assayed for PR-3 activity in order to determine when activation was complete. After 9.5 hours, the sample was diluted 1:4 with water and loaded onto a pyrogen-free Mono-S HR 10/10 Column (Pharmacia Biotechnology, Inc., N.J.) equilibrated in 10 mM $NaPO_4$, pH 6.5, 1 mM EDTA and 0.1% Triton X-100™. The proteins were eluted with a 75-ml gradient of 0–0.6 M NaCl in the same buffer, and fractions enriched in PR-3 were detected by assaying for enzymatic activity and analyzing on SDS-PAGE with Coomassie blue staining. Peak fractions were pooled and stored at 4° C. after filter sterilization. Protein concentration of the pool was determined as above. The PR-3 thus obtained was approximately 100-fold purified, ≧80% pure and represented about 40% of the mass of proPR-3 recovered from the conditioned medium. This activated rPR-3 was used in assays to confirm that the rPR-3 produced responded to known inhibitors of native PR-3 and was thus useful to identify inhibitors of PR-3 in vitro.

Neutralization of Recombinant PR-3 Activity with c-ANCA Antibody c-ANCA is human polyclonal antibody derived from patients with Wegener's Granulomatosis. Many c-ANCA preparations have been shown to neutralize the proteolytic activity of PR-3 preferentially, compared to the activity of other members of the granzyme family. Protein-A-purified human c-ANCA (supplied by Dr. Erik Hack, The Netherlands) was mixed with purified recombinant PR-3 prepared as described above at various molar ratios of antibody to enzyme, and after incubation for 1 hour at 37° C., residual enzyme activity was measured using the Boc-Ala-ONp substrate as described in Example 4. Consequently, identification of inhibitors of PR-3 may be successfully accomplished in screens utilizing recombinant PR-3 of the purity described. The enzymatic activity of the purified recombinant PR-3 was completely inhibited by a 50-fold molar excess of protein-A-purified c-ANCA antibody specific for PR-3.

The catalytic specificity of recombinant PR-3 was tested by comparing its sensitivity to two previously identified peptide diphosphonate inhibitors of native PR-3.

The two peptide diphosphonate inhibitors, Boc-Ala-Pro-Val-$(OPh)_2$ and Boc-Val-Pro-Val-$(OPh)_2$, were mixed at various concentrations with 125 ng of rPR-3 (prepared as described above) and incubated for 1 hour at 25° C. The residual enzyme activity was measured using the Boc-Ala-ONp substrate and compared to the same amount of enzyme incubated in the absence of inhibitor. Under these conditions, the Boc-Ala-Pro-Val-$(OPh)_2$ inhibited PR-3 with an $IC_{50}$ of about 10 μM and the Boc-Val-Pro-Val-$(OPh)_2$ inhibited PR-3 with an $IC_{50}$ of about 0.4 μM. These results are in agreement with the ability of the same inhibitors to inhibit the activity of native TNFα convertase from HL60 cells and the activity of purified native PR-3. Thus, recombinant PR-3 may be employed in detection of useful inhibitors of native PR-3.

EXAMPLE 19

Assay for Inhibitors of rPR-3

To screen for inhibitors of PR-3, a microtiter plate inhibitor assay was performed. Potential inhibitory compounds were solubilized in 100% dimethylsulfoxide (DMSO) to a final concentration of 400 μM. Ten microliters of each solubilized compound was placed in each of four wells of a microtiter plate. To each well, 120 μl of 100 mM sodium phosphate buffer, pH 7.5, was added. Activated, purified recombinant PR-3 was diluted to a final concentration of 0.125 mg/ml in 100 mM sodium phosphate buffer (pH 7.5) containing 0.2% Triton x-100, and 20 μl of this solution was added to two of the four wells containing the potential inhibitor. A control solution lacking PR-3 was added to the other two wells. After 30 min at room temperature, 50 μl of 0.8 mM PR-3 substrate freshly prepared in 100 mM sodium phosphate buffer, pH 7.5 containing 5.5% DMSO, was added to each well on the microtiter plate to a final substrate concentration of 0.2 mM. The substrate was initially solubilized in 100% DMSO to a final concentration of 40 mM and then diluted to 0.8 mM in 3.5% DMSO. The absorbance change in each well was measured at 405 nm using a plate reader. Using the Boc-Ala-nitrophenyl ester substrate (Sigma, St. Louis, Mo.), the assay was continuously monitored over a 10–15 minute reaction time. With the MeOSuc-Ala-Ala-Pro-Val-Nitroanilide (SEQ ID NO:28) substrate (Sigma) at 0.2 mM, the assay was monitored continuously over several hours. Eight control wells were included per plate, four wells containing DMSO, substrate, but without enzyme or potential inhibitor (background control), and four wells with DMSO, substrate and enzyme without potential inhibitor compound (maximum activity control). Triton X-100 (0.02%) was included in the assay to decrease non-specific inhibition of PR-3 activity possibly caused by poor solubility of the protein. Compounds that were found to inhibit PR-3 by this assay were further analyzed to determine the $K_i$ of the inhibitor and to determine mode of inhibition using methods well known in the art, but employing assays for PR-3 and substrate concentrations varying from about 0.05 mM to about 0.5 mM.

EXAMPLE 20

Production of Therapeutic and Crystallographic Grade PR-3

In order to generate therapeutic-grade PR-3, the Mono-S purified recombinant PR-3 (obtained as described in Example 16) was subjected to size-exclusion chromatography. 0.8 mg of protein from the Mono-S pool was concentrated to 2 mg/ml by Amicon YM10 ultrafiltration and loaded onto a S-300 HR column (1.6×60 cm. Pharmacia Biotechnology, Inc., N.J.) and chromatographed with a mobile phase of PBS containing 0.04 % Triton X-100. Fractions enriched in PR-3 were detected by assaying for enzymatic activity (Boc-Ala-ONP assay) and analyzing on SDS-PAGE with Coomassie blue staining. A single band of 28 kD was observed. The PR-3 eluted with a retention time correlating to an apparent molecular mass of 35 kD as compared to BSA and chymotrypsinogen A chromatographed in the same buffer. This process produced PR-3 that was ≧95 % pure with an overall recovery of about 25 % and a lipopolysaccharide content of ≦about 10 ng per mg of protein as measured using an Limulus Amoebocyte Lysate Assay (Associates of Cape Cod, Inc., Woods Hole, Mass.). The purified enzyme has a specific activity of approximately 30 units per mg (where a unit is defined as 1 micromole of product produced from cleavage of Boc-Ala-ONP permin. at 25° C., pH 7.5) and a $K_{cat}$ of approximately 12 per second.

Crystallization of a protein is a critical step in determining the crystal structure of that protein by X-ray diffraction. For proteins that require a detergent in order to remain soluble in an aqueous solution, crystallization is often conducted in the presence of a detergent, and octylglucoside is a preferred detergent. Two mg of purified recombinant PR-3 of "screening-grade" quality as described in Example 16 was dialyzed into 10 mM $PO_4$ (pH 6.5), 1 mM EDTA, 1% (wt/wt) octylglucoside and loaded onto a Mono-S column (Pharmacia) equilibrated in the same buffer. The column was washed with approximately 10 column volumes to exchange the Triton-X-100 for octylglucoside, then eluted with a 10-min/gradient of increasing NaCl to 0.6 M in the same buffer. Fractions enriched for PR-3 were detected by the calorimetric Boc-Ala-ONp enzyme assay described in Example 4, pooled, and concentrated 2-fold with a Centricon 10 (Amicon). The concentrated pool was chromatographed on an S300 HR size-exclusion column (Pharmacia) with dimensions of 1.6×60 cm, using a mobile phase of PBS containing 1 % (wt/wt) octylglucoside. Fractions enriched for PR-3 were detected by the same colorimetric enzyme assay using Boc-Ala-ONp and analyzed by SDS/PAGE with Coomassie staining. This process yielded approximately 1.5 mg of PR-3 that was over 95 % pure. N-terminal sequencing of this material detected a single sequence, corresponding to the expected N-terminus of mature, active PR-3 (Ile, Val, Gly, Gly . . . ). Alternatively, one of the repeated Mono-S steps can be eliminated in order to optimize recovery of crystal-grade PR-3 by performing the Mono-S step after activiation of proPR-3 with DPPI using 1% octylglucoside instead of 0.1% Triton X-100. The partially purified active PR-3 would then be purified to homogeneity by SEC as described above.

EXAMPLE 21

Production of Recombinant Proelastase

Recombinant human neutrophil elastase (Takahashi et al., J. Biol. Chem. 263:14739–14747 (1988)) may also be produced from its pro-form using the methods described above for the production of active recombinant PR-3.

To facilitate the production of active recombinant human elastase, a plasmid is constructed which carries the native elastase leader pro-sequence and coding sequence under the control of the baculovirus polyhedron promoter. The general methods for constructing such plasmids are exemplified in Examples 10, 11, and 12.

This plasmid is then used in the production of a recombinant baculovirus containing the human proelastase sequences by methods well known in the art (see, Summers and Smith Tex. Agric. Expt. Stat. Bull. 1555 [1983]; Smith et al., Mol. Cell Biol. 3:2156 [1983]; and Maiorella et al., Bio/Technology 6:1406 [1988]).

Once the recombinant virus is generated, it is then used to infect Sf9 cells at a multiplicity of infection of about 5–10 plaque-forming units of recombinant virus/cell. Cultures are typically grown in protein-free medium such as that described in Maiorella et al.

Recombinant proelastase is produced and purified using methods described in Example 15. For example, after growth of infected cells at 30° C. for 48–72 hours, the cells are removed from the culture medium by centrifugation at about 3000 x g for 10 min and the resulting supernatant fluid is filtered through a 0.8 micron filter. The culture medium containing proelastase is then concentrated using an Amicon YM-10 spiral cartridge and dialyzed against loading buffer A as described in Example 15. The concentrated proelastase is then loaded onto an S-Sepharose column, washed with loading buffer A, and eluted with a sodium chloride gradient in loading buffer.

Fractions containing proelastase may be identified using DPPI cleavage to remove its N-terminal amino acids Ser and Glu. Activation is monitored by the ability of the activated elastase to cleave an elastase substrate containing a chromophore. Activation is monitored using a colorimetric assay such as the colorimetric assays described for PR-3 above.

Proelastase may be activated using DPPI as described in Example 16 and Example 17. Other dipeptidases such as cathepsin D may also be used to remove the N-terminal dipeptide of proelastase. Endopeptidases specific for cleavage C-terminal to glutamic acids may also be useful for proelastase or proPR-3 activation.

Human proelastase and elastase produced by the methods described herein are useful in the screening of elastase inhibitors. In addition, the method of the present invention should provide quantities of recombinant elastase and elastase muteins of sufficient quality to allow crystallization and studies of three-dimensional structure of elastase alone or in complex with elastase inhibitors. Such information is useful for rational design of elastase inhibitors or for design of elastase molecules having modified elastase activities.

EXAMPLE 22

Conversion of 20 kD Recombinant Soluble ProTNFα to 17 kD TNFα as an Assay for TNFα Convertase and Its Inhibitors A construct encoding a soluble form of recombinant proTNFα was constructed for intracellular expression in yeast cells. It was designed to extend from the glycine at position −20, relative to the putative native TNFα N-terminus, to the end of native TNFα. The cDNA encoding human proTNFα was engineered to contain a methionine at position −21 based on mature TNFα amino acid numbering. The $Met_{-21}$ proTNFα sequence was transferred into the plasmid pBS24 for expression in S. cerevisiae. The final construct, p21METproTNF/BS24, utilizes the Upstream Activating Sequence of the alcohol dehydrogenase promoter linked to the glyceraldehyde-3-phosphate dehydrogenase promoter to direct efficient expression of Met $_{-21}$proTNF intracellularly in yeast. To produce the $Met_{-2}$proTNF protein, five liters of the engineered yeast cells were grown for 72 hrs in YPD medium containing 2% glucose and the cells were harvested by centrifugation at 5,000 x g for 30 min. The cells were resuspended in 200 ml of 25 mM Tris (pH 8.3) containing 10 mM EDTA, 200 μM PMSF and 2 μg/ml leupeptin and homogenized using three passes on a Dynamill. The homogenate was clarified by centrifugation at 10,000 x g for 30 min., diluted 3-fold using distilled, deionized, $H_2O$ and loaded onto a DEAE-Sepharose column (5×15 cm., Pharmacia, N.J.) equilibrated in 25 mM Tris pH (8.5) containing 1 mM EDTA, 1 μg/ml leupeptin and 200 μM PMSF. The proTNFα was eluted with a 0–0.8M sodium chloride gradient of 1.3 liters run in the Tris buffer described above. Fractions enriched in proTNF were identified by Western blot analysis, using a rabbit anti-human TNF polyclonal antibody prepared against rTNF expressed in E. coli.

The proTNFα was pooled, dialyzed into 10 mM sodium phosphate (pH 7.0) containing 1 mM EDTA, 1 αg/mL leupeptin, and 100 αM PMSF, and passed through an S-Sepharose column equilibrated in the pH 7.0 dialysis buffer. The S-Sepharose fall-through fraction was adjusted to pH 8.5 using 1 M sodium hydroxide and purified over a 5PW-DEAE-TSK HPLC column (21.5×150 mm) (BioRad, Calif.) using five replicate chromatography runs in the same pH 8.5 Tris buffer described above. The DEAE-TSK-HPLC column was run at 3 ml/min and eluted with a 0–0.8 M NaCl gradient over 60 min. Fractions enriched in Met$_{-21}$proTNFα were identified by SDS-PAGE analysis.

The DEAE-HPLC pool of proTNFα was concentrated 5-fold by ultrafiltration on a YM-10 membrane (Amicon) and then fractionated by replicate SE-HPLC on a Zorbax GF-250XL column (Dupont, de Nemours, Wilmington, Del.) run at 3 ml/min in 15 mM sodium phosphate buffer (pH 7.4) containing 150 mM NaCl. Fractions enriched in 20 kD Met $_{-21}$proTNFα were pooled, diluted 4-fold with SE-HPLC buffer and adjusted to 1.0 M ammonium sulfate by addition of solid.

The proTNF was further purified by hydrophobic interaction chromatography on a 5PW-Phenyl-TSK column (7.5×75 mm) (Biorad) equilibrated in 10 mM sodium phosphate (pH 7.0) containing 1.0 M ammonium sulfate. proTNFα was eluted using a criss-crossing gradient of 1.0–0 M ammonium sulfate, 0–30% ethylene glycol in 30 min at 1 ml/min. proTNFα eluted as a major peak (peak I) early in the chromatography and as a minor peak (peak II) which eluted late. Peak I proTNFα was pooled, dialyzed into 15 mM sodium phosphate buffer (pH 7.4) containing 150 mM sodium chloride, concentrated by ultrafiltration on a YM-10 membrane, filter sterilized, aliquoted and stored at −70° C.

The soluble proTNFα was shown to have biological activity in a TNFα biological assay (Carswell et al., *Proc. Natl. Acad. Sci. USA* 72:3666 [1975]), to have an apparent native MW (60 kD) consistent with a trimeric structure, and be convertable from a 20 kD reduced precursor to a molecular weight of 17 kD, characteristic of mature TNFα.

Inhibitors of TNFα convertase(s) may be identified by incubation with the PR-3 enzyme prior to or during a soluble proTNF cleavage assay. The soluble proTNF cleavage assay is performed as follows: Met$_{-21}$proTNFα (5 μM final concentration) is combined with TNFα convertase (0.05 μM final concentration) in 100 mM sodium phosphate buffer (pH 7.5) containing 0.02% Triton X-100 in the presence or absence of a potential TNFα convertase inhibitor. The reaction is analyzed over time for the conversion of 20 kD soluble proTNFα to 17 kD mature TNFα by SDS-PAGE analysis detected by Coomassie stain, silver stain, or Western Blotting using the rabbit anti-human TNFα antibody. SDS-PAGE analysis using Coomassie stain requires minimum of 0.2–2 μg of MET$_{-21}$proTNFα per sample. Silver-stained SDS-PAGE analysis or Western Blot analysis requires a minimum of 0.01–0.2 μg of Met$_{-21}$proTNF per sample. The activity of TNFα convertase can be quantitated using scanning densitometry to measure either the appearance of 17 kD TNF product over time or the disappearance of the 20 kD proTNF substrate. Inhibitors will be incubated with PR3 prior to and during a soluble proTNF cleavage assay and their inhibitory activity compared based on their IC$_{50}$ value, the concentration of inhibitor that inhibits 50% of the TNFα convertase activity in the assay.

An alternative assay utilizes two different polyclonal antibody preparations to detect the cleavage of Met$_{-21}$proTNFα by TNFα convertase. The assay may be run in an ELISA format by immobilizing the proTNFα substrate with a polyclonal antibody to 17 kD TNFα and detecting release of the 20-amino-acid proTNFα N-terminal fragment using a polyclonal antibody made to the 20-amino-acid N-terminal proTNFα peptide.

The present invention has been described with reference to specific embodiments. However, this application is intended to cover those changes and substitutions which may be made by those skilled in the art without departing from the spirit and the scope of the appended claims.

---

We claim:

1. A method of screening for a prophylactic or therapeutic medicament for a disease caused by, exacerbated by, or associated with the production of a mature tumor necrosis factor (TNFα), from a 26 kD proTNFα, the method comprising the steps of:

(a) contacting a 26 kD proTNFα or a proteolytically cleavable fragment thereof with a TNFα convertase from HL60 cells in an amount effective for cleaving the pro-TNFα or the proteolytically cleavable fragment, said proTNFα or said proteolytically cleavable fragment having the sequence: Gln-Ala-Val-Arg-Ser-Ser (SEQ ID NO: 24), within which proteolytic cleavage by TNFα convertase occurs;

(b) measuring either conversion of the proTNFα to the mature TNFα or cleavage of the cleavable fragment in step (a);

(c) repeating steps (a) and (b) further including a molecule sought to be identified as a prophylactive or a therapeutic medicament for diseases caused by the mature TNFα;

(d) measuring conversion of the proTNFα to mature TNFα or cleavage of the cleavable fragment in step (c); and (e) comparing the conversion or the cleavage measured in step (b) with the conversion or the cleavage measured in step (d), wherein lesser cleavage in step (d) than in step (b) suggests that the molecule is potentially a prophylactic or therapeutic medicament for diseases caused by mature TNFα.

2. The method of claim 1, wherein the disease is septic shock.

* * * * *